(12) United States Patent
Schweich, Jr. et al.

(10) Patent No.: US 10,265,166 B2
(45) Date of Patent: Apr. 23, 2019

(54) SYSTEMS AND METHODS FOR HEART VALVE THERAPY

(71) Applicant: Caisson Interventional, LLC, Maple Grove, MN (US)

(72) Inventors: Cyril J. Schweich, Jr., Maple Grove, MN (US); Kavitha Ganesan, Maple Grove, MN (US); Ramji Iyer, Maple Grove, MN (US); Erik O. Martz, Bloomington, MN (US); Lucas T. Schneider, Champlin, MN (US); Todd J. Mortier, Mound, MN (US)

(73) Assignee: Caisson Interventional, LLC, Maple Grove, MN (US)

( * ) Notice: Subject to any disclaimer, the term of this patent is extended or adjusted under 35 U.S.C. 154(b) by 0 days.

(21) Appl. No.: 15/393,704

(22) Filed: Dec. 29, 2016

(65) Prior Publication Data

US 2017/0189177 A1    Jul. 6, 2017

Related U.S. Application Data

(60) Provisional application No. 62/272,865, filed on Dec. 30, 2015.

(51) Int. Cl.
*A61F 2/24*    (2006.01)

(52) U.S. Cl.
CPC .......... *A61F 2/2418* (2013.01); *A61F 2/2436* (2013.01); *A61F 2/2439* (2013.01); *A61F 2210/0014* (2013.01); *A61F 2220/0008* (2013.01); *A61F 2220/0016* (2013.01); *A61F 2220/0075* (2013.01); *A61F 2250/001* (2013.01); *A61F 2250/006* (2013.01); *A61F 2250/0098* (2013.01)

(58) Field of Classification Search
CPC ..................................... A61F 2/06; A61F 2/84
USPC ..................................................... 623/1.1–3.1
See application file for complete search history.

(56) References Cited

U.S. PATENT DOCUMENTS

| | | |
|---|---|---|
| 4,680,031 A | 7/1987 | Alonso |
| 5,423,887 A | 6/1995 | Love et al. |
| 5,662,704 A | 9/1997 | Gross |
| 5,855,601 A | 1/1999 | Bessler et al. |

(Continued)

FOREIGN PATENT DOCUMENTS

| | | |
|---|---|---|
| EP | 350302 | 1/1990 |
| EP | 592410 | 4/1994 |

(Continued)

OTHER PUBLICATIONS

International Search Report and Written Opinion in International Application No. PCT/US2016/069201, dated Apr. 28, 2017, 12 pages.

(Continued)

*Primary Examiner* — Yashita Sharma
(74) *Attorney, Agent, or Firm* — Fish & Richardson P.C.

(57) ABSTRACT

Prosthetic heart valves described herein can be deployed using a transcatheter delivery system and technique to interface and anchor in cooperation with the anatomical structures of a native heart valve. Some embodiments of prosthetic mitral valves described herein include an anchor portion that couples the prosthetic mitral valve to the anatomy near the native mitral valve, and a valve portion that is mateable with the anchor portion.

30 Claims, 31 Drawing Sheets

(56) References Cited

U.S. PATENT DOCUMENTS

| | | |
|---|---|---|
| 5,984,959 A | 11/1999 | Robertson et al. |
| 6,113,631 A | 9/2000 | Jansen |
| 6,296,662 B1 | 10/2001 | Caffey |
| 6,309,417 B1 | 10/2001 | Spence et al. |
| 6,332,893 B1 | 12/2001 | Mortier et al. |
| 6,358,277 B1 | 3/2002 | Duran |
| 6,425,916 B1 | 7/2002 | Garrison et al. |
| 6,530,952 B2 | 3/2003 | Vesely |
| 6,569,196 B1 | 5/2003 | Vesely |
| 6,582,462 B1 | 6/2003 | Andersen et al. |
| 6,629,534 B1 | 10/2003 | St. Goar et al. |
| 6,730,118 B2 | 5/2004 | Spenser et al. |
| 6,730,121 B2 | 5/2004 | Ortiz et al. |
| 6,767,362 B2 | 7/2004 | Schreck |
| 6,769,434 B2 | 8/2004 | Liddicoat et al. |
| 6,790,229 B1 | 9/2004 | Berreklouw |
| 6,883,522 B2 | 4/2005 | Spence et al. |
| 6,893,459 B1 | 5/2005 | Macoviak |
| 6,893,460 B2 | 5/2005 | Spenser et al. |
| 6,908,481 B2 | 6/2005 | Cribier |
| 6,949,122 B2 | 9/2005 | Adams et al. |
| 7,011,681 B2 | 3/2006 | Vesely |
| 7,018,406 B2 | 3/2006 | Seguin et al. |
| 7,044,966 B2 | 5/2006 | Svanidze et al. |
| 7,101,396 B2 | 9/2006 | Artof et al. |
| 7,147,663 B1 | 12/2006 | Berg et al. |
| 7,160,322 B2 | 1/2007 | Gabbay |
| 7,175,656 B2 | 2/2007 | Khairkhahan |
| 7,217,287 B2 | 5/2007 | Wilson et al. |
| 7,252,682 B2 | 8/2007 | Seguin |
| 7,320,704 B2 | 1/2008 | Lashinski et al. |
| 7,329,278 B2 | 2/2008 | Seguin et al. |
| 7,381,218 B2 | 6/2008 | Schreck |
| 7,381,220 B2 | 6/2008 | Macoviak et al. |
| 7,393,360 B2 | 7/2008 | Spenser et al. |
| 7,442,204 B2 | 10/2008 | Schwammenthal et al. |
| 7,503,930 B2 | 3/2009 | Sharkawy et al. |
| 7,510,575 B2 | 3/2009 | Spenser et al. |
| 7,524,330 B2 | 4/2009 | Berreklouw |
| 7,524,331 B2 | 4/2009 | Birdsall |
| 7,578,843 B2 | 8/2009 | Shu |
| 7,585,321 B2 | 9/2009 | Cribier |
| 7,597,711 B2 | 10/2009 | Drews et al. |
| 7,618,446 B2 | 11/2009 | Andersen et al. |
| 7,625,403 B2 | 12/2009 | Krivoruchko |
| 7,632,308 B2 | 12/2009 | Loulmet |
| 7,708,775 B2 | 5/2010 | Rowe et al. |
| 7,717,955 B2 | 5/2010 | Lane et al. |
| 7,722,666 B2 | 5/2010 | Lafontaine |
| 7,727,276 B2 | 6/2010 | MacHiraju |
| 7,748,389 B2 | 7/2010 | Salahieh et al. |
| 7,776,083 B2 | 8/2010 | Vesely |
| 7,780,725 B2 | 8/2010 | Haug et al. |
| 7,785,364 B2 | 8/2010 | Styrc |
| 7,837,727 B2 | 11/2010 | Goetz et al. |
| 7,896,915 B2 | 3/2011 | Guyenot et al. |
| 7,914,569 B2 | 3/2011 | Nguyen et al. |
| 7,935,144 B2 | 5/2011 | Robin et al. |
| 7,947,072 B2 | 5/2011 | Yang et al. |
| 7,947,075 B2 | 5/2011 | Goetz et al. |
| 7,959,672 B2 | 6/2011 | Salahieh et al. |
| 7,981,153 B2 | 7/2011 | Fogarty et al. |
| 7,988,725 B2 | 8/2011 | Gross et al. |
| 8,016,882 B2 | 9/2011 | Macoviak et al. |
| 8,025,695 B2 | 9/2011 | Fogarty et al. |
| 8,048,153 B2 | 11/2011 | Salahieh et al. |
| 8,052,749 B2 | 11/2011 | Salahieh et al. |
| 8,055,360 B2 | 11/2011 | Park et al. |
| 8,057,540 B2 | 11/2011 | Letac et al. |
| 8,062,355 B2 | 11/2011 | Figulla et al. |
| 8,092,518 B2 | 1/2012 | Schreck |
| 8,092,521 B2 | 1/2012 | Figulla et al. |
| 8,092,524 B2 | 1/2012 | Nugent et al. |
| 8,123,801 B2 | 2/2012 | Milo |
| 8,133,270 B2 * | 3/2012 | Kheradvar ............ A61F 2/2418 623/1.26 |
| 8,142,492 B2 | 3/2012 | Forster et al. |
| 8,157,852 B2 | 4/2012 | Bloom et al. |
| 8,157,853 B2 | 4/2012 | Laske et al. |
| 8,163,011 B2 | 4/2012 | Rankin |
| 8,172,898 B2 | 5/2012 | Alferness et al. |
| 8,182,528 B2 | 5/2012 | Salahieh et al. |
| 8,182,530 B2 | 5/2012 | Huber |
| 8,206,437 B2 | 6/2012 | Bonhoeffer et al. |
| 8,231,670 B2 | 7/2012 | Salahieh et al. |
| 8,236,049 B2 | 8/2012 | Rowe et al. |
| 8,246,677 B2 | 8/2012 | Ryan |
| 8,252,051 B2 | 8/2012 | Chau et al. |
| 8,262,724 B2 | 9/2012 | Seguin et al. |
| 8,273,120 B2 | 9/2012 | Dolan |
| 8,277,502 B2 | 10/2012 | Miller et al. |
| 8,282,051 B2 | 10/2012 | Nutaro et al. |
| 8,287,591 B2 | 10/2012 | Keidar et al. |
| 8,292,938 B2 | 10/2012 | Case |
| 8,308,796 B2 | 11/2012 | Lashinski et al. |
| 8,308,798 B2 | 11/2012 | Pintor et al. |
| 8,317,858 B2 | 11/2012 | Straubinger et al. |
| 8,323,332 B2 | 12/2012 | Agnew |
| 8,323,335 B2 | 12/2012 | Rowe et al. |
| 8,348,998 B2 | 1/2013 | Pintor et al. |
| 8,403,983 B2 | 3/2013 | Quadri et al. |
| 8,449,599 B2 | 5/2013 | Chau et al. |
| 8,454,686 B2 | 6/2013 | Alkhatib |
| 8,460,366 B2 | 6/2013 | Rowe |
| 8,500,798 B2 | 8/2013 | Rowe et al. |
| 8,512,398 B2 | 8/2013 | Alkhatib |
| 8,512,399 B2 | 8/2013 | Lafontaine |
| 8,568,477 B2 | 10/2013 | Lashinski et al. |
| 8,579,964 B2 | 11/2013 | Lane et al. |
| 8,585,755 B2 | 11/2013 | Chau et al. |
| 8,623,080 B2 | 1/2014 | Fogarty et al. |
| 8,628,569 B2 | 1/2014 | Benichou et al. |
| 8,628,571 B1 | 1/2014 | Hacohen et al. |
| 8,632,586 B2 | 1/2014 | Spenser et al. |
| 8,641,757 B2 | 2/2014 | Pintor et al. |
| 8,652,203 B2 | 2/2014 | Quadri et al. |
| 8,657,872 B2 | 2/2014 | Seguin |
| 8,685,085 B2 | 4/2014 | Guyenot et al. |
| 8,685,086 B2 | 4/2014 | Navia et al. |
| 8,696,742 B2 | 4/2014 | Pintor et al. |
| 8,728,155 B2 | 5/2014 | Montorfano et al. |
| 8,795,355 B2 | 8/2014 | Alkhatib |
| 8,795,356 B2 | 8/2014 | Quadri et al. |
| 8,808,371 B2 | 8/2014 | Cartledge |
| 8,834,564 B2 | 9/2014 | Tuval et al. |
| 8,840,662 B2 | 9/2014 | Salahieh et al. |
| 8,840,663 B2 | 9/2014 | Salahieh et al. |
| 8,845,720 B2 | 9/2014 | Conklin |
| 8,852,272 B2 | 10/2014 | Gross et al. |
| 8,858,620 B2 | 10/2014 | Salahieh et al. |
| 8,870,948 B1 | 10/2014 | Erzberger et al. |
| 8,870,949 B2 | 10/2014 | Rowe |
| 8,876,895 B2 | 11/2014 | Tuval et al. |
| 8,894,702 B2 | 11/2014 | Quadri et al. |
| 8,911,493 B2 | 12/2014 | Rowe et al. |
| 8,926,690 B2 | 1/2015 | Kovalsky |
| 8,926,691 B2 | 1/2015 | Chau et al. |
| 8,932,358 B1 | 1/2015 | Nehls |
| 8,961,595 B2 | 2/2015 | Alkhatib |
| 8,968,395 B2 | 3/2015 | Hauser et al. |
| 8,986,370 B2 | 3/2015 | Annest |
| 8,986,373 B2 | 3/2015 | Chau et al. |
| 9,005,277 B2 | 4/2015 | Pintor et al. |
| 9,005,278 B2 | 4/2015 | Pintor et al. |
| 9,017,399 B2 | 4/2015 | Gross et al. |
| 9,023,100 B2 | 5/2015 | Quadri et al. |
| 9,034,032 B2 | 5/2015 | McLean et al. |
| 9,034,033 B2 | 5/2015 | McLean et al. |
| 9,039,757 B2 | 5/2015 | McLean et al. |
| 9,039,759 B2 | 5/2015 | Alkhatib et al. |
| 9,050,188 B2 | 6/2015 | Schweich et al. |
| 9,066,801 B2 | 6/2015 | Kovalsky et al. |
| 9,072,604 B1 | 7/2015 | Melnick et al. |

(56) References Cited

U.S. PATENT DOCUMENTS

| | | |
|---|---|---|
| 9,084,676 B2 | 7/2015 | Chau et al. |
| 9,132,006 B2 | 9/2015 | Spenser et al. |
| 9,155,617 B2 | 10/2015 | Carpentier et al. |
| 9,168,130 B2 | 10/2015 | Straubinger |
| 9,168,133 B2 | 10/2015 | Spenser et al. |
| 9,173,738 B2 | 11/2015 | Murray, III et al. |
| 9,192,466 B2 | 11/2015 | Kovalsky et al. |
| 9,226,826 B2 | 1/2016 | Rust |
| 9,241,792 B2 | 1/2016 | Benichou et al. |
| 9,248,016 B2 | 2/2016 | Oba |
| 9,259,315 B2 | 2/2016 | Zhou et al. |
| 9,265,631 B2 | 2/2016 | Straubinger |
| 9,289,293 B2 | 3/2016 | Murad et al. |
| 9,295,547 B2 | 3/2016 | Costello et al. |
| 9,295,548 B2 | 3/2016 | Drews et al. |
| 9,295,550 B2 | 3/2016 | Nguyen et al. |
| 9,301,843 B2 | 4/2016 | Richardson et al. |
| 9,301,863 B2 | 4/2016 | Punga et al. |
| 9,331,328 B2 | 5/2016 | Eberhardt et al. |
| 9,339,377 B2 | 5/2016 | Quadri et al. |
| 9,339,378 B2 | 5/2016 | Quadri et al. |
| 9,339,379 B2 | 5/2016 | Quadri et al. |
| 9,339,380 B2 | 5/2016 | Quadri et al. |
| 9,339,382 B2 | 5/2016 | Tabor et al. |
| 9,345,573 B2 | 5/2016 | Nyuli et al. |
| 9,358,111 B2 | 6/2016 | Spence et al. |
| 9,370,423 B2 | 6/2016 | Ryan |
| 9,370,424 B2 | 6/2016 | Call et al. |
| 9,375,311 B2 | 6/2016 | Gloss et al. |
| 9,439,757 B2 | 6/2016 | Wallace et al. |
| 9,492,273 B2 | 6/2016 | Wallace et al. |
| 9,387,071 B2 | 7/2016 | Tuval et al. |
| 9,402,719 B2 | 8/2016 | Lane et al. |
| 9,402,721 B2 | 8/2016 | Buchbinder et al. |
| 9,414,913 B2 | 8/2016 | Beith et al. |
| 9,414,918 B2 | 8/2016 | Chau et al. |
| 9,433,503 B2 | 9/2016 | Tsukashina et al. |
| 9,456,896 B2 | 10/2016 | Quadri et al. |
| 9,468,525 B2 | 10/2016 | Kovalsky |
| 9,480,556 B2 | 11/2016 | Revuelta et al. |
| 9,480,559 B2 | 11/2016 | Vidlund et al. |
| 9,486,306 B2 | 11/2016 | Tegels et al. |
| 9,510,946 B2 | 12/2016 | Chau et al. |
| 9,522,062 B2 | 12/2016 | Tuval |
| 9,532,870 B2 | 1/2017 | Cooper et al. |
| 9,554,903 B2 | 1/2017 | Rowe et al. |
| 9,561,100 B2 | 2/2017 | Pintor et al. |
| 9,561,103 B2 | 2/2017 | Granada et al. |
| 9,572,662 B2 | 2/2017 | Morriss et al. |
| 9,579,194 B2 | 2/2017 | Elizondo et al. |
| 9,579,196 B2 | 2/2017 | Morriss et al. |
| 2001/0007956 A1 | 7/2001 | Letac et al. |
| 2001/0021872 A1 | 9/2001 | Bailey et al. |
| 2002/0151970 A1 | 10/2002 | Garrison et al. |
| 2003/0055492 A1 | 3/2003 | Shaolian et al. |
| 2003/0130726 A1 | 7/2003 | Thorpe et al. |
| 2004/0127982 A1 | 7/2004 | Machold et al. |
| 2004/0210307 A1 | 10/2004 | Khairkhahan |
| 2004/0260393 A1 | 12/2004 | Randert et al. |
| 2005/0010287 A1 | 1/2005 | Macoviak et al. |
| 2005/0137689 A1 | 6/2005 | Salaheih et al. |
| 2005/0137690 A1 | 6/2005 | Salahieh et al. |
| 2005/0165479 A1 | 7/2005 | Drews et al. |
| 2005/0197695 A1* | 9/2005 | Stacchino .............. A61F 2/2418 623/2.18 |
| 2006/0235509 A1 | 10/2006 | Lafontaine |
| 2007/0027533 A1 | 2/2007 | Douk |
| 2007/0168024 A1 | 7/2007 | Khairkhahan |
| 2007/0185565 A1 | 8/2007 | Schwammenthal et al. |
| 2008/0004697 A1 | 1/2008 | Lichetenstein et al. |
| 2008/0015671 A1 | 1/2008 | Bonhoeffer |
| 2008/0086164 A1 | 4/2008 | Rowe |
| 2008/0103586 A1 | 5/2008 | Styrc et al. |
| 2008/0140189 A1 | 6/2008 | Nguyen et al. |
| 2008/0183273 A1 | 7/2008 | Mesana |
| 2008/0208327 A1 | 8/2008 | Rowe |
| 2008/0221672 A1 | 9/2008 | Lamphere et al. |
| 2009/0005863 A1 | 1/2009 | Goetz et al. |
| 2009/0099640 A1* | 4/2009 | Weng .............. A61F 2/95 623/1.11 |
| 2009/0216312 A1 | 8/2009 | Straubinger et al. |
| 2010/0049315 A1 | 2/2010 | Kirson |
| 2010/0100173 A1 | 4/2010 | Lafontaine |
| 2010/0145440 A1 | 6/2010 | Keranen |
| 2010/0217382 A1 | 8/2010 | Chau et al. |
| 2010/0249894 A1 | 9/2010 | Oba |
| 2010/0249908 A1 | 9/2010 | Chau et al. |
| 2010/0262232 A1 | 10/2010 | Annest |
| 2010/0280606 A1 | 11/2010 | Naor |
| 2010/0298931 A1 | 11/2010 | Quadri et al. |
| 2010/0312333 A1 | 12/2010 | Navia et al. |
| 2010/0331972 A1 | 12/2010 | Pintor et al. |
| 2011/0004296 A1 | 1/2011 | Lutter et al. |
| 2011/0022168 A1 | 1/2011 | Cartledge |
| 2011/0040374 A1 | 2/2011 | Goetz et al. |
| 2011/0137397 A1 | 6/2011 | Chau et al. |
| 2011/0137410 A1 | 6/2011 | Hacohen |
| 2011/0166636 A1 | 7/2011 | Rowe |
| 2011/0208293 A1 | 8/2011 | Tabor |
| 2011/0218619 A1 | 9/2011 | Benichou et al. |
| 2011/0224785 A1 | 9/2011 | Hacohen |
| 2011/0245911 A1 | 10/2011 | Quill et al. |
| 2011/0257721 A1 | 10/2011 | Tabor |
| 2011/0282438 A1 | 11/2011 | Drews et al. |
| 2011/0295363 A1 | 12/2011 | Girard et al. |
| 2011/0301702 A1 | 12/2011 | Rust et al. |
| 2011/0319988 A1 | 12/2011 | Schankereli et al. |
| 2011/0319989 A1 | 12/2011 | Lane et al. |
| 2012/0010697 A1 | 1/2012 | Shin et al. |
| 2012/0016464 A1 | 1/2012 | Seguin |
| 2012/0022633 A1* | 1/2012 | Olson .............. A61F 2/2418 623/1.11 |
| 2012/0035722 A1 | 2/2012 | Tuval |
| 2012/0053675 A1 | 3/2012 | Borock |
| 2012/0059458 A1 | 3/2012 | Buchbinder et al. |
| 2012/0078357 A1 | 3/2012 | Conklin |
| 2012/0101571 A1 | 4/2012 | Thambar et al. |
| 2012/0136430 A1 | 5/2012 | Sochman et al. |
| 2012/0165930 A1 | 6/2012 | Gifford, III et al. |
| 2012/0310328 A1 | 12/2012 | Olson et al. |
| 2013/0053949 A1 | 2/2013 | Pintor et al. |
| 2013/0079869 A1 | 3/2013 | Straubinger |
| 2013/0090725 A1 | 4/2013 | Pintor et al. |
| 2013/0116777 A1 | 5/2013 | Pintor et al. |
| 2013/0172992 A1 | 7/2013 | Gross et al. |
| 2013/0184811 A1 | 7/2013 | Rowe et al. |
| 2013/0211508 A1 | 8/2013 | Lane et al. |
| 2013/0282110 A1 | 10/2013 | Schweich et al. |
| 2013/0282114 A1 | 10/2013 | Schweich et al. |
| 2013/0310923 A1* | 11/2013 | Kheradvar .............. A61F 2/2439 623/2.11 |
| 2013/0345799 A1 | 12/2013 | Lafontaine |
| 2014/0005778 A1 | 1/2014 | Buchbinder et al. |
| 2014/0012368 A1 | 1/2014 | Sugimoto |
| 2014/0012372 A1 | 1/2014 | Chau et al. |
| 2014/0012373 A1 | 1/2014 | Chau et al. |
| 2014/0039611 A1 | 2/2014 | Lane et al. |
| 2014/0052237 A1 | 2/2014 | Lane et al. |
| 2014/0200662 A1 | 7/2014 | Eftel et al. |
| 2014/0214156 A1 | 7/2014 | Navia et al. |
| 2014/0222136 A1 | 8/2014 | Geist et al. |
| 2014/0228946 A1 | 8/2014 | Chau et al. |
| 2014/0236291 A1 | 8/2014 | Schweich et al. |
| 2014/0257467 A1 | 9/2014 | Lane et al. |
| 2014/0316516 A1 | 10/2014 | Vidlund |
| 2014/0343669 A1 | 11/2014 | Lane et al. |
| 2014/0358223 A1 | 12/2014 | Rafiee et al. |
| 2014/0364943 A1 | 12/2014 | Conklin |
| 2015/0039083 A1 | 2/2015 | Rafiee |
| 2015/0094802 A1 | 4/2015 | Buchbinder et al. |
| 2015/0112433 A1 | 4/2015 | Schweich et al. |
| 2015/0127096 A1 | 5/2015 | Rowe et al. |
| 2015/0142103 A1 | 5/2015 | Vidlund |
| 2015/0150678 A1 | 6/2015 | Brecker |

(56) References Cited

U.S. PATENT DOCUMENTS

| | | |
|---|---|---|
| 2015/0157458 A1 | 6/2015 | Thambar et al. |
| 2015/0216656 A1 | 8/2015 | Pintor et al. |
| 2015/0216657 A1 | 8/2015 | Braido |
| 2015/0216660 A1 | 8/2015 | Pintor et al. |
| 2015/0238312 A1 | 8/2015 | Lashinski |
| 2015/0238313 A1 | 8/2015 | Spence et al. |
| 2015/0265402 A1 | 9/2015 | Centola et al. |
| 2015/0320553 A1 | 11/2015 | Chau et al. |
| 2015/0327995 A1 | 11/2015 | Morin et al. |
| 2015/0327996 A1 | 11/2015 | Fahim et al. |
| 2015/0327999 A1 | 11/2015 | Board et al. |
| 2015/0335421 A1 | 11/2015 | Figulla et al. |
| 2015/0342733 A1 | 12/2015 | Alkhatib et al. |
| 2015/0351906 A1 | 12/2015 | Hammer et al. |
| 2015/0359629 A1 | 12/2015 | Ganesan et al. |
| 2016/0045307 A1 | 2/2016 | Yohanan et al. |
| 2016/0045309 A1 | 2/2016 | Valdez et al. |
| 2016/0051362 A1 | 2/2016 | Cooper et al. |
| 2016/0074160 A1 | 3/2016 | Christianson et al. |
| 2016/0106539 A1 | 4/2016 | Buchbinder et al. |
| 2016/0120646 A1 | 5/2016 | Dwork et al. |
| 2016/0158000 A1 | 6/2016 | Granada et al. |
| 2016/0158001 A1 | 6/2016 | Wallace et al. |
| 2016/0158003 A1 | 6/2016 | Wallce et al. |
| 2016/0184095 A1 | 6/2016 | Spence et al. |
| 2016/0193044 A1 | 7/2016 | Achiluzzi |
| 2016/0199180 A1 | 7/2016 | Zeng et al. |
| 2016/0228251 A1 | 8/2016 | Nyuli et al. |
| 2016/0235529 A1 | 8/2016 | Ma et al. |
| 2016/0242906 A1 | 8/2016 | Morriss et al. |
| 2016/0270917 A1 | 9/2016 | Tuval et al. |
| 2016/0310268 A1 | 10/2016 | Oba et al. |
| 2016/0317290 A1 | 11/2016 | Chau et al. |
| 2016/0317304 A1 | 11/2016 | Spence et al. |
| 2016/0324631 A1 | 11/2016 | Lane et al. |
| 2016/0324633 A1 | 11/2016 | Gross et al. |
| 2016/0331523 A1 | 11/2016 | Chau et al. |
| 2016/0331531 A1 | 11/2016 | Quadri et al. |
| 2016/0331534 A1 | 11/2016 | Buchbinder et al. |
| 2016/0338826 A1 | 11/2016 | Chau et al. |
| 2016/0338829 A1 | 11/2016 | Call et al. |
| 2016/0346080 A1 | 12/2016 | Righini et al. |
| 2016/0354203 A1 | 12/2016 | Tuval et al. |
| 2016/0354204 A1 | 12/2016 | Braido et al. |
| 2016/0361162 A1 | 12/2016 | Richter et al. |
| 2016/0361163 A1 | 12/2016 | Yohanan et al. |
| 2016/0374801 A1 | 12/2016 | Jiminez et al. |
| 2017/0007398 A1 | 1/2017 | Drews et al. |
| 2017/0049564 A1 | 2/2017 | Board et al. |
| 2017/0056162 A1 | 3/2017 | Harewood |
| 2017/0056163 A1 | 3/2017 | Tayeb et al. |
| 2017/0056166 A1 | 3/2017 | Ratz et al. |
| 2017/0056176 A1 | 3/2017 | Rowe et al. |
| 2017/0095331 A1* | 4/2017 | Spenser ............... A61F 2/2412 |

FOREIGN PATENT DOCUMENTS

| | | |
|---|---|---|
| EP | 0592410 | 4/1994 |
| EP | 705081 | 10/2001 |
| EP | 1338255 | 8/2003 |
| EP | 825841 | 10/2003 |
| EP | 833595 | 10/2003 |
| EP | 910313 | 11/2003 |
| EP | 910314 | 11/2003 |
| EP | 0910314 | 11/2003 |
| EP | 1006949 | 10/2004 |
| EP | 1233731 | 12/2004 |
| EP | 1251803 | 6/2005 |
| EP | 2674130 | 6/2005 |
| EP | 1267753 | 10/2005 |
| EP | 830112 | 11/2005 |
| EP | 1171059 | 11/2005 |
| EP | 1328215 | 11/2005 |
| EP | 1318775 | 11/2006 |
| EP | 1474077 | 2/2007 |
| EP | 1143882 | 12/2007 |
| EP | 1180987 | 8/2008 |
| EP | 1237509 | 12/2008 |
| EP | 1562522 | 12/2008 |
| EP | 2000115 | 12/2008 |
| EP | 1330213 | 3/2009 |
| EP | 1610727 | 4/2009 |
| EP | 1343438 | 7/2009 |
| EP | 2078498 | 7/2009 |
| EP | 1684667 | 8/2009 |
| EP | 1408850 | 9/2009 |
| EP | 1653888 | 9/2009 |
| EP | 1049425 | 11/2009 |
| EP | 1703865 | 2/2010 |
| EP | 1682048 | 3/2010 |
| EP | 1509171 | 6/2010 |
| EP | 1968491 | 7/2010 |
| EP | 1176913 | 10/2010 |
| EP | 1465554 | 12/2010 |
| EP | 1940321 | 12/2010 |
| EP | 2258312 | 12/2010 |
| EP | 1441672 | 9/2011 |
| EP | 2160150 | 10/2011 |
| EP | 1603493 | 12/2011 |
| EP | 2399549 | 12/2011 |
| EP | 2399550 | 12/2011 |
| EP | 1788984 | 2/2012 |
| EP | 2055266 | 2/2012 |
| EP | 2420205 | 2/2012 |
| EP | 1621162 | 5/2012 |
| EP | 2138132 | 6/2012 |
| EP | 2476394 | 7/2012 |
| EP | 2124824 | 10/2012 |
| EP | 2088965 | 11/2012 |
| EP | 2526895 | 11/2012 |
| EP | 2526898 | 11/2012 |
| EP | 2526899 | 11/2012 |
| EP | 2529696 | 12/2012 |
| EP | 2529697 | 12/2012 |
| EP | 2529698 | 12/2012 |
| EP | 2529699 | 12/2012 |
| EP | 2537487 | 12/2012 |
| EP | 1919397 | 1/2013 |
| EP | 2015709 | 1/2013 |
| EP | 1750622 | 2/2013 |
| EP | 2257242 | 2/2013 |
| EP | 2260796 | 2/2013 |
| EP | 1701668 | 3/2013 |
| EP | 2260797 | 3/2013 |
| EP | 2340075 | 3/2013 |
| EP | 2260798 | 6/2013 |
| EP | 2626040 | 8/2013 |
| EP | 1758523 | 9/2013 |
| EP | 2073756 | 10/2013 |
| EP | 2109417 | 11/2013 |
| EP | 2477555 | 12/2013 |
| EP | 1838241 | 2/2014 |
| EP | 1926455 | 4/2014 |
| EP | 2405966 | 4/2014 |
| EP | 2257243 | 5/2014 |
| EP | 2316381 | 5/2014 |
| EP | 2745805 | 6/2014 |
| EP | 2117469 | 7/2014 |
| EP | 2124826 | 7/2014 |
| EP | 2258316 | 7/2014 |
| EP | 2749254 | 7/2014 |
| EP | 1667604 | 8/2014 |
| EP | 2211779 | 8/2014 |
| EP | 2772228 | 9/2014 |
| EP | 2142143 | 11/2014 |
| EP | 2815723 | 12/2014 |
| EP | 2815724 | 12/2014 |
| EP | 2815725 | 12/2014 |
| EP | 2254515 | 1/2015 |
| EP | 1465555 | 5/2015 |
| EP | 2068767 | 7/2015 |
| EP | 1702247 | 8/2015 |
| EP | 1729688 | 8/2015 |
| EP | 2262447 | 8/2015 |

(56) References Cited

FOREIGN PATENT DOCUMENTS

| | | |
|---|---|---|
| EP | 2901966 | 8/2015 |
| EP | 1804686 | 9/2015 |
| EP | 2675396 | 9/2015 |
| EP | 1734903 | 10/2015 |
| EP | 2254513 | 10/2015 |
| EP | 2544626 | 10/2015 |
| EP | 2926766 | 10/2015 |
| EP | 2926767 | 10/2015 |
| EP | 1748745 | 12/2015 |
| EP | 1755459 | 12/2015 |
| EP | 1850796 | 12/2015 |
| EP | 1991168 | 1/2016 |
| EP | 2254512 | 1/2016 |
| EP | 2263609 | 1/2016 |
| EP | 2012712 | 2/2016 |
| EP | 1585463 | 3/2016 |
| EP | 2170416 | 3/2016 |
| EP | 2278944 | 3/2016 |
| EP | 1871300 | 4/2016 |
| EP | 2572676 | 4/2016 |
| EP | 2626041 | 4/2016 |
| EP | 2237746 | 5/2016 |
| EP | 2582326 | 5/2016 |
| EP | 2618784 | 5/2016 |
| EP | 1734902 | 6/2016 |
| EP | 1906884 | 6/2016 |
| EP | 2190379 | 6/2016 |
| EP | 2416739 | 6/2016 |
| EP | 2572675 | 6/2016 |
| WO | WO 2005/062980 | 7/2005 |
| WO | WO 2009/155561 | 12/2009 |
| WO | WO 2011/109813 | 9/2011 |
| WO | WO 2011/119101 | 9/2011 |
| WO | WO 2012/103204 | 8/2012 |

OTHER PUBLICATIONS

U.S. Appl. No. 61/266,774, filed Dec. 16, 2009, Chau et al.
U.S. Appl. No. 61/287,099, filed Dec. 4, 2009, Chau et al.
European Search Report in European Application No. 15170546.4, dated Apr. 12, 2016, 7 pages.
International Preliminary Report on Patentability in International Application No. PCT/US2015/035303, dated Dec. 15, 2016, 11 pages.
International Search Report and Written Opinion in International Application No. PCT/US2015/056935, dated Feb. 12, 2016, 14 pages.
Supplementary European Search Report in European Application No. 13778768, dated Jan. 12, 2016, 7 pages.
US 9,532,869, 1/2017, Quadri et al. (withdrawn).

* cited by examiner

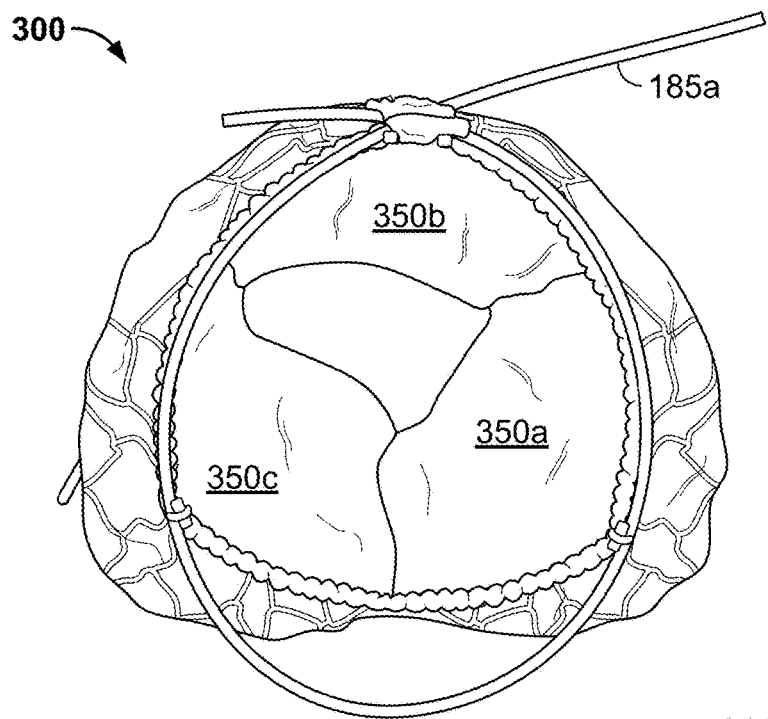
FIG. 33
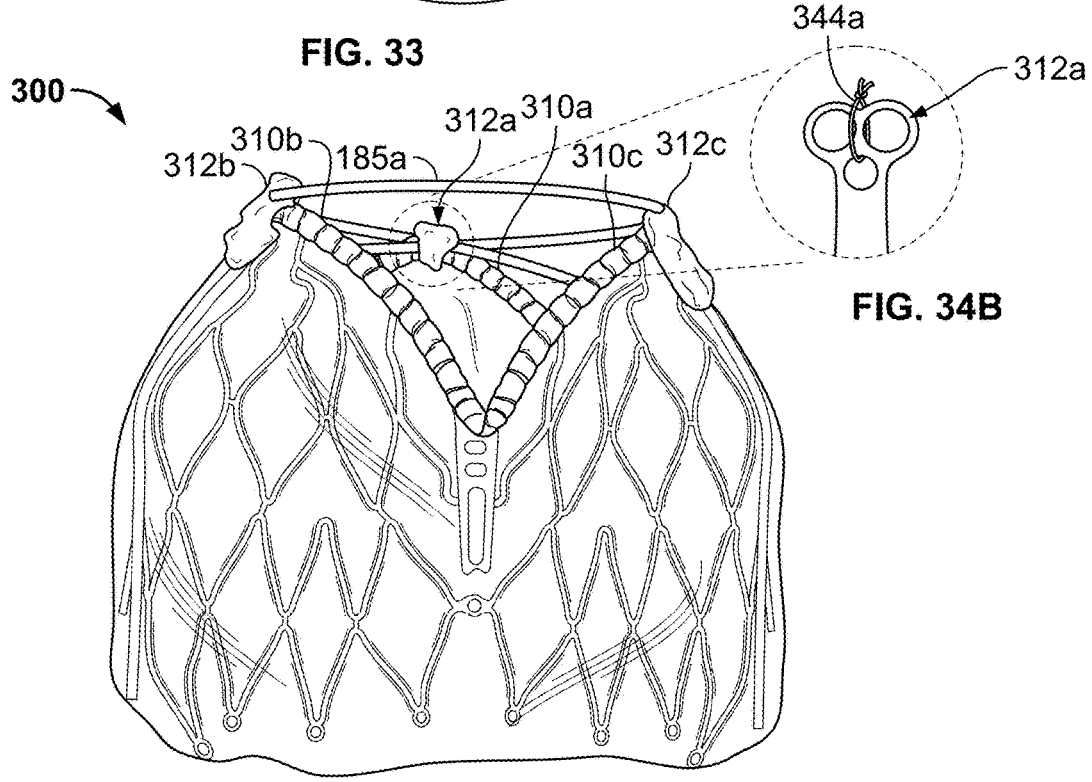
FIG. 34B
FIG. 34A

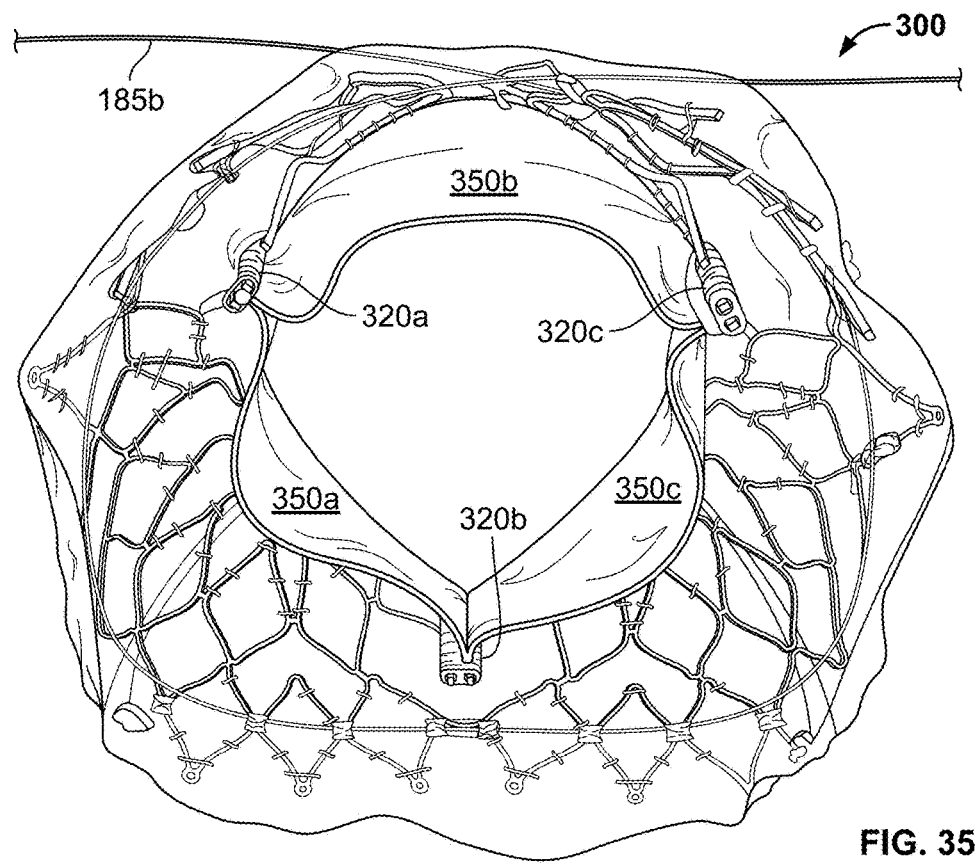
FIG. 35
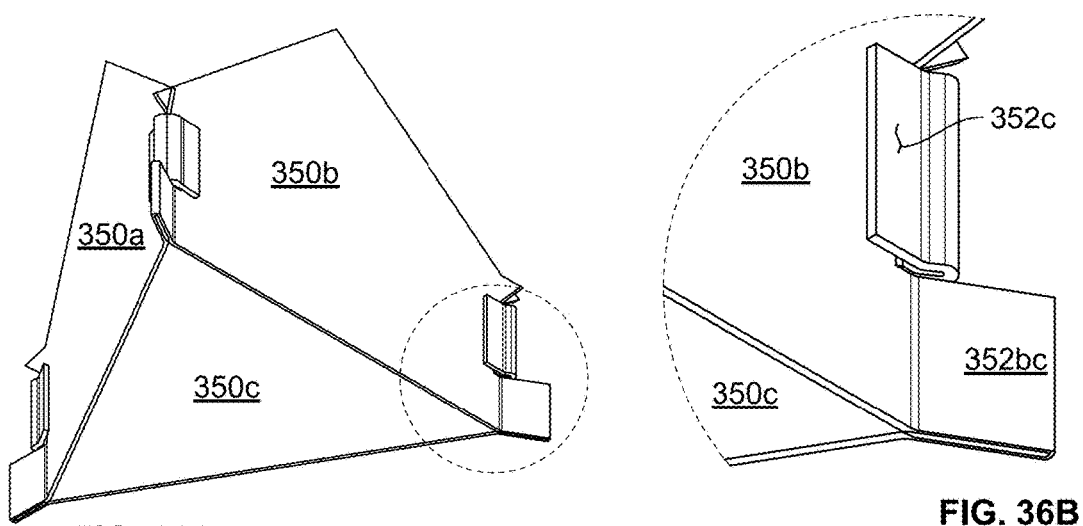
FIG. 36A
FIG. 36B

SYSTEMS AND METHODS FOR HEART VALVE THERAPY

CROSS-REFERENCE TO RELATED APPLICATIONS

This application claims the benefit of U.S. Provisional Ser. No. 62/272,865 filed Dec. 30, 2015. This disclosure of the prior application is considered part of (and is incorporated by reference in) the disclosure of this application.

TECHNICAL FIELD

This document relates to prosthetic heart valves, such as prosthetic mitral valves that can be implanted using transcatheter techniques. Some embodiments of prosthetic mitral valves described herein include an anchor portion that couples the prosthetic mitral valve to the anatomy near the native mitral valve, and a valve portion that is mateable with the anchor portion.

BACKGROUND

The long-term clinical effect of valve regurgitation is recognized as a significant contributor to cardiovascular related morbidity and mortality. Thus, for many therapies intended to treat the mitral valve, one primary goal is to significantly reduce or eliminate regurgitation. By eliminating the regurgitation at the mitral valve, the destructive volume overload effects on the left ventricle can be attenuated. The volume overload of mitral regurgitation (MR) relates to the excessive kinetic energy required during isotonic contraction to generate overall stroke volume in an attempt to maintain forward stroke volume and cardiac output. It also relates to the pressure potential energy dissipation of the leaking valve during the most energy-consuming portion of the cardiac cycle, isovolumetric contraction. Additionally, therapies for MR reduction can have the effect of reducing the elevated pressures in the left atrium and pulmonary vasculature reducing pulmonary edema (congestion) and shortness of breath symptomatology. Such therapies for MR reduction may also have a positive effect on the filling profile of the left ventricle (LV) and the restrictive LV physiology that can result with MR. These pathophysiologic issues indicate the potential benefits of MR therapy, but also indicate the complexity of the system and the need for a therapy to focus beyond the MR level or grade.

In some percutaneous access procedures in which a medical device is introduced through a patient's skin and into a patient's blood vessel, such an access can be used to introduce devices into the patient without the use of large cut downs, which can be painful and in some cases can hemorrhage or become infected. A percutaneous access generally employs only a small hole through the skin, which subsequently seals relatively easily, and heals quickly in comparison to a surgical cut down.

SUMMARY

This document describes prosthetic heart valves, such as prosthetic mitral valves, that can interface and anchor in cooperation with the anatomical structures of a native mitral valve. Some embodiments of prosthetic mitral valves described herein include an anchor portion that couples the prosthetic mitral valve to the anatomy near the native mitral valve, and a valve portion that is mateable with the anchor portion. In some implementations, a prosthetic mitral valve and deployment system includes a prosthetic mitral valve system, a system of multiple catheters configured to deliver the prosthetic mitral valve system, and a deployment frame system. At least some catheters of the multiple catheters are slidably engageable with each other. At least a first catheter of the multiple catheters is releasably coupleable to the prosthetic anchor assembly. At least a second catheter of the multiple catheters is releasably coupleable to the prosthetic valve assembly. The prosthetic mitral valve system can include a prosthetic anchor assembly comprising an anchor frame that defines an interior space, and a prosthetic valve assembly comprising a valve frame and multiple valve leaflets attached to the valve frame. The valve frame is configured to releasably couple with the prosthetic anchor assembly within the interior space of the anchor frame.

In one implementation, a prosthetic mitral valve system includes (i) a valve assembly comprising an expandable valve frame and an occluder attached to the expandable valve frame, and (ii) an anchor assembly comprising an expandable anchor frame that defines a longitudinal axis. The anchor assembly is configured to selectively couple with the valve assembly. The expandable anchor frame comprises a plurality of arched atrial holding features. While the expandable anchor frame is in an expanded configuration, each arched atrial holding feature of the plurality of arched atrial holding features extends transversely outward in relation to the longitudinal axis.

Such a prosthetic mitral valve system may optionally include one or more of the following features. The plurality of arched atrial holding features may comprise three arched atrial holding features. While the anchor assembly is coupled to a native mitral valve, each arched atrial holding feature of the plurality of arched atrial holding features may be positioned directly adjacent to, or spaced apart just superior to, an annulus of the native mitral valve.

In another implementation, a prosthetic mitral valve system includes (i) a valve assembly comprising an expandable valve frame and an occluder attached to the expandable valve frame, and (ii) an anchor assembly comprising an expandable anchor frame. The expandable valve frame comprises three valve frame lobes disposed on a proximal end portion of the expandable valve frame. The anchor assembly is configured to selectively couple with the valve assembly. The expandable anchor frame comprises three anchor frame lobes disposed on a proximal end portion of the expandable anchor frame. While the valve assembly and the anchor assembly are coupled, each valve frame lobe of the three valve frame lobes is aligned with a respective anchor frame lobe of the three anchor frame lobes.

Such a prosthetic mitral valve system may optionally include one or more of the following features. The expandable anchor frame may further comprise a plurality of arched atrial holding features. While the expandable anchor frame is in an expanded configuration, each arched atrial holding feature of the plurality of arched atrial holding features may extend transversely outward in relation to a longitudinal axis defined by the anchor assembly. The plurality of arched atrial holding features may comprise three arched atrial holding features. Each arched atrial holding feature of the three arched atrial holding features may be aligned with a corresponding valve frame lobe of the three valve frame lobes and with a corresponding anchor frame lobe of the three anchor frame lobes.

In another implementation, a prosthetic mitral valve system includes a valve assembly comprising an expandable valve frame and an occluder attached to the expandable valve frame, and an anchor assembly comprising an expandable anchor frame. The anchor assembly is configured to selectively couple with the valve assembly. The expandable anchor frame includes: (i) a centrally located hub; (ii) a first elongate element extending from the hub, the first elongate element including a first sub-annular foot; (iii) a second elongate element extending from the hub, the second elongate element including a second sub-annular foot; (iv) a third elongate element extending from the first elongate element, the third elongate element including a third sub-annular foot; and (v) a fourth elongate element extending from the second elongate element, the fourth elongate element including a fourth sub-annular foot. While the anchor assembly is coupled to a native mitral valve, each of the first foot, the second foot, the third foot, and the fourth foot are positioned within a sub-annular gutter of the native mitral valve.

Such a prosthetic mitral valve system may optionally include one or more of the following features. The expandable anchor frame may further comprise a systolic anterior motion containment member that is configured to be at least partially disposed behind an anterior leaflet of the native mitral valve while the anchor assembly is coupled to the native mitral valve. The systolic anterior motion containment member may extend from the first elongate element and the second elongate element. The hub may be located at a distal end of the expandable anchor frame. The hub may be threaded for releasable attachment with a delivery device.

In another implementation, a method for deploying a prosthetic mitral valve system within a native mitral valve of a patient includes: (i) navigating a delivery sheath of a prosthetic mitral valve delivery system through a vasculature of the patient such that a distal end of the delivery sheath is positioned adjacent the native mitral valve; (ii) expressing an anchor assembly of the prosthetic mitral valve system from the distal end of the delivery sheath such that the anchor assembly at least partially expands, the anchor assembly configured to selectively mate with a valve assembly of the prosthetic mitral valve system, the anchor assembly comprising an expandable anchor frame that includes three arched atrial holding features; (iii) engaging the anchor assembly with the native mitral valve such that each arched atrial holding feature of the three arched atrial holding features is positioned directly adjacent to, or spaced apart just superior to, an annulus of the native mitral valve; and (iv) mating the valve assembly with the anchor assembly.

In another implementation, a method for deploying a prosthetic mitral valve system within a native mitral valve of a patient includes: (i) navigating a delivery sheath of a prosthetic mitral valve delivery system through a vasculature of the patient such that a distal end of the delivery sheath is positioned adjacent the native mitral valve; (ii) expressing an anchor assembly of the prosthetic mitral valve system from the distal end of the delivery sheath such that the anchor assembly at least partially expands, the anchor assembly configured to selectively mate with a valve assembly of the prosthetic mitral valve system, the anchor assembly comprising an expandable anchor frame defining three anchor frame lobes disposed on a proximal end portion of the expandable anchor frame; (iii) engaging the anchor assembly with the native mitral valve; and (iv) mating the valve assembly with the anchor assembly. The valve assembly includes an expandable valve frame defining three valve frame lobes. As a result of the mating of the valve assembly with the anchor assembly, each of the three valve frame lobes is aligned with a respective anchor frame lobe of the three anchor frame lobes.

In another implementation, a method for deploying a prosthetic mitral valve system within a native mitral valve of a patient includes: (i) navigating a delivery sheath of a prosthetic mitral valve delivery system through a vasculature of the patient such that a distal end of the delivery sheath is positioned adjacent the native mitral valve; (ii) expressing an anchor assembly of the prosthetic mitral valve system from the distal end of the delivery sheath such that the anchor assembly at least partially expands. The anchor assembly is configured to selectively mate with a valve assembly of the prosthetic mitral valve system. The anchor assembly comprises an expandable anchor frame. The expandable anchor frame includes: a centrally located hub; a first elongate element extending from the hub, the first elongate element including a first foot; a second elongate element extending from the hub, the second elongate element including a second foot; a third elongate element extending from the first elongate element, the third elongate element including a third foot; and a fourth elongate element extending from the second elongate element, the fourth elongate element including a fourth foot. The method further comprises: (iii) engaging the anchor assembly with the native mitral valve such that each of the first foot, the second foot, the third foot, and the fourth foot are positioned within a sub-annular gutter of the native mitral valve; and (iv) mating the valve assembly with the anchor assembly.

In another implementation, a mitral valve system for deployment within a native mitral valve includes a valve means for expanding within a native mitral valve annulus and occluding regurgitation of blood flow from a left ventricle to a left atrium, and a means for anchoring the valve means within the native mitral valve annulus.

In another implementation a transcatheter mitral valve replacement system includes a valve assembly comprising an expandable valve frame and a set of occlude leaflets attached to the expandable valve frame, and an anchor assembly comprising an expandable anchor frame. The anchor assembly is configured to anchor with sub-annular tissue and to receivingly mate with the valve assembly.

In another implementation, a prosthetic mitral valve system includes: (i) a valve assembly comprising an expandable valve frame and an occluder attached to the expandable valve frame; (ii) an anchor assembly comprising an expandable anchor frame that defines a longitudinal axis, the anchor assembly configured to selectively couple with the valve assembly; and (iii) a control wire slidably engaged with the expandable anchor frame at a plurality of engagement locations at a mid-body region along the longitudinal axis of the expandable anchor frame. The control wire is manipulable to increase and decrease a diameter of the expandable anchor frame during implantation of the anchor assembly.

Such a prosthetic mitral valve system may optionally include one or more of the following features. The expandable anchor frame may include: (i) a centrally located hub; (ii) a first elongate element extending from the hub, the first elongate element including a first foot; (iii) a second elongate element extending from the hub, the second elongate element including a second foot; (iv) a third elongate element extending from the first elongate element, the third elongate element including a third foot; and (v) a fourth elongate element extending from the second elongate element, the fourth elongate element including a fourth foot. In some embodiments, tensioning the control wire draws each of the first foot, second foot, third foot, and fourth foot radially inwards towards the longitudinal axis, and slackening the control wire allows each of the first foot, second foot, third foot, and fourth foot to expand radially outwards away from the longitudinal axis. The control wire may be a first control wire, and the prosthetic mitral valve may further comprise a second control wire slidably engaged with the expandable anchor frame at a proximal end region of the expandable anchor frame. The proximal end region of the expandable anchor frame may comprise a plurality of arched atrial holding features. The second control wire may be manipulable such that tensioning the second control wire draws the plurality of arched atrial holding features radially inwards towards the longitudinal axis and slackening the second control wire allows the plurality of arched atrial holding features to extend transversely outward in relation to the longitudinal axis.

In another implementation a method for deploying a prosthetic mitral valve system within a native mitral valve of a patient includes: (i) navigating a delivery sheath of a prosthetic mitral valve delivery system through a vasculature of the patient such that a distal end of the delivery sheath is positioned in a left atrium of the patient; (ii) expressing an anchor assembly of the prosthetic mitral valve system from the distal end of the delivery sheath, the anchor assembly defining a longitudinal axis and configured to selectively mate with a valve assembly of the prosthetic mitral valve system; (iii) slackening a control wire of the prosthetic mitral valve delivery system to allow the anchor assembly to self-expand to a first diameter while the anchor assembly is within the left atrium; (iv) advancing, after the anchor assembly self-expands to the first diameter, at least a distal portion of the anchor assembly across an annulus of the native mitral valve such that the at least the distal portion of the anchor assembly is positioned within a left ventricle of the patient; and (v) slackening, after the at least the distal portion of the anchor assembly is positioned within the left ventricle, the control wire to allow the anchor assembly to self-expand to a second diameter that is larger than the first diameter.

Such a method for deploying a prosthetic mitral valve system within a native mitral valve of a patient may optionally include one or more of the following features. The anchor assembly may include: (a) a centrally located hub; (b) a first elongate element extending from the hub, the first elongate element including a first foot; (c) a second elongate element extending from the hub, the second elongate element including a second foot; (d) a third elongate element extending from the first elongate element, the third elongate element including a third foot; and (e) a fourth elongate element extending from the second elongate element, the fourth elongate element including a fourth foot. Each of the slackening the control wire steps may allow each of the first foot, second foot, third foot, and fourth foot to expand radially outwards away from the longitudinal axis. The method may further include seating, after the anchor assembly self-expands to the second diameter, each of the first foot, second foot, third foot, and fourth foot in a sub-annular gutter of the native mitral valve.

Some or all of the embodiments described herein may provide one or more of the following advantages. First, some embodiments of the prosthetic mitral valve systems provided herein can be used in a percutaneous transcatheter mitral replacement procedure (e.g., complete delivery and anchoring of the prosthetic valve components via one or more catheters advanced percutaneously into the venous system or arterial system and to the heart) that is safe, reliable, and repeatable by surgeons and/or interventional cardiologists of a variety of different skill levels. For example, in some implementations the prosthetic mitral valve system can establish a reliable and consistent anchor/ substrate to which the valve/occluder structure subsequently engages. Thus, the prosthetic mitral valve system can be specifically designed to make use of the geometry/mechanics of the native mitral valve to create sufficient holding capability. In one particular aspect, the anatomical gutter found below a native mitral valve annulus can be utilized as a site for anchoring the prosthetic mitral valve system, yet the anchoring structure can be deployed in a matter that maintains native leaflet function of the mitral valve, thereby providing the ability to completely separate and stage the implantation of the components of the prosthetic mitral valve system. Accordingly, some embodiments of the prosthetic mitral valve systems described herein are configured to be implanted in a reliable, repeatable, and simplified procedure that is broadly applicable to a variety of patients and physicians, while also employing a significantly less invasive method.

Second, some embodiments of the prosthetic mitral valve systems provided herein include features to facilitate convenient engagement of prosthetic mitral valve components to the deployment catheter system. For example, in preparation for deployment of the prosthetic valve assembly, a clinician may need to engage one or more control wires of the deployment catheter system with the valve assembly by threading the wire through multiple control wire engagement features located on the valve assembly. To assist the clinician with that task, in some embodiments the valve assembly is provided with a removable guide tube extending through each of the control wire engagement features. To engage a control wire with the valve assembly, the clinician inserts the control wire through the tube, and then removes the tube while leaving the control wire in place relative to the valve assembly. In that fashion, the control wire can be installed through each of the control wire engagement features in a convenient manner. The same feature can be included in the prosthetic anchor assembly.

Third, some embodiments of the prosthetic mitral valve systems and deployment systems include multiple control wires to provide highly user-controllable diametric expansion of the prosthetic mitral valve components during deployment. For example, some embodiments of the anchor assembly and anchor assembly deployment system include a first, proximal control wire and a second, mid-body control wire. As described further below, independent control of the proximal and mid-body portions of the anchor assembly during deployment can advantageously facilitate a user-friendly and clinically effective transcatheter deployment technique.

Fourth, some embodiments of the prosthetic mitral valve systems are configured to perform with reduced in situ stress levels. For example, in some embodiments, the structure of the anchor and/or valve assembly framework is specifically designed to function within the dynamic environment of the heart while incurring low levels of stress and strain within the framework members. Such features can allow for greater durability and longevity of the prosthetic mitral valve systems.

Fifth, some embodiments of the prosthetic mitral valve systems include features to reduce the potential of interference or entanglement with the native valve's chordae tendineae. For example, in some embodiments the anchor assembly framework is specifically designed such that particular sub-annular framework members extend essentially parallel with the chordae tendineae. In result, an anchor assembly can be implanted in a native mitral valve with minimal or no impact on the natural functioning of the native valve leaflets.

Sixth, in particular embodiments, the prosthetic mitral valve system can include two different expandable components (e.g., an anchor assembly and a valve assembly) that are separately delivered to the implantation site, and both components can abut and engage with native heart tissue at the mitral valve. For example, the first component (e.g., the anchor assembly) can be configured to engage with the heart tissue that is at or proximate to the annulus of the native mitral valve, and the second component (e.g., the valve assembly) can be configured to provide a seal interface with native valve leaflets of the mitral valve.

Seventh, in some embodiments the prosthetic mitral valve system includes features for enhanced coupling alignment and strength between the anchor assembly and the valve assembly. Such features may provide strong decoupling resistance and, in turn, enhanced migration resistance of the prosthetic mitral valve system.

Eighth, some embodiments of the prosthetic mitral valve systems described herein are configured with a systolic anterior motion SAM containment member feature. SAM containment members can reduce or prevent the potential for a natural mitral valve anterior leaflet to "flop" outward and/or from being drawn by a Venturi effect into the left ventricular outflow tract (LVOT). Accordingly, the SAM containment members can reduce the risk of full or partial blockages of the LVOT. In some patient scenarios, the potential for suffering future adverse health events, such as heart failure, is thereby reduced.

Ninth, using the devices, systems, and methods described herein, various medical conditions, such as heart valve conditions, can be treated in a minimally invasive fashion. Such minimally invasive techniques can tend to reduce recovery times, patient discomfort, and treatment costs.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 33 shows a top view of the valve assembly of FIGS. 26-30, including a threading tube coupled to the proximal end of the valve assembly.

FIG. 34A is an anterior side perspective view of the valve assembly of FIG. 33.

FIG. 34B shows an enlarged view of a proximal portion of the valve assembly of FIG. 34A.

FIG. 35 is bottom view of the valve assembly of FIG. 33.

FIG. 36A shows an assembly of prosthetic valve leaflet components for the valve assembly of FIG. 33, prior to being coupled to the valve frame.

FIG. 36B shows an enlarged view of a portion of the prosthetic valve leaflets of FIG. 36A.

Like reference symbols in the various drawings indicate like elements.

DETAILED DESCRIPTION OF ILLUSTRATIVE EMBODIMENTS

This disclosure describes embodiments of a prosthetic heart valve system, such as prosthetic mitral valve systems, and transcatheter systems and methods for implanting prosthetic heart valve systems. In some embodiments, the prosthetic mitral valve system can be deployed to interface and anchor in cooperation with the native anatomical structures of a mitral valve (and, optionally, in a manner that permits the continued natural function and movement of the chordae tendineae and the native mitral valve leaflets even after the anchor component is deployed).

Figure 1:
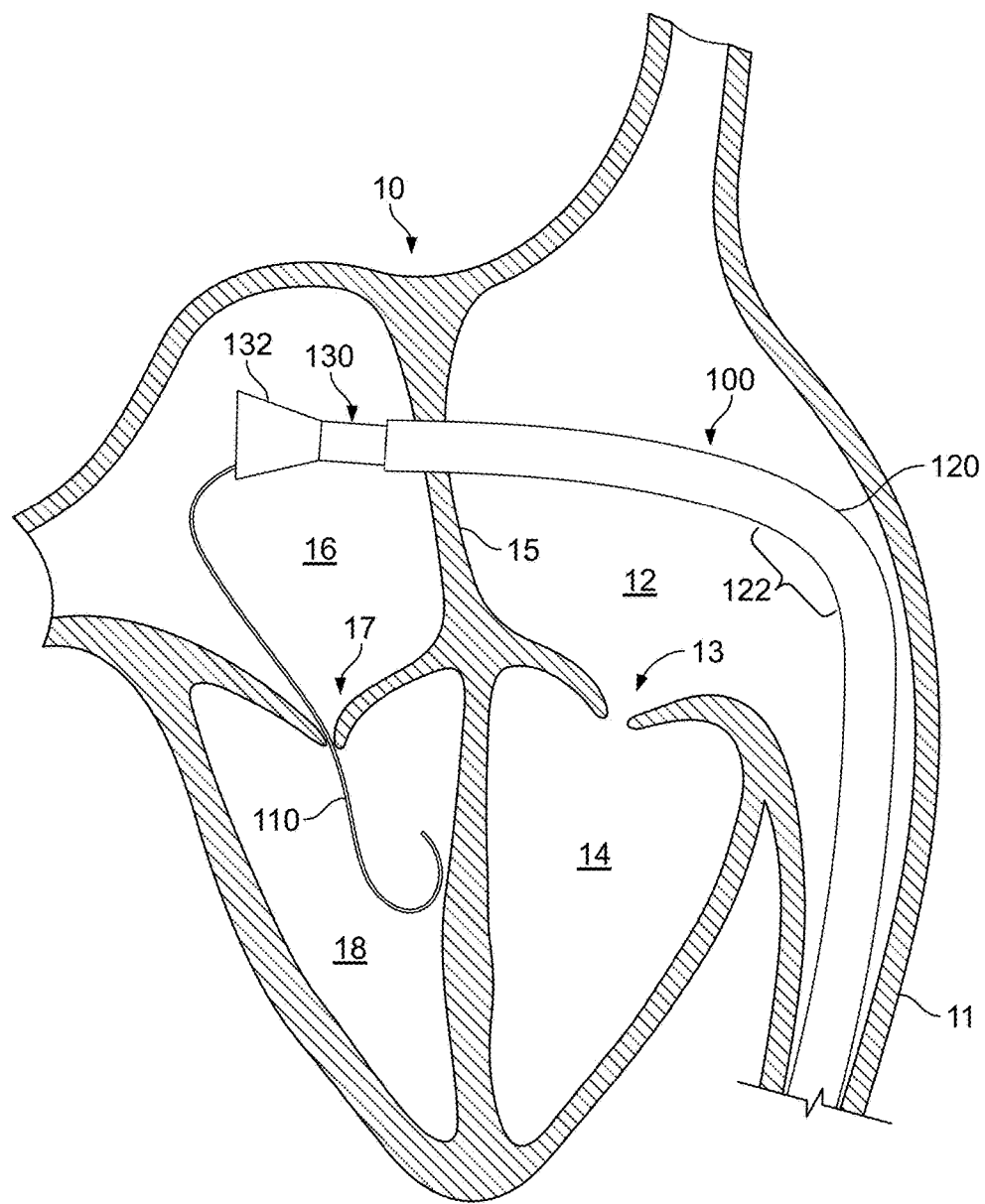
FIG. 1 shows a perspective view of a portion of a prosthetic mitral valve deployment system in a cross-sectional view of a native human heart (from a rear side of the heart), in accordance with some embodiments.

Referring to FIG. 1, an example transcatheter mitral valve delivery system 100 can be navigated through a patient's vasculature to obtain access to the patient's heart 10. The transcatheter delivery system 100 facilitates implantation of a prosthetic mitral valve in a beating heart 10 using a percutaneous, or minimally invasive technique (without open-chest surgery or open-heart surgery). For example, in some implementations the transcatheter delivery system 100 is percutaneously inserted into a femoral or iliac vein via a groin opening/incision 2 in a patient 1 (FIG. 43) using a deployment frame system 6 configured to activate and/or control the movements of various components of the transcatheter delivery system 100. In some implementations, the transcatheter delivery system 100 is used in conjunction with one or more imaging modalities such as x-ray fluoroscopy, echocardiography, magnetic resonance imaging, computed tomography (CT), and the like.

Figure 2:
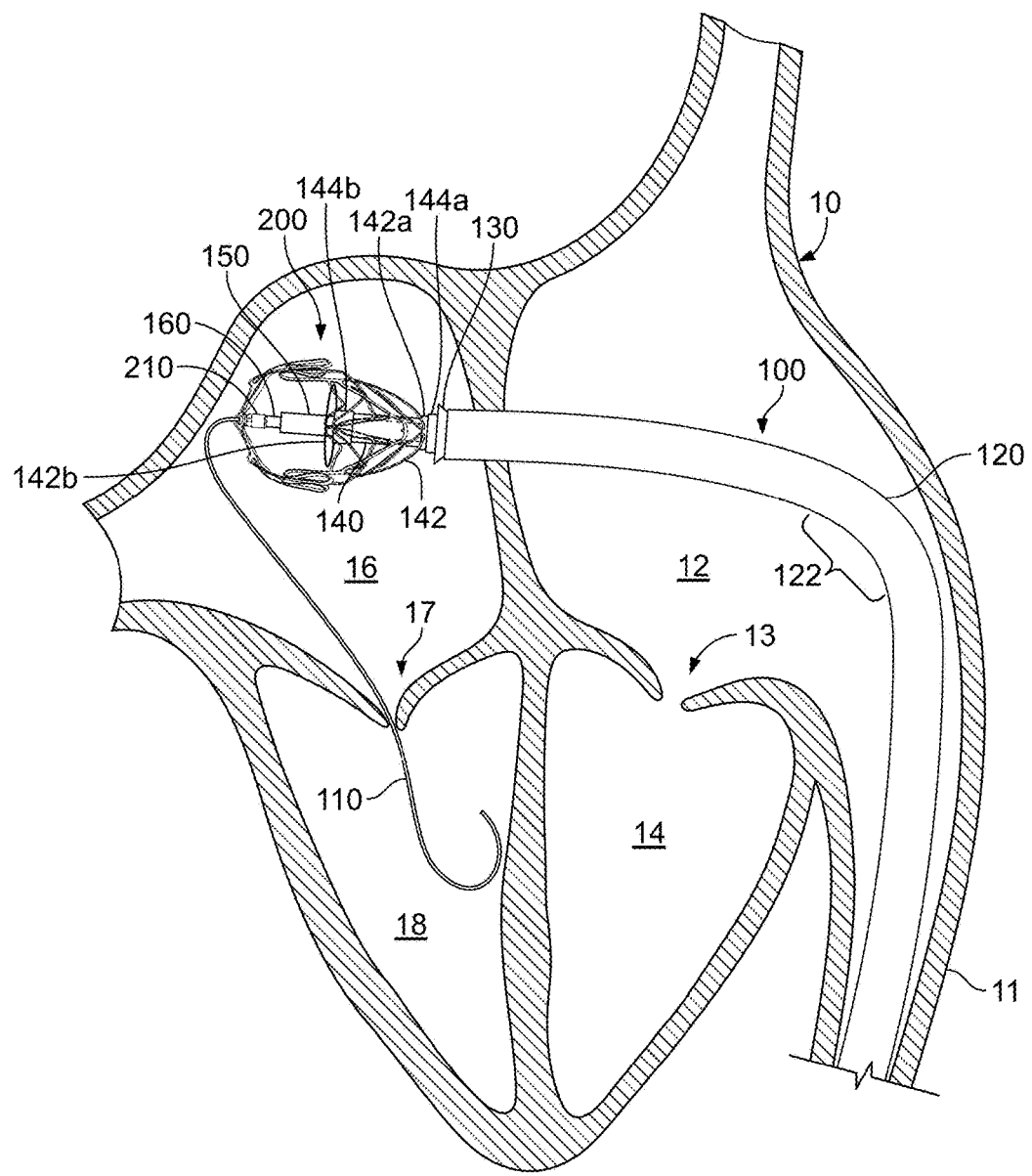
FIG. 2 shows a perspective view of a prosthetic mitral valve anchor assembly in the left atrium of the heart after the anchor assembly has emerged from an anchor delivery sheath of the deployment system of FIG. 1.
Figure 5:
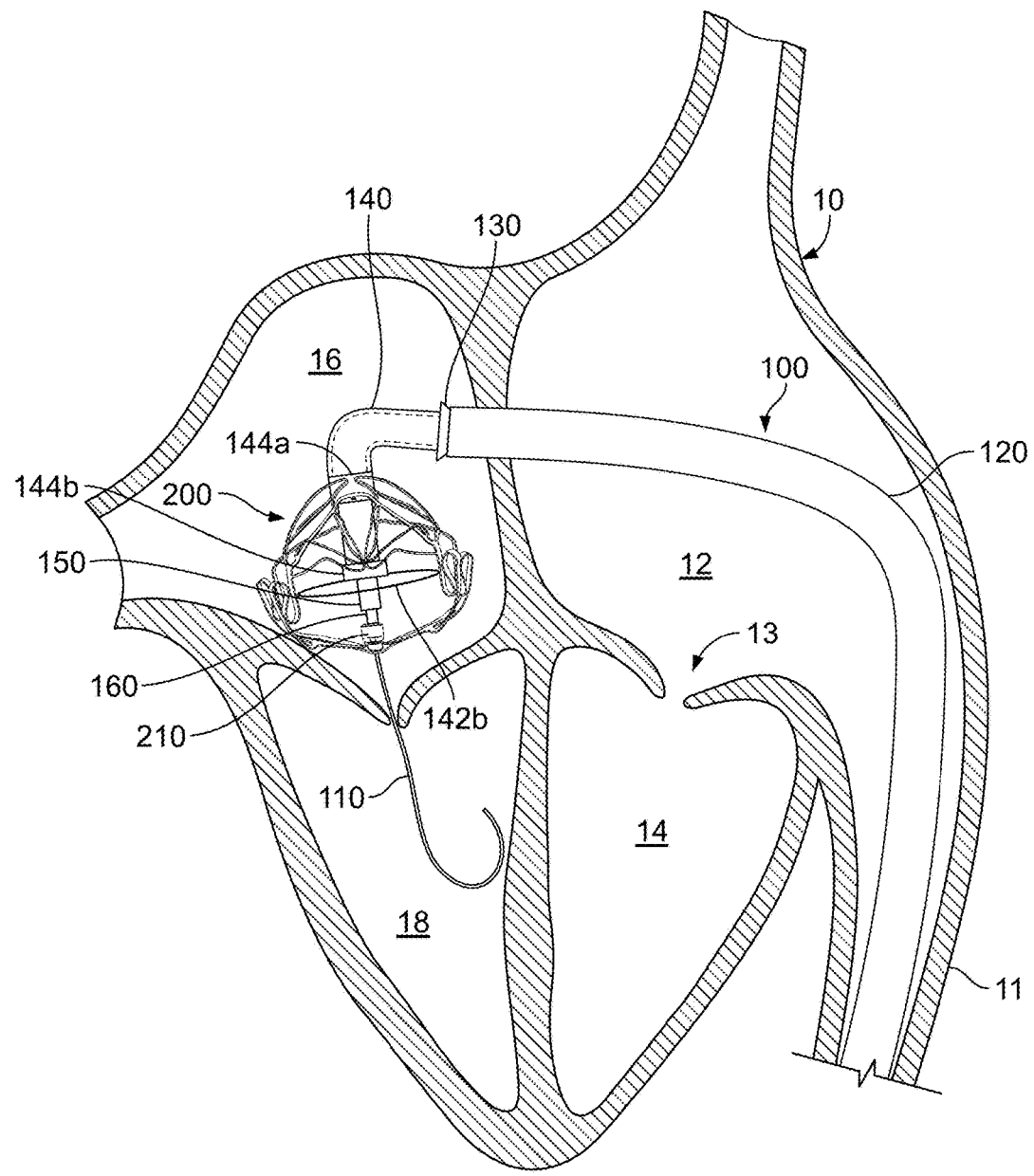
FIG. 5 shows a perspective view of the anchor assembly of FIG. 2 after being rotated/panned in the left atrium so as to orient the anchor assembly axis generally perpendicular to the native mitral valve.

The heart 10 (depicted in cross-section from a posterior perspective in FIG. 1) includes a right atrium 12, a right ventricle 14, a left atrium 16, and a left ventricle 18. A tricuspid valve 13 separates the right atrium 12 from the right ventricle 14. A mitral valve 17 separates the left atrium 16 from the left ventricle 18. An atrial septum 15 separates the right atrium 12 from the left atrium 16. An inferior vena cava 11 is confluent with the right atrium 12. It should be understood that this depiction of the heart 10 is somewhat stylized. The same is true for FIGS. 2 and 5. FIGS. 1, 2 and 5 provide general depictions of the approach to the mitral valve 17 that is used in some implementations. But, the commissural cross-sectional views of FIG. 7 and thereafter more accurately depict the orientation of the prosthetic mitral valves in relation to the heart 10.

Still referring to FIG. 1, in the depicted embodiment, the delivery system 100 includes a guidewire 110, a guide catheter 120, and an anchor delivery sheath 130. Additional components of the delivery system 100 will be described further below. The anchor delivery sheath 130 is slidably (and rotationally) disposed within a lumen of the guide catheter 120. The guidewire 110 is slidably disposed with respect to a lumen of the anchor delivery sheath 130. In this depiction, the anchor delivery sheath 130 has been partially extended relative to the guide catheter 120, allowing an optional flared portion 132 to expand outward, as described further below.

In the depicted implementation, the guidewire 110 is installed into the heart 10 prior to the other components of the delivery system 100. In some embodiments, the guidewire 110 has a diameter of about 0.035 inches (about 0.89 mm). In some embodiments, the guidewire 110 has a diameter in a range of about 0.032 inches to about 0.038 inches (about 0.8 mm to about 0.97 mm). In some embodiments, the guidewire 110 has a diameter smaller than 0.032 inches (about 0.80 mm) or larger than 0.038 inches (about 0.97 mm). In some embodiments, the guidewire 110 is made of materials such as, but not limited to, nitinol, stainless steel, high-tensile-strength stainless steel, and the like, and combinations thereof. The guidewire 110 may include various tip designs (e.g., J-tip, straight tip, etc.), tapers, coatings, covers, radiopaque (RO) markers, and other features. In some embodiments, the guidewire 110 has one or more portions with differing lateral stiffnesses, column strengths, lubricity, and/or other physical properties in comparison to other portions of the guidewire 110.

In some implementations, the guidewire 110 is percutaneously inserted into a femoral vein of the patient. The guidewire 110 is routed to the inferior vena cava 11 and into the right atrium 12. After creating an opening in the atrial septum 15 (e.g., a trans-septal puncture of the fossa ovalis or other portion of the atrial septum), the guidewire 110 is routed into the left atrium 16, and then into the left ventricle 18.

In the depicted implementation, the guide catheter 120 is installed (e.g., via the groin incision 2, refer to FIG. 43) by pushing it (and other components of delivery system 100) over the guidewire 110. In some implementations, a dilator tip is used in conjunction with the guide catheter 120 as the guide catheter 120 is advanced over the guidewire 110. Alternatively, a balloon catheter could be used as the initial dilation means. After the distal end of the guide catheter 120 reaches the left atrium 16, the dilator tip can be withdrawn.

In some embodiments, in order to navigate the guidewire 110 from the left atrium 16 to the left ventricle 18, a catheter with a curved distal tip portion (not shown) is installed over the guidewire 110 within the guide catheter 120. Also, a balloon-tipped catheter (not shown) can be installed over the guidewire 110 within the catheter with the curved distal tip portion. The curved distal tip portion of the catheter can be used to direct the balloon-tipped catheter into the left ventricle 18 (through the mitral valve 17). Such a balloon-tipped catheter can be used advantageously to avoid chordal entanglement as it is advanced through the mitral valve 17. Thereafter, the guidewire 110 can be advanced through the balloon-tipped catheter and into the left ventricle 18. In some implementations, the guidewire 110 can be installed into the heart 10 along other anatomical pathways. The guidewire 110 thereafter serves as a rail over which other components of the delivery system 100 are passed.

By making various adjustments at the proximal end of the guide catheter 120 (as described further below), a clinician can attain a desirable orientation of the guide catheter 120 in relation to the heart 10. For example, the guide catheter 120 can be rotated about its longitudinal axis so that the longitudinal axis of the distal-most tip portion of the guide catheter 120 is pointing toward the perpendicular axis of the mitral valve 17. Such rotational movement of the guide catheter 120 can be performed by the clinician using the deployment system. In addition, in some embodiments a distal end portion of the guide catheter 120 is steerable (also referred to herein as "deflectable"). Using such steering, the distal end portion of the guide catheter 120 can be deflected to navigate the patient's anatomy and/or to be positioned in relation to the patient's anatomy as desired. For example, the guide catheter 120 can be angled within the right atrium 12 to navigate the guide catheter 120 from the inferior vena cava 11 to the atrial septum 15. Accordingly, in some embodiments the guide catheter 120 may include at least one deflection zone 122. As described further below, a clinician can controllably deflect the deflection zone of the guide catheter 120 as desired.

After the guide catheter 120 is oriented within the heart 10 as desired by the clinician, in some embodiments the clinician can releasably lock the guide catheter 120 in the desired orientation. For example, in some embodiments the clinician can releasably lock the guide catheter 120 to a deployment system that is stationary in relation to the patient.

Still referring to FIG. 1, in some embodiments the guide catheter 120 has an outer diameter of about 28 Fr (about 9.3 mm), or about 30 Fr (about 10.0 mm). In some embodiments, the guide catheter 120 has an outer diameter in the range of about 26 Fr to about 34 Fr (about 8.7 mm to about 11.3 mm). In some embodiments, the guide catheter 120 has an outer diameter in the range of about 20 Fr to about 28 Fr (about 6.7 mm to about 9.3 mm).

The guide catheter 120 can comprise a tubular polymeric or metallic material. For example, in some embodiments the guide catheter 120 can be made from polymeric materials such as, but not limited to, polytetrafluoroethylene (PTFE), fluorinated ethylene propylene (FEP), HYTREL®, nylon, PICOFLEX®, PEBAX®, TECOFLEX®, and the like, and combinations thereof. In alternative embodiments, the guide catheter 120 can be made from metallic materials such as, but not limited to, nitinol, stainless steel, stainless steel alloys, titanium, titanium alloys, and the like, and combinations thereof. In some embodiments, the guide catheter 120 can be made from combinations of such polymeric and metallic materials (e.g., polymer layers with metal braid, coil reinforcement, stiffening members, and the like, and combinations thereof). In some embodiments, the guide catheter 120 can comprise a slotted tube.

The example delivery system 100 also includes the anchor delivery sheath 130. In some implementations, after the guide catheter 120 is positioned with its distal end in the left atrium 16, the anchor delivery sheath 130 is installed into a lumen of the guide catheter 120 (over the guidewire 110) and advanced through the guide catheter 120. As described further below, in some embodiments the anchor delivery sheath 130 is preloaded with a prosthetic valve anchor assembly and other components of the delivery system 100.

In some embodiments, the anchor delivery sheath 130 can be made from the materials described above in reference to the guide catheter 120. In some embodiments, the anchor delivery sheath 130 has an outer diameter in the range of about 20 Fr to about 28 Fr (about 6.7 mm to about 9.3 mm). In some embodiments, the anchor delivery sheath 130 has an outer diameter in the range of about 14 Fr to about 24 Fr (about 4.7 mm to about 8.0 mm).

In the depicted embodiment, the anchor delivery sheath 130 includes a flared distal end portion 132. In some embodiments, an inverted-flare distal end portion is included. In some embodiments, no such flared distal end portion 132 is included. The flared distal end portion 132 can collapse to a lower profile when constrained within the guide catheter 120. When the flared distal end portion 132 is expressed from the guide catheter 120, the flared distal end portion 132 can self-expand to the flared shape. In some embodiments, the material of the flared distal end portion 132 includes pleats or folds, may be a continuous flared end or may be separated into sections resembling flower petals, and may include one or more resilient elements that bias the flared distal end portion 132 to assume the flared configuration in the absence of restraining forces (such as from containment within the guide catheter 120). The flared distal end portion 132 can be advantageous, for example, for recapturing (if desired) the anchor assembly within the lumen of the anchor delivery sheath 130 after the anchor assembly has been expressed from the flared distal end portion 132. In some embodiments, a distal-most portion of the flared distal end portion 132 is everted (which can serve to help facilitate recapture of the anchor delivery sheath 130). In some cases, the recapture of the anchor assembly will cause a portion of the flared distal end portion 132 to become everted.

In some embodiments, the maximum outer diameter of the flared distal end portion 132 is in a range of about 30 Fr to about 34 Fr (about 10.0 mm to about 11.3 mm). In some embodiments, the maximum outer diameter of the flared distal end portion 132 is in a range of about 32 Fr to about 44 Fr (about 10.7 mm to about 14.7 mm). In some embodiments, the maximum outer diameter of the flared distal end portion 132 is in a range of about 24 Fr to about 30 Fr (about 8.0 mm to about 10.0 mm). In some embodiments, the maximum outer diameter of the flared distal end portion 132 is less than about 24 Fr (about 8.0 mm) or greater than about 44 Fr (about 14.7 mm).

Referring to FIG. 2, additional components of the example delivery system 100 can include an anchor delivery catheter 140, a secondary steerable catheter 150, and an inner catheter 160. The anchor delivery catheter 140 is slidably disposed within a lumen of the anchor delivery sheath 130. The secondary steerable catheter 150 is slidably disposed within a lumen of the anchor delivery catheter 140. The inner catheter 160 is slidably disposed within a lumen of the secondary steerable catheter 150. The guidewire 110 is slidably disposed within a lumen of the inner catheter 160.

An anchor assembly 200 (shown without covering materials for enhanced visibility) is releasably attached to the inner catheter 160 and is, in effect, slidably disposed on the guidewire 110. As described further below, the components of the delivery system 100 can be individually or jointly manipulated by a clinician operator to control the position and orientation of the anchor assembly 200 during the deployment of the anchor assembly 200. In some embodiments, the inner catheter 160 has a filar construct to advantageously configure the inner catheter 160 to transmit torsion forces. In some implementations, a deployment frame system (such as the example deployment frame system in FIG. 43 described below) is used to initiate and/or control the movements of various components of the transcatheter delivery system 100.

In a preferred implementation of delivery system 100, the anchor delivery catheter 140, the secondary steerable catheter 150, the inner catheter 160, and the anchor assembly 200 are loaded into the anchor delivery sheath 130 prior to the advancement of the anchor delivery sheath 130 into the guide catheter 120 as shown in FIG. 1. That is, in a preferred implementation the anchor delivery catheter 140, the secondary steerable catheter 150, the inner catheter 160, and/or the anchor assembly 200 are already installed in the anchor delivery sheath 130 as the anchor delivery sheath 130 is distally advanced into the guide catheter 120 to attain the arrangement shown in FIG. 1. Then the anchor delivery sheath 130 is individually pulled back (proximally) to reveal the anchor delivery catheter 140, the secondary steerable catheter 150, the inner catheter 160, and/or the anchor assembly 200 as shown in FIG. 2. The anchor assembly 200 may also be at least partially expanded. In some such implementations, the anchor delivery catheter 140, the secondary steerable catheter 150, the inner catheter 160, and/or the anchor assembly 200 are loaded into the anchor delivery sheath 130 in desired relative rotational orientations (i.e., rotational orientations about the longitudinal axis of the delivery system 100). In other implementations, one or more of the anchor delivery catheter 140, the secondary steerable catheter 150, the inner catheter 160, and the anchor assembly 200 are distally advanced into the anchor delivery sheath 130 after the anchor delivery sheath 130 has been advanced into the guide catheter 120 to attain the arrangement shown in FIG. 1.

The inner catheter 160 is releasably coupled with a hub 210 of the anchor assembly 200. In some such embodiments, the inner catheter 160 has a threaded distal tip portion 162 (FIG. 3) that threadably engages with a complementary threaded portion of the hub 210. In some embodiments, as described further below, the inner catheter 160 is also releasably coupled with a SAM containment member 212 (refer, for example, to FIGS. 8 and 19) of the anchor assembly 200. For example, in some embodiments the threaded distal tip portion 162 of the inner catheter 160 is threadably engaged with a complementary threaded eyelet 214 (e.g., FIGS. 16 and 17) of the SAM containment member 212. When a clinician operator desires to uncouple the inner catheter 160 from the SAM containment member 212 and/or the hub 210, the clinician can apply a torque to the inner catheter 160 to unscrew the threaded distal tip portion 162 from the eyelet 214 and/or the hub 210. In some embodiments, the inner catheter 160 is a filar construct so as to configure the inner catheter 160 to transmit a torque to facilitate uncoupling the inner catheter 160 from the SAM containment member 212 and/or the hub 210. In some embodiments, other types of mechanisms are used to releasably couple the delivery system 100 to one or more portions of the anchor assembly 200.

One or more portions of the anchor assembly 200 can also be releasably coupled to one or more catheters of the delivery system 100 by one or more control wires. The one or more control wires can be used to control the anchor assembly 200 (e.g., to control the configuration of the anchor assembly 200). For example, the one or more control wires can be used for controlling the diametrical expansion of a self-expanding anchor assembly 200 and/or for controlling the deployment of particular features of the anchor assembly 200. In the depicted embodiment, a proximal portion of the anchor assembly 200 is releasably coupled to the anchor delivery catheter 140 by a proximal control wire 142a, and a mid-body portion of the anchor assembly 200 is releasably coupled to the anchor delivery catheter 140 by a mid-body control wire 142b.

Figure 3:
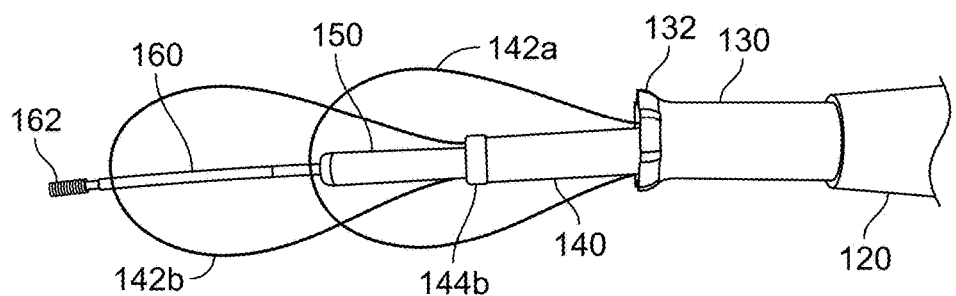
FIG. 3 shows a distal end portion of some components of the deployment system of FIG. 1, including two wires for controlling the diametric expansion of the anchor assembly of FIG. 2.
Figure 4:
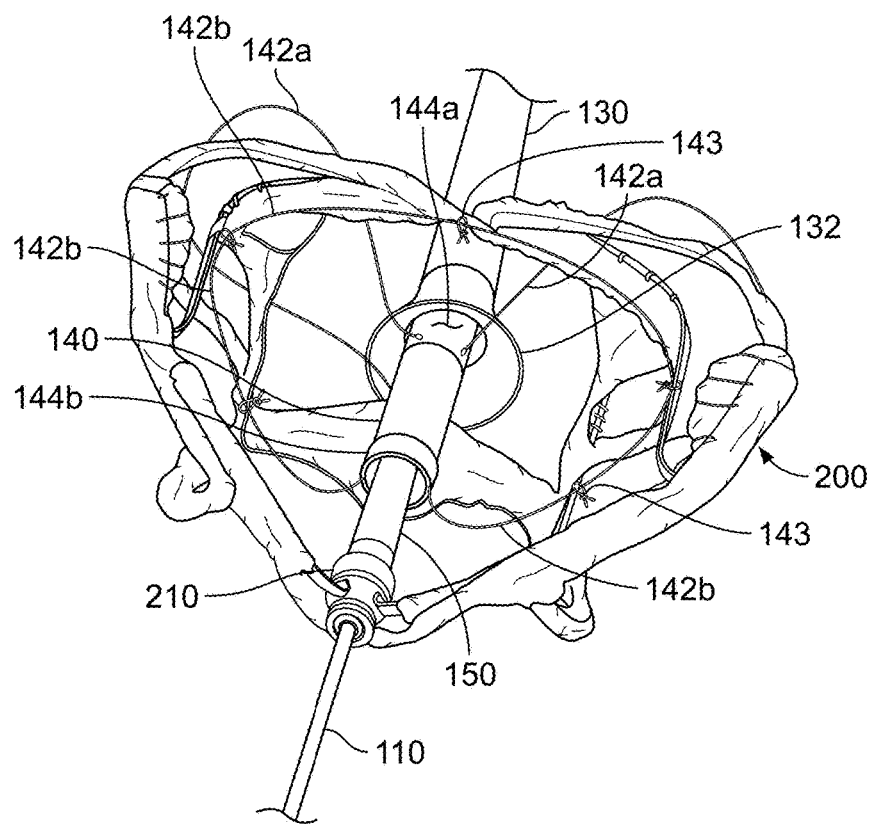
FIG. 4 shows a perspective view of the distal end portion of the deployment system as shown in FIG. 3 in engagement with the anchor assembly of FIG. 2.

Referring also to FIGS. 3 and 4, in the depicted embodiment the proximal control wire 142a emerges from and reenters into the anchor delivery catheter 140 at a proximal collar 144a that is integral with the anchor delivery catheter 140, and the distal control wire 142b emerges from and reenters into the anchor delivery catheter 140 at a distal collar 144b that is integral with the anchor delivery catheter 140. In some embodiments, the control wires 142a and 142b pass through lumens in the wall of the anchor delivery catheter 140, and travel proximally to the deployment control system (e.g., the example deployment frame system shown in FIG. 43). The two ends of each of the control wires 142a and 142b can be terminated at the deployment control system. At such a deployment control system, the tension on the control wires 142a and 142b can be manipulated by a clinician to control the configuration of the anchor assembly 200. In this example, by tightening the control wires 142a and/or 142b, the anchor assembly 200 will be diametrically contracted, and by loosening the control wires 142a and/or 142b, the anchor assembly 200 will be permitted to diametrically self-expand (for example, so that each control wire 142a and 142b can be operated somewhat similar to an adjustable lasso to control expansion of different portions of the anchor assembly at different stages). When the clinician is satisfied with the deployment orientation of the anchor assembly 200, the control wires 142a and 142b can be decoupled from the anchor assembly 200 by the clinician. To do so, the clinician can release one end of the control wire 142a and/or 142b and pull on the other end so that the control wire 142a and/or 142b becomes disengaged with the anchor assembly 200.

FIG. 4 shows how the control wires 142a and 142b can be releasably coupled with the anchor assembly 200 in some embodiments. It should be understood that this is merely one exemplary control wire coupling arrangement and various other arrangements for coupling one or more control wires to the anchor assembly 200 are also envisioned within the scope of this disclosure. Various types of attachment elements can be used to releasably couple the control wires 142a and 142b to the anchor assembly 200. In the depicted embodiment, suture loops 143 are used as the attachment elements. The suture loops 143 can be constructed of materials such as, but not limited to, ultra-high molecular weight polyethylene, nylon, polypropylene, polybutester, and the like. In some embodiments, two suture loops 143 are used in each location to provide redundancy. The suture loops 143 may be coupled with eyelets on the anchor assembly 200 in some cases. In some embodiments, other types of attachment elements such as, but not limited to, eyelets, grommets, rings, clips, pins, fabric portions, and/or the like, are used as attachment elements.

In the depicted embodiment, the proximal control wire 142a is releasably coupled with attachment elements associated with structural features located at the proximal end of the anchor assembly 200. For example, the proximal control wire 142a is releasably coupled with attachment elements of three arched atrial holding features 240a, 240b, and 240c (e.g., refer to FIGS. 18-21) and three frame lobes 250a, 250b, and 250c (e.g., refer to FIGS. 18-21) of the anchor assembly 200. That is, the proximal control wire 142a emerges from the anchor delivery catheter 140 at the proximal collar 144a, passes through the attachment elements of the three arched atrial holding features 240a, 240b, and 240c, and the three frame lobes 250a, 250b, and 250c, and reenters the anchor delivery catheter 140 at the proximal collar 144a. By applying tension to the proximal control wire 142a, the three arched atrial holding features 240a, 240b, and 240c, and the three frame lobes 250a, 250b, and 250c can be diametrically drawn inward towards the anchor delivery catheter 140. In the arrangement depicted in FIG. 2, for example, the three arched atrial holding features 240a, 240b, and 240c, and the three frame lobes 250a, 250b, and 250c are drawn in very closely to the anchor delivery catheter 140.

In the depicted embodiment, the mid-body control wire 142b is releasably coupled with attachment elements associated with structural features of the anchor assembly 200 located at the longitudinal middle region of the anchor assembly 200. For example, the mid-body control wire 142b is releasably coupled with attachment elements of four inter-annular connections 270a, 270b, 270c, and 270d (e.g., refer to FIGS. 18-21) and a mid-body portion of the supra-annular ring 250 of the anchor assembly 200. That is, the mid-body control wire 142b emerges from the anchor delivery catheter 140 at the distal collar 144b, passes through the attachment elements of the four inter-annular connections 270a, 270b, 270c, and 270d, and the mid-body portion of the supra-annular ring 250, and reenters the anchor delivery catheter 140 at the distal collar 144b. By applying tension to the mid-body control wire 142b, the four inter-annular connections 270a, 270b, 270c, and 270d, and the mid-body portion of the supra-annular ring 250 can be diametrically drawn inward towards the anchor delivery catheter 140. In the arrangement depicted in FIG. 2, the four inter-annular connections 270a, 270b, 270c, and 270d, and the mid-body portion of the supra-annular ring 250 are drawn in toward the anchor delivery catheter 140 such that the diameter of the anchor assembly 200 is less than the fully expanded diameter.

Diametric control of the anchor assembly 200 by manipulation of the tension of the mid-body control wire 142b can be advantageously utilized by a clinician during the deployment of the anchor assembly 200. For example, as described further below, the steps of advancing the anchor assembly 200 through the annulus of the native mitral valve and seating anchor feet 220a, 220b, 220c, and 220d (e.g., refer to FIGS. 18-21) in the sub-annular gutter 19 (FIG. 12) can be facilitated using the diametric control afforded by the mid-body control wire 142b.

While the depicted embodiment includes two control wires 142a and 142b, in some embodiments one, three, four, five, or more than five control wires are included. A clinician can separately control the two control wires 142a and 142b. For example, in some embodiments the mid-body control wire 142b may be partially or fully loosened while the proximal control wire 142a is maintained in a state of full tension. In some implementations, a deployment frame system (such as the example deployment frame system of FIG. 43 described below) is used to control the tension and movements of the two control wires 142a and 142b.

Still referring to FIG. 2, while the components of the delivery system 100 and the anchor assembly 200 are depicted in particular relative orientations and arrangements, it should be understood that the depictions are non-limiting. For example, in some implementations of the deployment process the distal tip of the secondary deflectable catheter 150 may always be, or may sometimes be, abutted to the hub 210 of the anchor assembly 200. Further, in some implementations of the deployment process the distal tip of the anchor delivery catheter 140 may always be, or may sometimes be, positioned within the interior of the anchor assembly 200. In some implementations, a deployment frame system (such as the example deployment frame system of FIG. 43 described below) is used to control such relative arrangements and movements of the anchor delivery catheter 140 and secondary deflectable catheter 150 in relation to the anchor assembly 200, for example.

In some embodiments, the position of the anchor assembly 200 can be controlled by manipulating the relative positions of the inner catheter 160 and/or the anchor delivery catheter 140. For example, in the depicted embodiment the anchor assembly 200 can be expressed out from the anchor delivery sheath 130 (as shown in FIG. 2) by moving the inner catheter 160 and/or the anchor delivery catheter 140 distally in relation to the anchor delivery sheath 130. In some implementations, the expression of the anchor assembly 200 is caused by proximally pulling back the anchor delivery sheath 130 while generally maintaining the positions of the inner catheter 160 and/or the anchor delivery catheter 140. In some implementations, the expression of the anchor assembly 200 is caused by a combination of proximally pulling back the anchor delivery sheath 130 while distally extending the positions of the inner catheter 160 and/or the anchor delivery catheter 140.

As the anchor assembly 200 emerges from the confines of the anchor delivery sheath 130, the anchor assembly 200 may expand from a low-profile delivery configuration to an at least partially expanded configuration (for example, a partially expanded condition, as shown in FIG. 2, that is less that its fully expanded condition as described in more detail below). In addition to control by manipulation of the mid-body control wire 142b, the extent of expansion of the anchor assembly 200 can also be at least partially controlled by the relative positioning of the anchor delivery catheter 140 in relation to the inner catheter 160. For instance, as the anchor delivery catheter 140 is moved proximally in relation to the inner catheter 160, the anchor assembly 200 is axially elongated and radially contracted. Conversely, as the anchor delivery catheter 140 is moved distally in relation to the inner catheter 160, the anchor assembly 200 is axially shortened and radially expanded. In some implementations, this control of the radial size of the anchor assembly 200 is used by a clinician during the process of deploying the anchor assembly 200 within the native mitral valve 17, as described further below. As described above, the one or more control wires 142a and 142b can also be used to control diametrical expansion of the anchor assembly 200 (without changing the relative distance of the anchor delivery catheter 140 in relation to the inner catheter 160).

Figure 37:
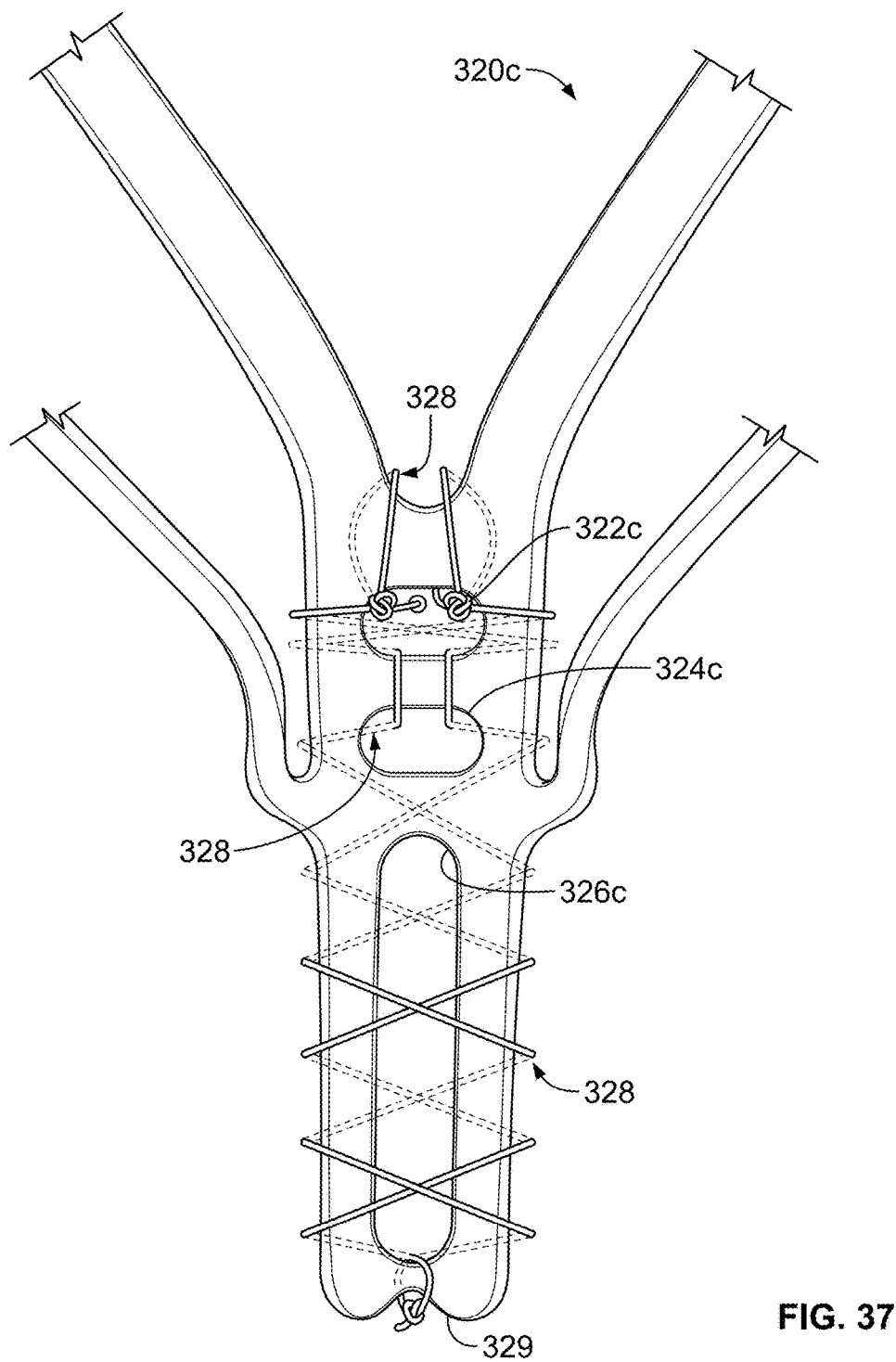
FIG. 37 shows an enlarged view of a portion of a commissural post of the valve assembly of FIGS. 26-30 and an example leaflet attachment stitching pattern, in accordance with some embodiments.

It should be understood that the prosthetic mitral valves provided herein are comprised of an anchor assembly 200 and a separate valve assembly (e.g., refer to FIG. 37). The anchor assembly 200 is deployed to an arrangement interfacing within the native mitral valve 17 prior to deployment of the valve assembly. Said differently, after implanting the anchor assembly 200 within the native mitral valve 17, the valve assembly can then be deployed within the anchor assembly 200 and within the native mitral valve 17 (as described further below). Therefore, it can be said that the prosthetic mitral valves provided herein are deployed using a staged implantation method. That is, the anchor assembly 200 is deployed in one stage, and the valve assembly is deployed in a subsequent stage. In some embodiments, as described further below, the SAM containment member 212 is also deployed as part of the deployment method. In some implementations, the deployment of the valve assembly takes place right after the deployment of the anchor assembly 200 (e.g., during the same medical procedure). In some implementations, the deployment of the valve assembly takes place hours, days, weeks, or even months after the deployment of the anchor assembly 200 (e.g., during a subsequent medical procedure).

The staged implantation method of the prosthetic mitral valves provided herein is facilitated by the fact that when the anchor assembly 200 itself is implanted within the native mitral valve 17, the native mitral valve 17 continues to function essentially as before the implantation of the anchor assembly 200 without a significant impact on cardiovascular physiology. That is the case because, as described further below, the anchor assembly 200 interfaces and anchors within structural aspects of the native mitral valve 17 without substantially interfering with the leaflets or chordae tendineae of the native mitral valve 17.

Still referring to FIG. 2, in the depicted arrangement the distal end portion of the secondary steerable catheter 150 is located at least partially internally within the anchor assembly 200. The secondary steerable catheter 150 can be manipulated by a clinician operator to reversibly bend (deflect) the distal end portion of the secondary steerable catheter 150. As the secondary steerable catheter 150 is bent by the clinician, other components of the delivery system 100 may deflect along with the secondary steerable catheter 150. For example, portions of one or more of the inner catheter 160 and the anchor delivery catheter 140 may bend in response to the bending of the deflectable catheter 150. Because the anchor assembly 200 is coupled to the inner catheter 160 and the anchor delivery catheter 140, the anchor assembly 200 can, in turn, be pivoted or "panned" by bending the secondary steerable catheter 150.

Referring to FIG. 5, as described above, in some embodiments the secondary steerable catheter 150 can be articulated (also referred to as "steered," "deflected," "bent," "curved," and the like) to orient the anchor assembly 200 in relation to the mitral valve 17 as desired. That is, in some embodiments the secondary steerable catheter 150 has one or more deflection zones at a distal end portion of the secondary steerable catheter 150. For example, in the depicted embodiment the secondary steerable catheter 150 has two deflection zones 152 and 154 (refer to FIG. 7) at the distal end portion of the secondary steerable catheter 150. In some embodiments, the two deflection zones 152 and 154 allow for deflection of the distal end portion of the secondary steerable catheter 150 within two separate and distinct planes. For example, in the depicted embodiment deflection zone 152 allows for deflection of the distal end portion of the secondary steerable catheter 150 generally within the plane of FIGS. 1, 2, and 5, while deflection zone 154 allows for deflection of the distal end portion of the secondary steerable catheter 150 generally orthogonal to the plane of FIGS. 1, 2, and 5. In some implementations, a deployment frame system (such as the example deployment frame system of FIG. 43 described below) is used to initiate and control such deflection of the secondary steerable catheter 150, including deflection of the distal end portion of the secondary steerable catheter 150 within two separate and distinct planes, individually.

In some implementations, it is desirable to orient (e.g., laterally pivot, pan, etc.) the anchor assembly 200 within the atrium 16 so that the longitudinal axis of the anchor assembly 200 is generally perpendicular to the native mitral valve 17, and coaxial with the native mitral valve 17 (e.g., to center the anchor assembly 200 with the line or coaptation of the mitral valve 17). The orienting of the partially or fully expanded anchor assembly 200 within the atrium 16 may be advantageous versus having to orient the anchor assembly 200 while it is still constrained within a delivery sheath, as the latter assembly is a relatively large and stiff catheter assembly.

In some implementations, the anchor assembly 200 within the atrium 16 can be additionally, or alternatively, oriented in relation to the native mitral valve 17 by rotating the guide catheter 120 about its longitudinal axis. Such a rotation of the guide catheter 120 about its longitudinal axis can result in a directional adjustment of the longitudinal axis of the distal tip portion of the guide catheter 120. That is, rotation of the guide catheter 120 about its longitudinal axis can result in pointing the distal tip portion of the guide catheter 120 (and the components of the delivery system 100) in a desired direction within the atrium 16. In some implementations, a deployment frame system is used to initiate and control such rotation of the guide catheter 120 about its longitudinal axis.

In some implementations, the relative rotational alignment of the anchor assembly 200 in relation to the mitral valve 17 can be adjusted as desired in preparation for engaging the anchor assembly 200 with the native mitral valve 17. For example, in some implementations the anchor assembly 200 can be rotated about its longitudinal axis by rotating the inner catheter 160 and the anchor delivery catheter 140 generally in unison, while keeping the secondary steerable catheter 150 essentially stationary. In some implementations, a deployment frame system (such as the example deployment frame systems described below) is used to initiate and control such rotation of the anchor assembly 200 about its longitudinal axis.

In preparation for engaging the anchor assembly 200 with the native mitral valve 17, the clinician operator may manipulate the radial size of the anchor frame 200 so that the anchor frame 200 can be passed through the native mitral valve 17 without damaging the native mitral valve 17. For example, the clinician can diametrically expand or retract one or more portions of the anchor assembly 200 by manipulation of the mid-body control wire 142b. Alternatively, or additionally, the clinician can move the anchor delivery catheter 140 proximally in relation to the inner catheter 160 to radially contract the anchor assembly 200. With the anchor assembly 200 configured in a desired diametrical size, and appropriately aligned with the mitral valve 17, the anchor frame 200 can be safely passed through the native mitral valve 17 without damaging the native mitral valve 17 and/or entangling chordae tendineae of the mitral valve 17. Moreover, by controlling the diametrical size of the anchor assembly 200 to just slightly less than the size of the annulus of the mitral valve 17, an advantageous natural centering of the anchor assembly 200 can occur as the sub-annular portions of the anchor assembly 200 are advanced through the mitral valve 17.

Figure 7:
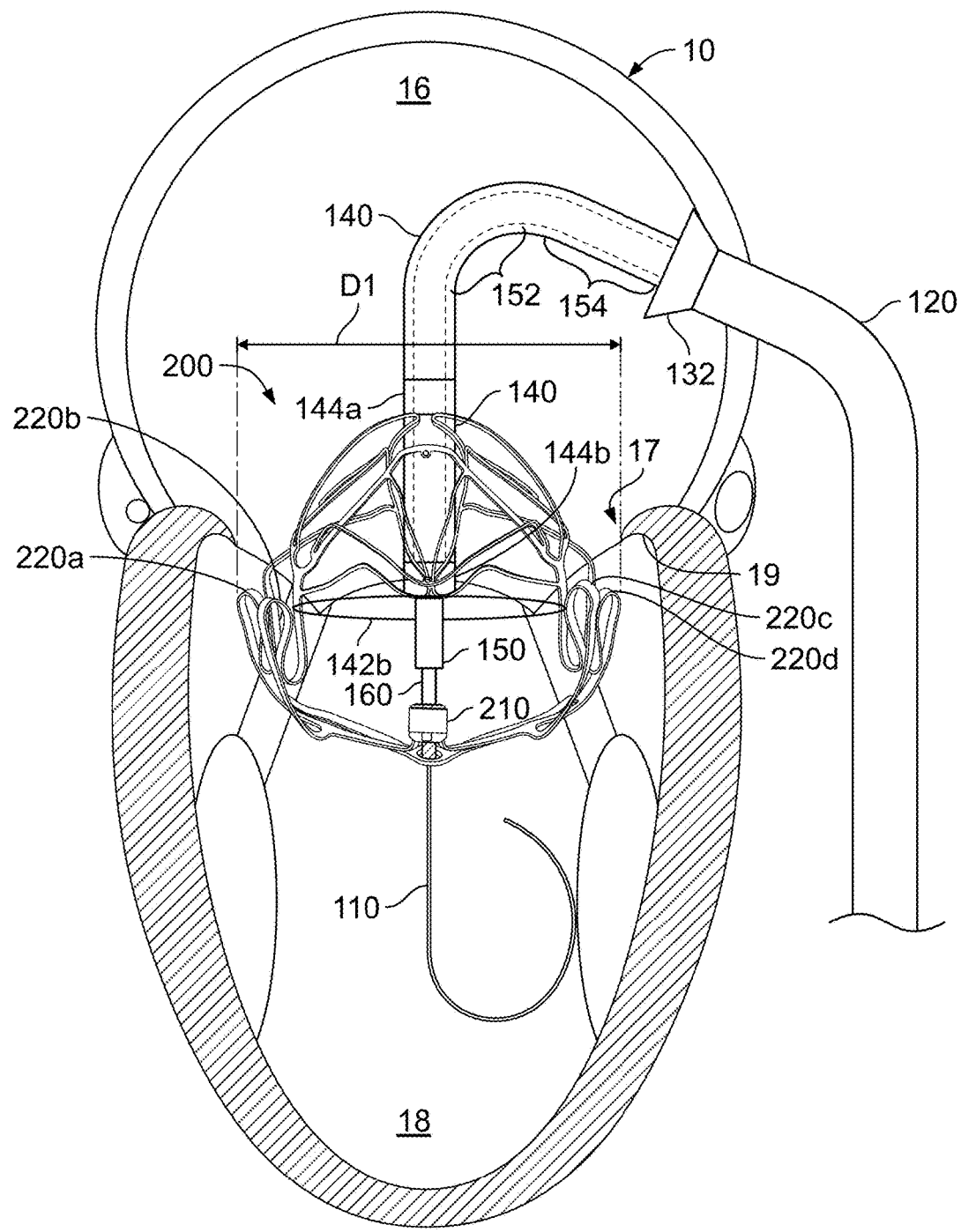
FIG. 7 shows a perspective view in a commissural cross-sectional view of the heart (from the left side of the heart) of the anchor assembly of FIG. 2 after being partially advanced through the native mitral valve so as to position projections of the anchor assembly below an annulus of the native mitral valve.

Referring to FIG. 7, a commissural cross-sectional view of the heart 10 provides another perspective of the anchor assembly 200 in relation to the native mitral valve 17. This commissural cross-sectional view of the heart 10 is a cross-sectional view taken through the mitral valve 17 along a plane through the left atrium 16 and left ventricle 18 that is parallel to the line that intersects the two commissures of the mitral valve. In the following FIGS. 8-11 and 25-30, the commissural cross-sectional view of the heart 10 will be used to describe the delivery system 100 and methods for deploying the prosthetic mitral valves provided herein. The view in FIGS. 7-11 and 25-30 is slightly tilted so that better visualization of the anchor assembly 200 is provided.

While the secondary steerable catheter 150 is retained in its bent (deflected) configuration as described in reference to FIG. 5, the inner catheter 160 and the anchor delivery catheter 140 can be simultaneously advanced. Because the inner catheter 160 is releasably coupled to the hub 210 of the anchor assembly 200, and because the anchor delivery catheter 140 is releasably coupled to the proximal end and the mid-body region of the anchor assembly 200 via the control wires 142a and 142b, generally simultaneous advancement of the inner catheter 160 and the anchor delivery catheter 140 results in advancement of the anchor assembly 200.

In preparation for the advancement of the distal portions of the anchor assembly 200 through the annulus of the mitral valve 17, the mid-body control wire 142b can be manipulated to adjust a mid-body diameter D1 of the anchor assembly 200 to a desired size. For example, in some implementations it is desirable to adjust the mid-body diameter D1 to size that is slightly smaller than the size of the annulus of the mitral valve 17. In such a case, while advancing the distal portions of the anchor assembly 200 through the annulus of the mitral valve 17, a self-centering of the anchor assembly 200 in relation to the mitral valve 17 may naturally occur.

As depicted, the anchor assembly 200 is advanced such that the distal end portions of anchor assembly 200 are positioned within the left ventricle 18 while the proximal end portions of the anchor assembly 200 remain positioned within the left atrium 16. Hence, some portions of the anchor assembly 200 are on each side of the native mitral valve 17. Said differently, the deployed anchor assembly 200 includes supra-annular portions and sub-annular portions.

In the depicted embodiment, the anchor assembly 200 includes four anchor feet: a lateral anterior foot 220a, a lateral posterior foot 220b, a medial posterior foot 220c, and a medial anterior foot 220d (refer also to FIGS. 18-21). In some embodiments, fewer or more anchor feet may be included (e.g., two, three, five, six, or more than six). In some embodiments, the anchor feet 220a, 220b, 220c, and 220d are portions of the anchor assembly 200 that are configured for contact with a sub-annular gutter 19 (also refer to FIG. 12) of the native mitral valve 17, without penetrating tissue of the native mitral valve 17. Accordingly, the anchor feet 220a, 220b, 220c, and 220d have atraumatic surfaces that are generally comparable to feet. However, in some embodiments one or more of the anchor feet 220a, 220b, 220c, and 220d are configured to penetrate tissue and may have anchor features such as barbs, coils, hooks, and the like.

In the arrangement of FIG. 7, the anchor feet 220a, 220b, 220c, and 220d are positioned below the sub-annular gutter 19. In this arrangement then, the mid-body diameter D1 of the anchor assembly 200 can thereafter be increased to align the anchor feet 220a, 220b, 220c, and 220d with the sub-annular gutter 19. For example, in some embodiments the mid-body control wire 142b positioned on or around the mid-body portion of the anchor assembly 200 can be manipulated (e.g., slackened) to allow radial self-expansion of the anchor assembly 200, to align the anchor feet 220a, 220b, 220c, and 220d with the sub-annular gutter 19. Alternatively, or additionally, in some embodiments the clinician can move the anchor delivery catheter 140 distally in relation to the inner catheter 160 to radially expand the anchor assembly 200 to align the anchor feet 220a, 220b, 220c, and 220d with the sub-annular gutter 19. Such alignment can be performed in preparation for seating the anchor feet 220a, 220b, 220c, and 220d within the sub-annular gutter 19.

Figure 8:
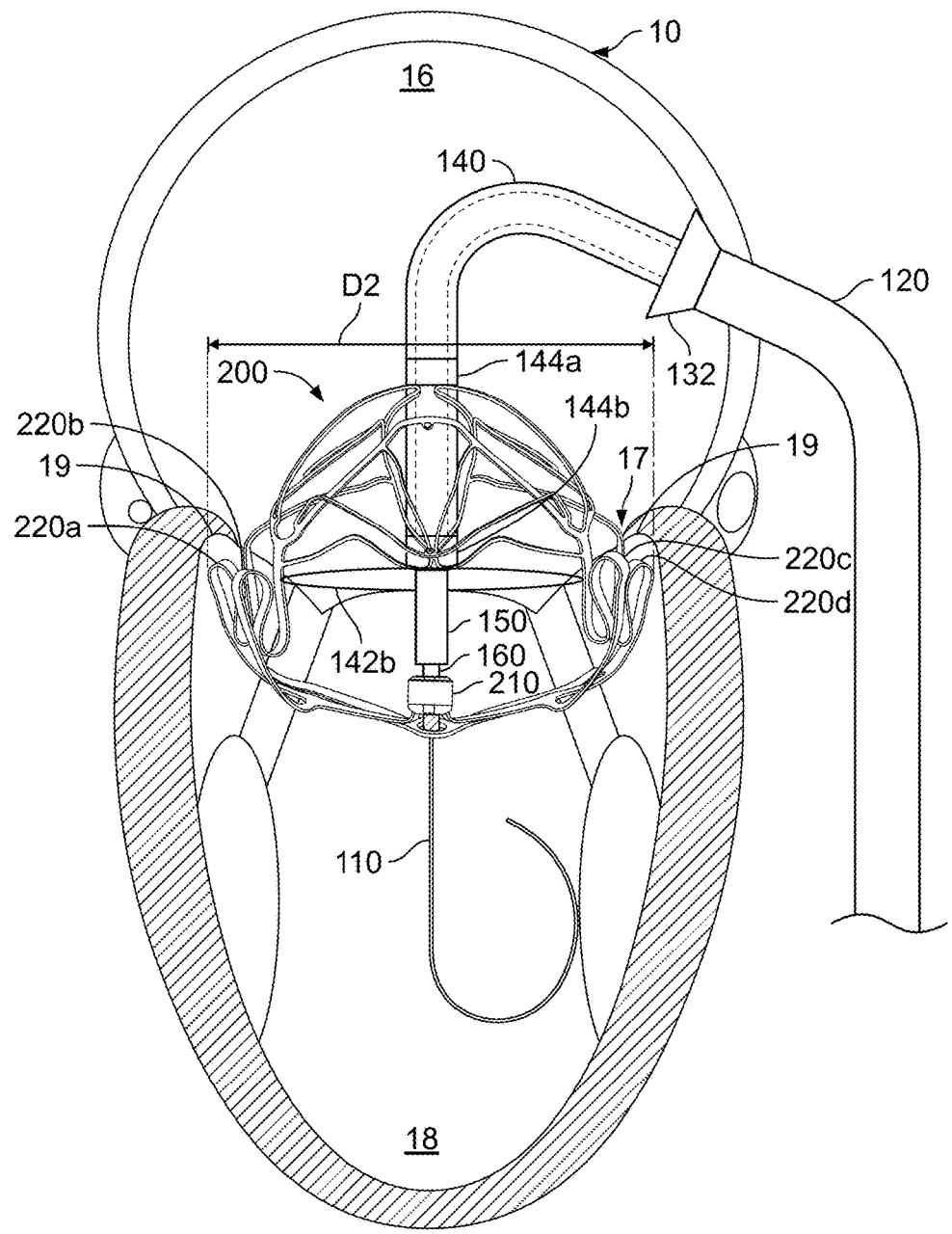
FIG. 8 shows a perspective view of the anchor assembly of FIG. 7 after being diametrically expanded to align the projections of the anchor assembly with a sub-annular gutter of the native mitral valve.

Referring to FIG. 8, the anchor feet 220a, 220b, 220c, and 220d are positioned below the sub-annular gutter 19. In this position, the anchor feet 220a, 220b, 220c, and 220d are positioned under the systolic and diastolic excursions of the leaflets of the native mitral valve 17.

With the anchor feet 220a, 220b, 220c, and 220d positioned below the sub-annular gutter 19, the anchor feet 220a, 220b, 220c, and 220d can be aligned with the sub-annular gutter 19 in preparation for seating the anchor feet 220a, 220b, 220c, and 220d within the sub-annular gutter 19. For example, to align the anchor feet 220a, 220b, 220c, and 220d with the sub-annular gutter 19, in some implementations tension from the mid-body control wire 142b can be relieved by the clinician to allow the mid-body diameter to expand from D1 (FIG. 7) to D2. When the anchor assembly 200 has a mid-body diameter D2, the anchor feet 220a, 220b, 220c, and 220d are posed in diametrical positions for seating within the sub-annular gutter 19.

Figure 9:
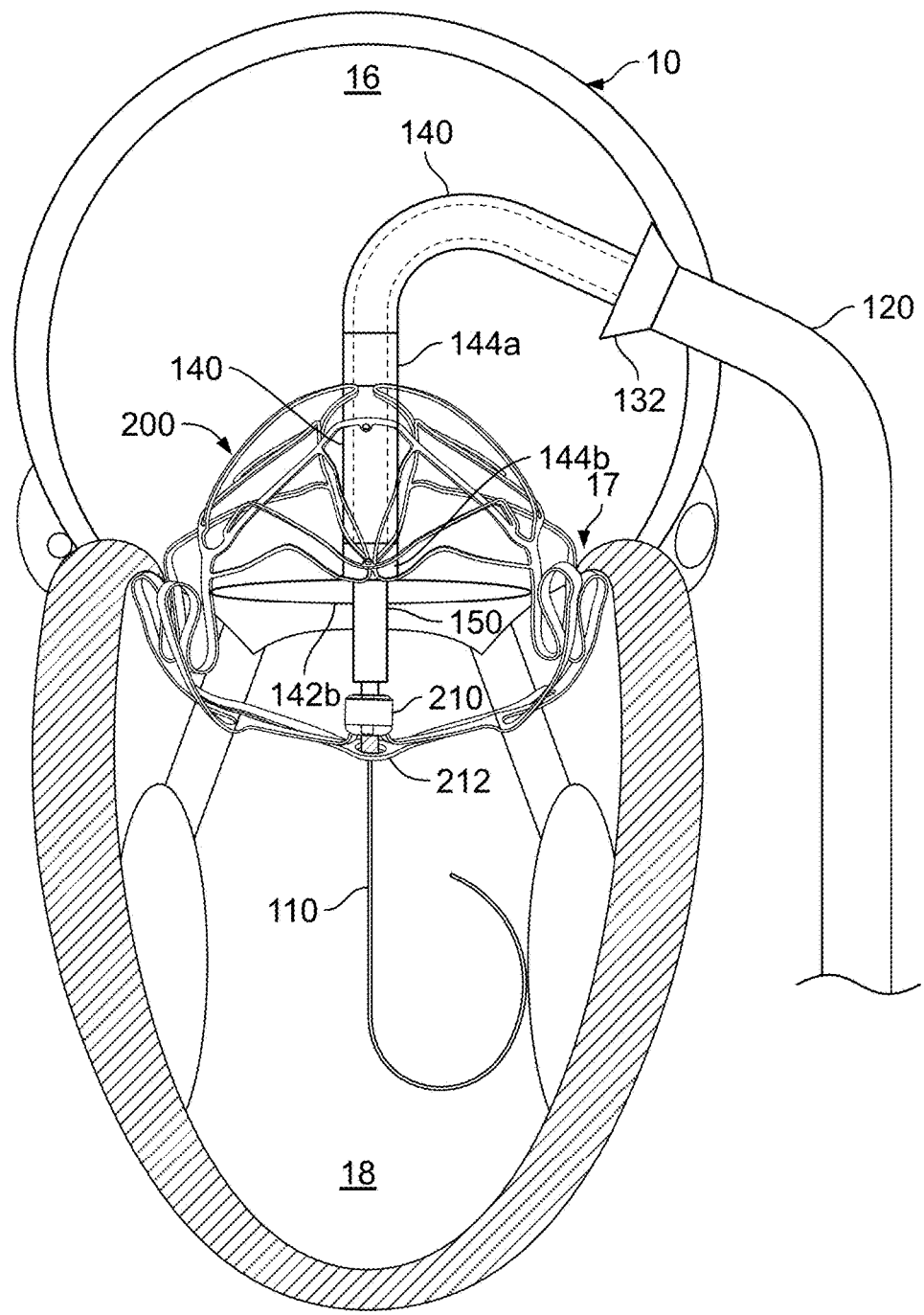
FIG. 9 shows a perspective view of the anchor assembly of FIG. 8 after being retracted so as to position the projections of the anchor assembly in the sub-annular gutter of the native mitral valve.

Referring to FIG. 9, the inner catheter 160 and the anchor delivery catheter 140 can be simultaneously retracted while maintaining the secondary steerable catheter 150 and the guide catheter 120 in fixed positions. As a result, the anchor feet 220a, 220b, 220c, and 220d become seated in the sub-annular gutter 19. As described further below, simultaneous movement of two or more components of the delivery system 100 (e.g., the inner catheter 160 in conjunction with the anchor delivery catheter 140, while maintaining the secondary steerable catheter 150 and the guide catheter 120 in fixed positions) can be initiated and controlled using a deployment frame system (such as the example deployment frame system of FIG. 43 described below).

With the anchor feet 220a, 220b, 220c, and 220d seated in the sub-annular gutter 19, the anchor feet 220a, 220b, 220c, and 220d are positioned under the systolic and diastolic excursions of the leaflets of the native mitral valve 17, and the other structures of the anchor assembly 200 do not inhibit the movements of the leaflets. Therefore, with the anchor assembly 200 coupled to the structures of the mitral valve 17 as described, the mitral valve 17 can continue to function as it did before the placement of the anchor assembly 200. In addition, the manner in which the anchor assembly 200 interfaces with the native mitral valve 17 does not result in deformation of the native mitral valve 17. With the SAM containment member 212 in its pre-deployed configuration, the SAM containment member 212 does not affect the natural function of the native mitral valve 17. Therefore, the native mitral valve 17 can continue to function as it did before the placement of the anchor assembly 200.

Figure 10:
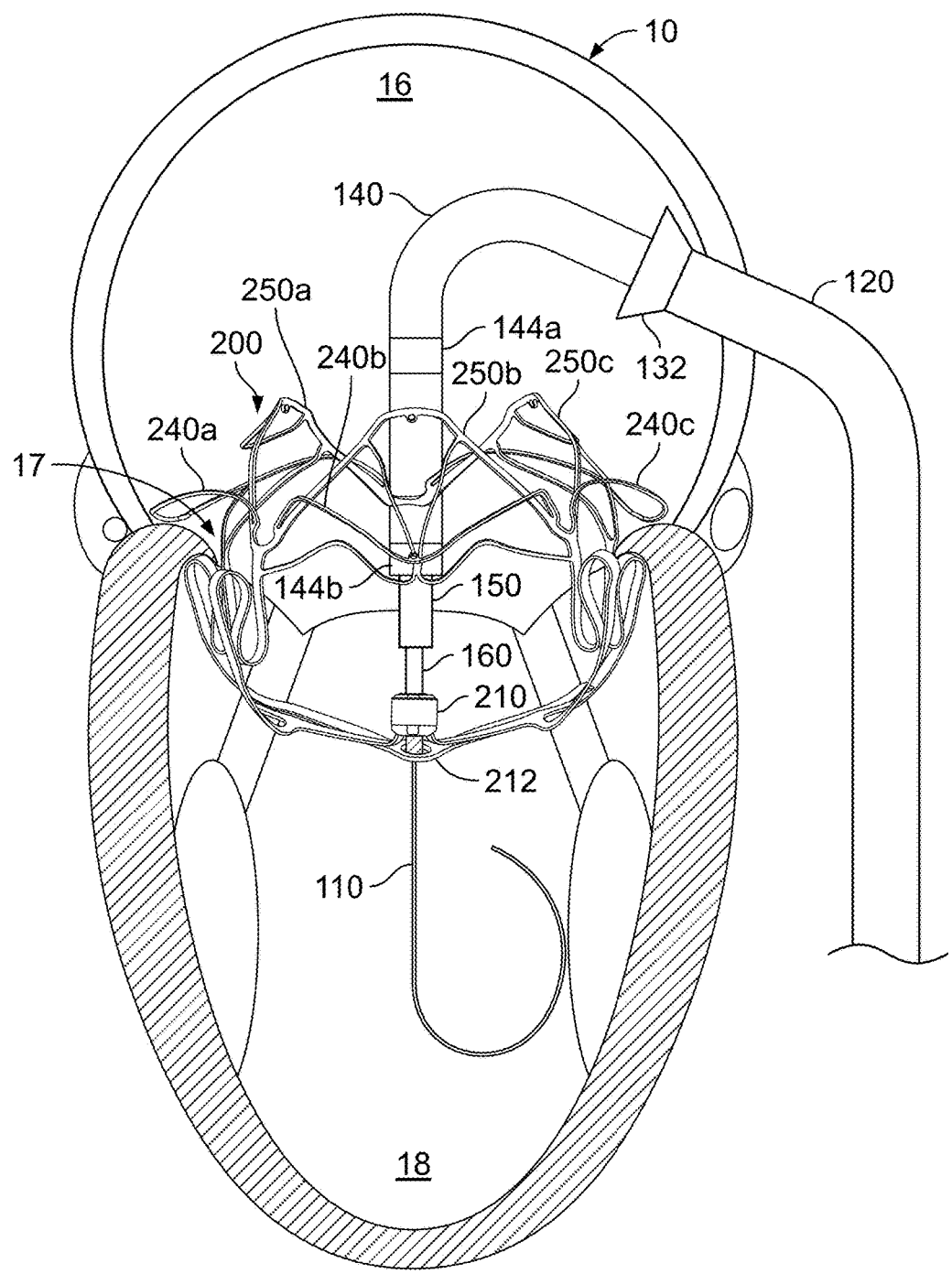
FIG. 10 shows a perspective view of the anchor assembly of FIG. 7 after the release and retraction of the control wires of the deployment system.

Referring to FIG. 10, with the anchor assembly 200 engaged within the native mitral valve 17, components of the delivery system 100 can be uncoupled from the anchor assembly 200. For example, the one or more control wires 142a and 142b (FIGS. 2-5 and 7-9) can be uncoupled from the anchor assembly 200 (e.g., from the mid-body and proximal end portions of the anchor assembly 200 in some embodiments). As described further below, in some embodiments the frame members of the anchor assembly 200 can be made of an elastic or a super-elastic material with shape memory such that portions of the anchor assembly 200 self-expand/deploy to intended orientations in the absence of constraining forces, such as constraining forces from the control wires 142a and/or 142b.

In the depicted embodiment, when the mid-body control wire 142b is uncoupled from the anchor assembly 200, the mid-body regions of the anchor assembly 200 are no longer diametrically constrained by the mid-body control wire 142b. Hence, mid-body regions of the anchor assembly 200 are allowed to diametrically expand when the mid-body control wire 142b is uncoupled from the anchor assembly 200.

When the proximal control wire 142a is loosened and/or detached from one or more proximal end portions of the anchor assembly 200, the one or more portions that were coupled to the proximal control wire 142a become free to expand and deploy to intended orientations in relation to the mitral valve 17. For example, in the depicted embodiment, the proximal control wire 142a was coupled to three arched atrial holding features 240a, 240b, and 240c. When the proximal control wire 142a is uncoupled (e.g., slid out from or "un-lassoed") from the three arched atrial holding features 240a, 240b, and 240c, the three arched atrial holding features 240a, 240b, and 240c are free to deploy to their intended orientations in relation to the mitral valve 17. The three arched atrial holding features 240a, 240b, and 240c deploy generally radially outward (transversely) in relation to the longitudinal axis (the axis extending between the proximal and distal ends of the anchor assembly 200) of the anchor assembly 200. Hence, in the depicted embodiment the three arched atrial holding features 240a, 240b, and 240c self-deploy to respective positions directly adjacent to, or spaced apart just above, the annulus of the mitral valve 17. In those positions, the three arched atrial holding features 240a, 240b, and 240c resist migration of the anchor assembly 200 towards the left ventricle 18.

In addition, in the depicted embodiment when the proximal control wire 142a is loosened and subsequently detached from the three frame lobes 250a, 250b, and 250c, the three frame lobes 250a, 250b, and 250c become free to expand and deploy to intended orientations. In the depicted embodiment the three frame lobes 250a, 250b, and 250c diametrically expand into positions that are designed to interface with a valve assembly that will be deployed into a mating arrangement with the anchor assembly 200 as described further below.

In the depicted arrangement, the anchor assembly 200 is deployed in engagement with the native mitral valve 17. Nevertheless, the native mitral valve 17 is free to function normally. Moreover, in the depicted arrangement, while the inner catheter 160 is still coupled with the anchor assembly 200 at the hub 210, the anchor delivery catheter 140 (and other components of the transcatheter delivery system 100) are no longer attached to the anchor assembly 200. Hence, some components of the transcatheter delivery system 100 that were used to deploy the anchor assembly 200 can now be retracted and removed from the patient.

Figure 11:
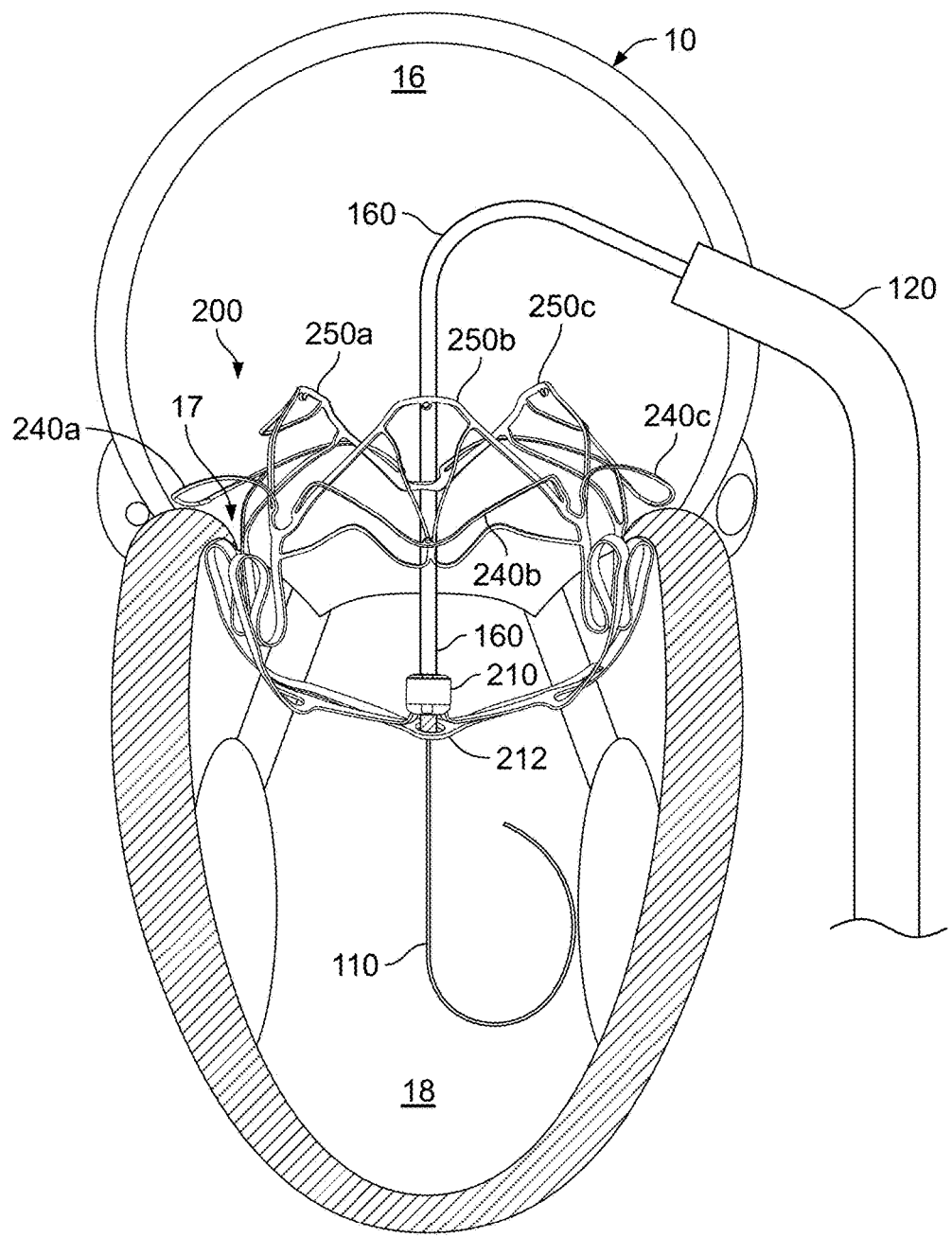
FIG. 11 shows a perspective view of the anchor assembly of FIG. 7 after the retraction of some of the catheters of the deployment system.

Referring also to FIG. 11, with the anchor assembly 200 deployed within the mitral valve 17 (as described above), the anchor delivery catheter 140 can be withdrawn, the secondary steerable catheter 150 can be withdrawn, and the anchor delivery sheath 130 can also be withdrawn. In fact, if so desired, the anchor delivery catheter 140, the secondary steerable catheter 150, and the anchor delivery sheath 130 can be completely withdrawn from the guide catheter 120. In contrast, in some implementations the inner catheter 160 is advantageously left attached to the hub 210 of the anchor assembly 200 (and left attached to the SAM containment member 212 in some implementations). As will be described further below, in some implementations the inner catheter 160 can be used as a "rail" on which a valve assembly is later deployed into the interior of the anchor assembly 200. However, in some implementations the anchor assembly 200 is completely detached from the delivery system 100, and the delivery system 100 is removed from the patient. After a period of minutes, hours, days, weeks, or months, subsequent to the deployment of the anchor assembly 200, a valve assembly can be installed into the anchor assembly 200 to complete the installation of the prosthetic mitral valve.

In some implementations, withdrawal of the anchor delivery catheter 140, the secondary steerable catheter 150, and the anchor delivery sheath 130 can be performed as follows. First, the anchor delivery catheter 140 can be withdrawn into the anchor delivery sheath 130. Then, the secondary steerable catheter 150 can be withdrawn into the anchor delivery sheath 130 while generally simultaneously undeflecting (relaxing) the bend(s) in the secondary steerable catheter 150. Thereafter, in some embodiments the anchor delivery catheter 140, the secondary steerable catheter 150, and the anchor delivery sheath 130 can be simultaneously withdrawn further, including up to completely from the guide catheter 120. As described further below, such individual and/or simultaneous movements of components of the delivery system 100 can be initiated and controlled using a deployment frame system (such as the example deployment frame system of FIG. 43 described below) in some implementations.

In the depicted implementation, the SAM containment member 212 is still restrained in its pre-deployed configuration. As described further below, in some embodiments the depicted embodiment of the SAM containment member 212 is deployed after the installation of a valve assembly into the anchor assembly 200. Alternatively, as described further below, in some embodiments of the SAM containment member 212, the SAM containment member 212 is deployed prior to the installation of a valve assembly into the anchor assembly 200.

Figure 12:
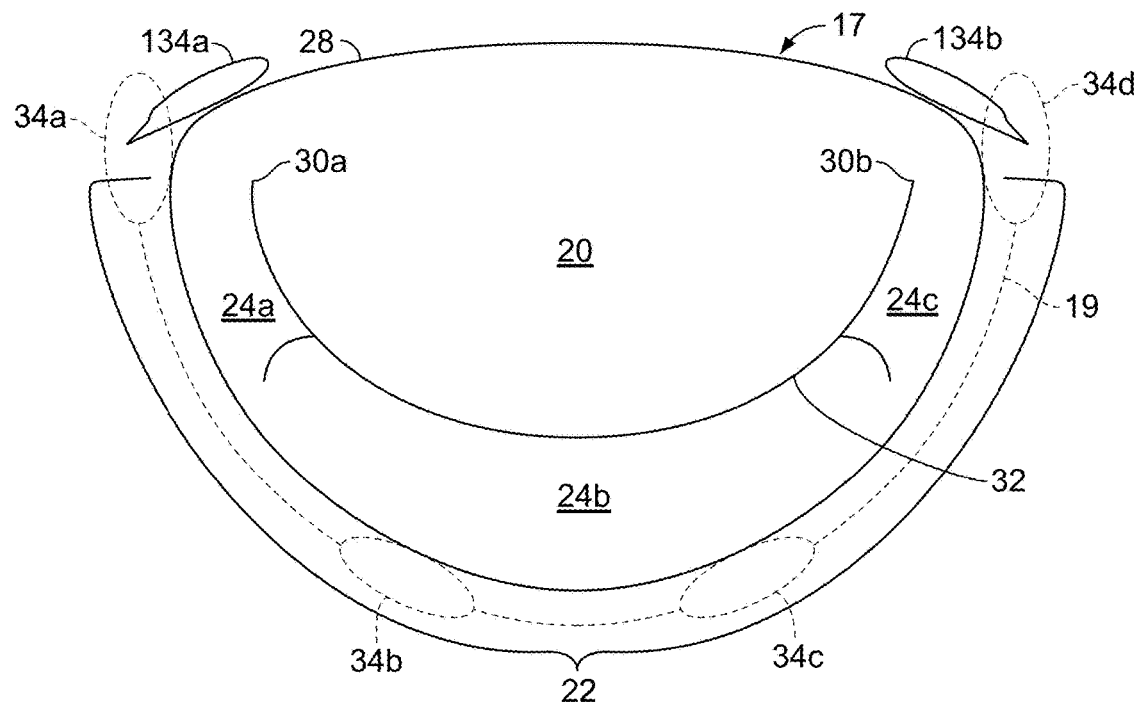
FIG. 12 is a top view of a native mitral valve and depicts a gutter perimeter of the sub-annular gutter of FIG. 7 (without the anchor assembly).

Referring to FIG. 12, the anatomy of the native mitral valve 17 includes some consistent and predictable structural features across patients that can be utilized for engaging the anchor assembly 200 therewith. For example, the native mitral valve 17 includes the aforementioned sub-annular gutter 19. In addition, the native mitral valve 17 includes a D-shaped annulus 28, an anterolateral commissure 30a, a posteromedial commissure 30b, a left fibrous trigone 134a, and a right fibrous trigone 134b. Further, the native mitral valve 17 includes an anterior leaflet 20 and a three-part posterior leaflet 22. The posterior leaflet 22 includes a lateral scallop 24a, a middle scallop 24b, and a medial scallop 24c. The free edges of the posterior leaflet 22 and the anterior leaflet 20 meet along a coaptation line 32.

The D-shaped annulus 28 defines the structure from which the anterior leaflet 20 and posterior leaflet 22 extend and articulate. The left and right fibrous trigones 134a and 134b are located near the left and right ends of the anterior leaflet 20 and generally adjacent the lateral and medial scallops 24a and 24c of the posterior leaflet 22. The sub-annular gutter 19 runs along the annulus 28 between the left and right fibrous trigones 134a and 134b along the posterior leaflet 22.

The regions at or near the high collagen annular trigones 134a and 134b can generally be relied upon to provide strong, stable anchoring locations. The muscle tissue in the regions at or near the trigones 134a and 134b also provides a good tissue ingrowth substrate for added stability and migration resistance of the anchor assembly 200. Therefore, the regions at or near the trigones 134a and 134b define a left anterior anchor zone 34a and a right anterior anchor zone 34d respectively. The left anterior anchor zone 34a and the right anterior anchor zone 34d provide advantageous target locations for placement of the lateral anterior foot 220a and the medial anterior foot 220d respectively.

Figure 13:
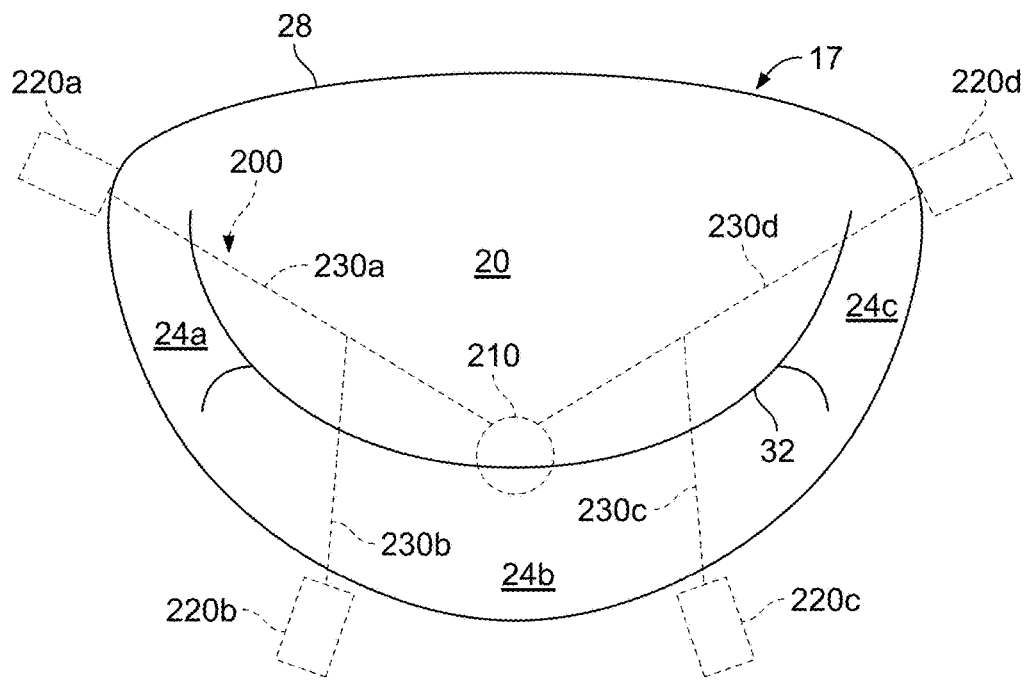
FIG. 13 shows the native mitral valve of FIG. 12 and a schematic representation of the sub-annular frame members of the anchor assembly of FIG. 7.

Referring also to FIG. 13, a schematic representation of the anchor assembly 200 is shown in combination with the native mitral valve 17 of FIG. 12. The depicted portions of the anchor assembly 200 include the hub 210, the lateral anterior anchor foot 220a, the lateral posterior anchor foot 220b, the medial posterior anchor foot 220c, the medial anterior anchor foot 220d, the lateral anterior sub-annular support arm 230a, the lateral posterior sub-annular support arm 230b, the medial posterior sub-annular support arm 230c, and the medial anterior sub-annular support arm 230d. Each of those portions of the anchor assembly 200 reside below the mitral valve 17 when deployed, hence those portions of the anchor assembly 200 are drawn with dashed lines.

In the depicted embodiment, the lateral anterior sub-annular support arm 230a extends from the hub 210. The lateral anterior anchor foot 220a is disposed on an outer end of the lateral anterior sub-annular support arm 230a. Similarly, the medial anterior sub-annular support arm 230d extends from the hub 210, and the medial anterior anchor foot 220d is disposed on an outer end of the medial anterior sub-annular support arm 230d. The lateral posterior sub-annular support arm 230b extends from a middle portion of the lateral anterior sub-annular support arm 230a. The lateral posterior anchor foot 220b is disposed on an outer end of the lateral posterior sub-annular support arm 230b. The medial posterior sub-annular support arm 230c extends from a middle portion of the medial anterior sub-annular support arm 230d. The medial posterior anchor foot 220c is disposed on an outer end of the medial posterior sub-annular support arm 230c.

The depicted arrangement of the sub-annular support arms 230a, 230b, 230c, and 230d is advantageous because the arrangement is designed to reduce or minimize the potential for interference (by the anchor assembly 200) with the natural functioning of the chordae tendineae of the mitral valve 17. For example, the lateral posterior sub-annular support arm 230b and the medial posterior sub-annular support arm 230c are aligned generally parallel with the chordae tendineae in the areas where the posterior sub-annular support arms 230b and 230c are disposed.

Moreover, other sub-annular portions of the anchor assembly are also positioned in advantageous locations for interfacing with the native mitral valve 17. For example, the hub 210 is advantageously positioned generally directly below the coaptation line 32. In addition, the lateral anterior anchor foot 220a can be positioned in the left anterior anchor zone 34a and the medial anterior anchor foot 220d can be positioned in the right anterior anchor zone 34d. Further, the lateral posterior anchor foot 220b and the medial posterior anchor foot 220c can be positioned in posterior areas of the sub-annular gutter 19, namely a lateral posterior anchor zone 34b and a medial posterior anchor zone 34c, respectively, in order to provide balanced and atraumatic coupling of the anchor assembly 200 to the native mitral valve 17. In some implementations, the locations of the lateral posterior anchor zone 34b and the medial posterior anchor zone 34c may vary from the depicted locations while still remaining within the sub-annular gutter 19. It should be understood that the depicted anchor assembly 200 is merely one non-limiting example of the anchor assemblies provided within the scope of this disclosure.

Figure 14:
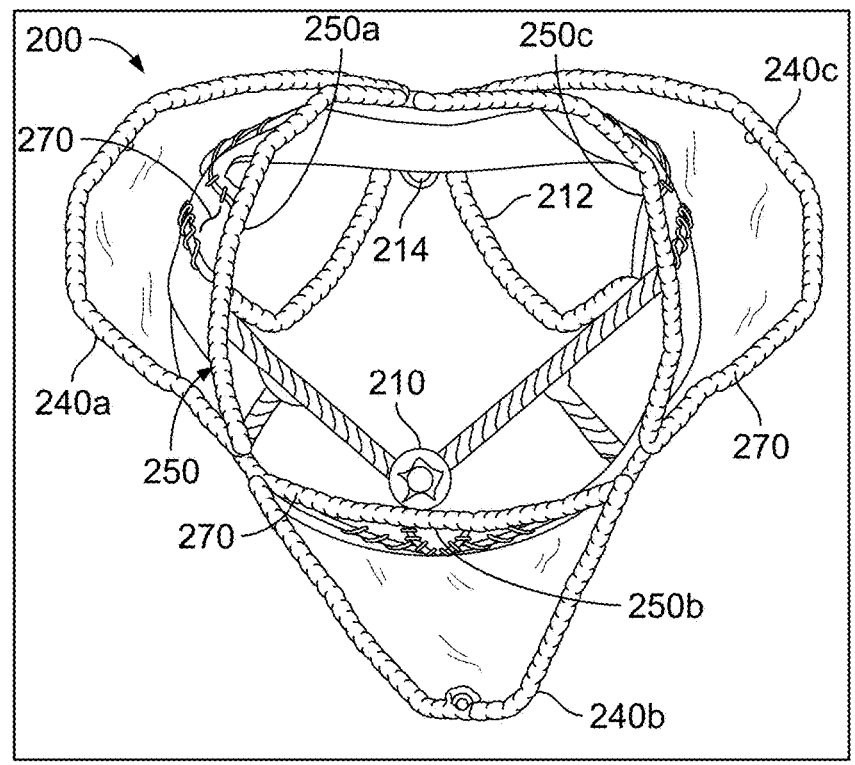
FIG. 14 shows a top view of the anchor assembly of FIG. 7 deployed in a sheet material that represents the annular plane of a mitral valve.
Figure 15:
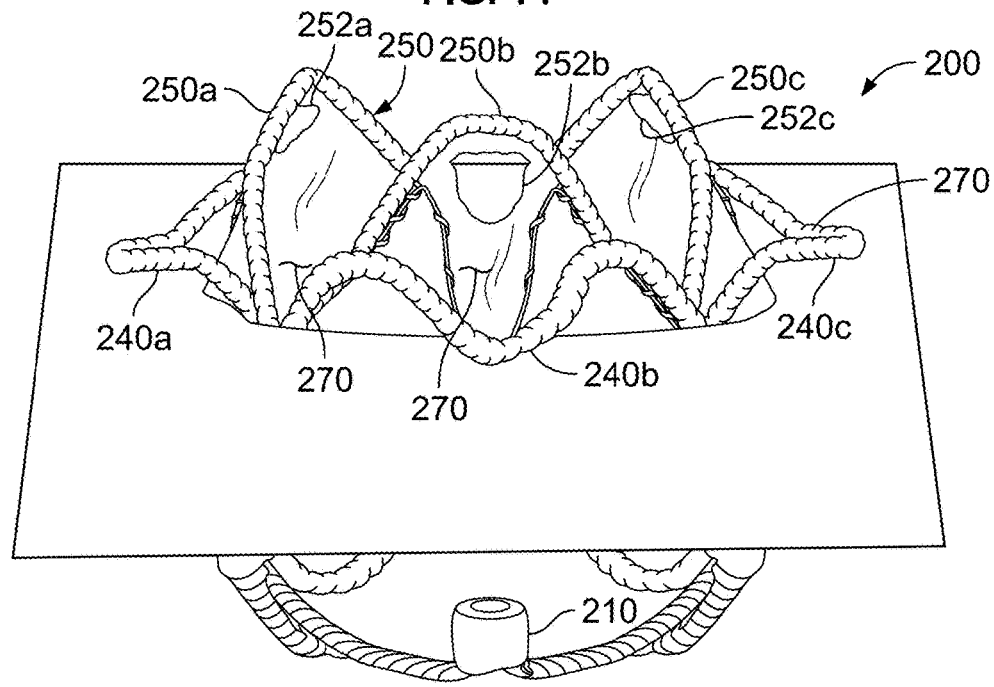
FIG. 15 shows a perspective view (slightly from the top) of the anchor assembly of FIG. 7 deployed in the material that represents the annular plane of a mitral valve (as in FIG. 14).

With reference to FIGS. 14 and 15, the example anchor assembly 200 is shown in a sheet material that represents the annular plane of a native mitral valve, to more clearly show which structures are supra-annular vs. sub-annular. A covering-material 270 is included on the framework of the anchor assembly 200. The supra-annular structures of the example anchor assembly 200 are shown.

In the depicted embodiment, the supra-annular structures of the anchor assembly 200 include: the lateral anterior atrial holding feature 240a, the posterior atrial holding feature 240b, and the medial anterior atrial holding feature 240c; the lateral anterior anchor arch 250a, the posterior anchor arch 250b, and the medial anterior anchor arch 250c. The lateral anterior anchor arch 250a, the posterior anchor arch 250b, and the medial anterior anchor arch 250c are joined with each other to form an undulating supra-annular ring 250 that acts as a supra-annular structural element for the anchor assembly 200. As will be described further below, the supra-annular ring 250 also defines an opening to a space within the interior of the anchor assembly 200 that is configured to receive and engage with a valve assembly. The atrial holding features 240a, 240b, and 240c are configured to contact the shelf-like supra-annular tissue surface above the mitral valve annulus, and to thereby stabilize the anchor assembly 200 in supra-annular areas and to provide migration resistance in the direction towards the left ventricle.

In some embodiments, the anchor assembly 200 includes a covering material 270 disposed on one or more portions of the anchor assembly 200. The covering material 270 can provide various benefits. For example, in some implementations the covering material 270 can facilitate tissue ingrowth and/or endothelialization, thereby enhancing the migration resistance of the anchor assembly 200 and preventing thrombus formation on blood contact elements. In another example, as described further below, the covering material 270 can be used to facilitate coupling between the anchor assembly 200 and a valve assembly that is received therein. The cover material 270 also prevents or minimizes abrasion and/or fretting between the anchor assembly 200 and valve assembly 300. The cover material 270 also prevents valve outer tissue abrasion related wear, and supports to the cuff material to enhance durability. The covering material 270 may also provide redundant sealing in addition to the cuff material of the valve assembly.

In the depicted embodiment, the covering material 270 is disposed essentially on the entire anchor assembly 200, including the SAM containment member 212 (except for the eyelet 214, although in some embodiments the eyelet 214 may be essentially covered by the covering material 270). In some embodiments, the covering material 270 is disposed on one or more portions of the anchor assembly 200, while one or more other portions of the anchor assembly 200 do not have the covering material 270 disposed thereon. While the depicted embodiment includes the covering material 270, the covering material 270 is not required in all embodiments. In some embodiments, two or more portions of covering material 270, which can be separated and/or distinct from each other, can be disposed on the anchor assembly 200. That is, in some embodiments a particular type of covering material 270 is disposed on some areas of the anchor assembly 200 and a different type of covering material 270 is disposed on other areas of the anchor assembly 200.

In some embodiments, the covering material 270, or portions thereof, comprises a fluoropolymer, such as an expanded polytetrafluoroethylene (ePTFE) polymer. In some embodiments, the covering material 270, or portions thereof, comprises a polyester, a silicone, a urethane, ELAST-EON™ (a silicone and urethane polymer), another biocompatible polymer, DACRON®, polyethylene terephthalate (PET), copolymers, or combinations and sub-combinations thereof. In some embodiments, the covering material 270 is manufactured using techniques such as, but not limited to, extrusion, expansion, heat-treating, sintering, knitting, braiding, weaving, chemically treating, and the like. In some embodiments, the covering material 270, or portions thereof, comprises a biological tissue. For example, in some embodiments the covering material 270 can include natural tissues such as, but not limited to, bovine, porcine, ovine, or equine pericardium. In some such embodiments, the tissues are chemically treated using glutaraldehyde, formaldehyde, or triglycidylamine (TGA) solutions, or other suitable tissue crosslinking agents.

In the depicted embodiment, the covering material 270 is disposed on the interior and the exterior of the anchor assembly 200. In some embodiments, the covering material 270 is disposed on the just the exterior of the anchor assembly 200. In some embodiments, the covering material 270 is disposed on the just the interior of the anchor assembly 200. In some embodiments, some portions of the anchor assembly 200 are covered by the covering material 270 in a different manner than other portions of the anchor assembly 200.

In some embodiments, the covering material 270 is attached to at least some portions of the anchor assembly 200 using an adhesive. In some embodiments, epoxy is used as an adhesive to attach the covering material 270 to the anchor assembly 200, or portions thereof. In some embodiments, wrapping, stitching, lashing, banding, and/or clips, and the like can be used to attach the covering material 270 to the anchor assembly 200. In some embodiments, a combination of techniques are used to attach the covering material 270 to the anchor assembly 200.

In some embodiments, the covering material 270, or portions thereof, has a microporous structure that provides a tissue ingrowth scaffold for durable sealing and/or supplemental anchoring strength of the anchor assembly 200. In some embodiments, the covering material 270 is made of a membranous material that inhibits or reduces the passage of blood through the covering material 270. In some embodiments, the covering material 270, or portions thereof, has a material composition and/or configuration that inhibits or prevents tissue ingrowth and/or endothelialization to the covering material 270.

In some embodiments, the covering material 270 can be modified by one or more chemical or physical processes that enhance certain physical properties of the covering material 270. For example, a hydrophilic coating may be applied to the covering material 270 to improve the wettability and echo translucency of the covering material 270. In some embodiments, the covering material 270 may be modified with chemical moieties that promote or inhibit one or more of endothelial cell attachment, endothelial cell migration, endothelial cell proliferation, and resistance to thrombosis. In some embodiments, the covering material 270 may be modified with covalently attached heparin or impregnated with one or more drug substances that are released in situ.

In some embodiments, covering material 270 is pre-perforated to modulate fluid flow through the covering material 270 and/or to affect the propensity for tissue ingrowth to the covering material 270. In some embodiments, the covering material 270 is treated to make the covering material 270 stiffer or to add surface texture. In some embodiments, selected portions of the covering material 270 are so treated, while other portions of the covering material 270 are not so treated. Other covering material 270 material treatment techniques can also be employed to provide beneficial mechanical properties and tissue response interactions. In some embodiments, portions of the covering material 270 have one or more radiopaque markers attached thereto to enhance in vivo radiographic visualization.

In some embodiments, the anchor assembly 200 can include features that are designed for coupling with a valve assembly that is received by the anchor assembly 200. For example, the lateral anterior anchor arch 250*a*, the posterior anchor arch 250*b*, and the medial anterior anchor arch 250*c* can be shaped and arranged for coupling with a valve assembly (as described further below). In addition, in some embodiments the anchor arches 250*a*, 250*b*, and 250*c* can include one or more covering-material cut-outs 252*a*, 252*b*, and 252*c* respectively. In some embodiments, the valve assembly (as described further below in reference to FIG. 38) can include features that become physically disposed within the covering-material cut-outs 252*a*, 252*b*, and 252*c* when the valve assembly is coupled with the anchor assembly 200. Such an arrangement can serve to provide a robust coupling arrangement between the valve assembly and the anchor assembly 200.

Figure 16:
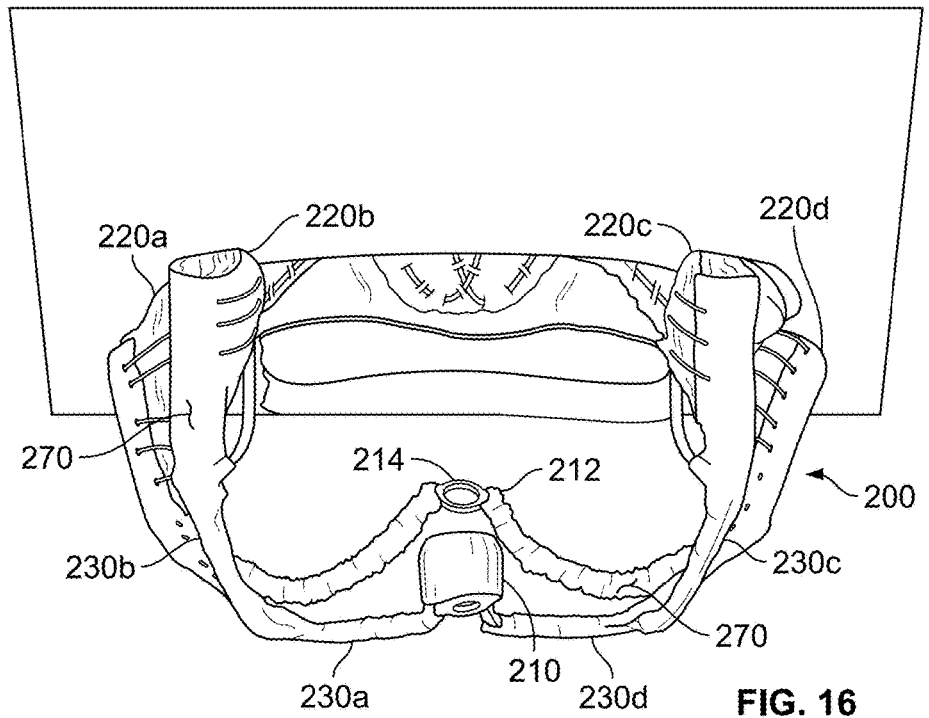
FIG. 16 shows a perspective view (slightly from the bottom) of the anchor assembly of FIG. 7 deployed in the material that represents the annular plane of a mitral valve (as in FIG. 14).
Figure 17:
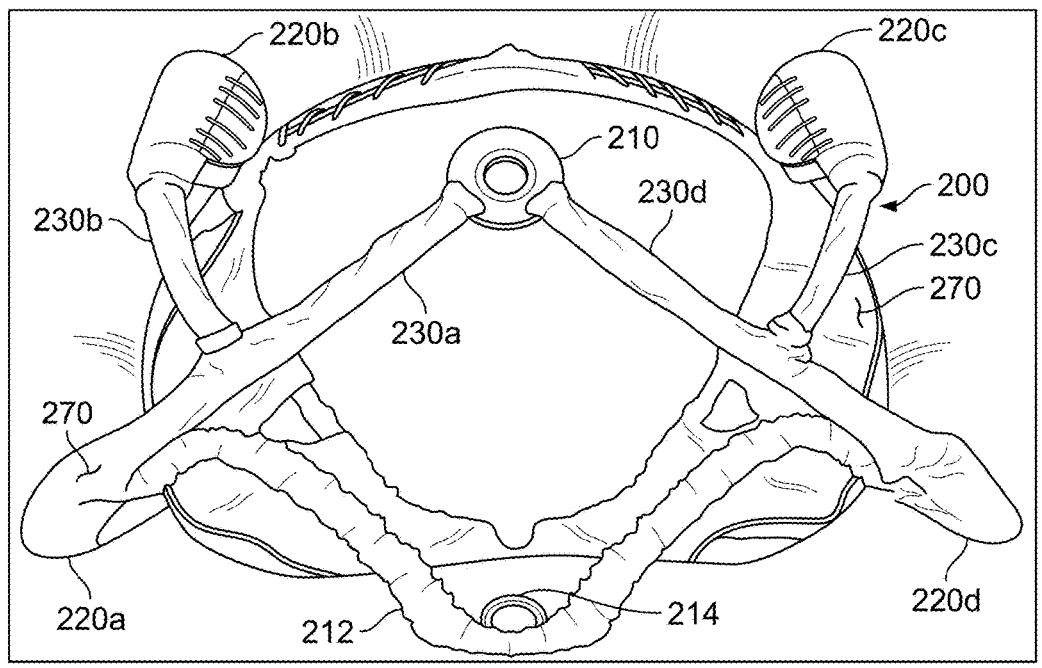
FIG. 17 shows a bottom view of the anchor assembly of FIG. 7 deployed in the material that represents the annular plane of a mitral valve (as in FIG. 14).

With reference to FIGS. 16 and 17, the example anchor assembly 200 is shown in a sheet material that represents the annular plane of a native mitral valve. The sub-annular portions of the example anchor assembly 200 are shown.

In the depicted embodiment, the sub-annular portions of the anchor assembly 200 include the hub 210, the SAM containment member 212, the lateral anterior anchor foot 220*a*, the lateral posterior anchor foot 220*b*, the medial posterior anchor foot 220*c*, the medial anterior anchor foot 220*d*, the lateral anterior sub-annular support arm 230*a*, the lateral posterior sub-annular support arm 230*b*, the medial posterior sub-annular support arm 230*c*, and the medial anterior sub-annular support arm 230*d*. Each of those portions of the anchor assembly 200 reside below the native mitral valve annulus when deployed the anchor assembly 200 is deployed in a native mitral valve.

In the depicted embodiment, the lateral anterior sub-annular support arm 230*a* extends from the hub 210. The lateral anterior anchor foot 220*a* is disposed on an outer end of the lateral anterior sub-annular support arm 230*a*. Similarly, the medial anterior sub-annular support arm 230*d* extends from the hub 210, and the medial anterior anchor foot 220*d* is disposed on an outer end of the medial anterior sub-annular support arm 230*d*. The lateral posterior sub-annular support arm 230*b* extends from a middle portion of the lateral anterior sub-annular support arm 230*a*. The lateral posterior anchor foot 220*b* is disposed on an outer end of the lateral posterior sub-annular support arm 230*b*. The medial posterior sub-annular support arm 230*c* extends from a middle portion of the medial anterior sub-annular support arm 230*d*. The medial posterior anchor foot 220*c* is disposed on an outer end of the medial posterior sub-annular support arm 230*c*. A first end of the SAM containment member 212 extends from the lateral anterior sub-annular support arm 230*a*, and a second end of the SAM containment member 212 extends from the medial anterior sub-annular support arm 230*d*.

Referring to FIGS. 18-21, the frame of an example anchor assembly 200 is shown in its fully expanded configuration. The anchor assembly 200 is shown without a covering-material so that the elongate member framework of the example anchor assembly 200 is clearly visible in FIGS. 18-20, and with covering-material in FIG. 21.

In some embodiments, the elongate members of the anchor assembly 200 are formed from a single piece of precursor material (e.g., sheet or tube) that is cut, expanded, and connected to the hub 210. For example, some embodiments are fabricated from a tube that is laser-cut (or machined, chemically etched, water-jet cut, etc.) and then expanded and shape-set into its final expanded size and shape. In some embodiments, the anchor assembly 200 is created compositely from multiple elongate members (e.g., wires or cut members) that are joined together with the hub 210 and each other to form the anchor assembly 200.

Figure 18:
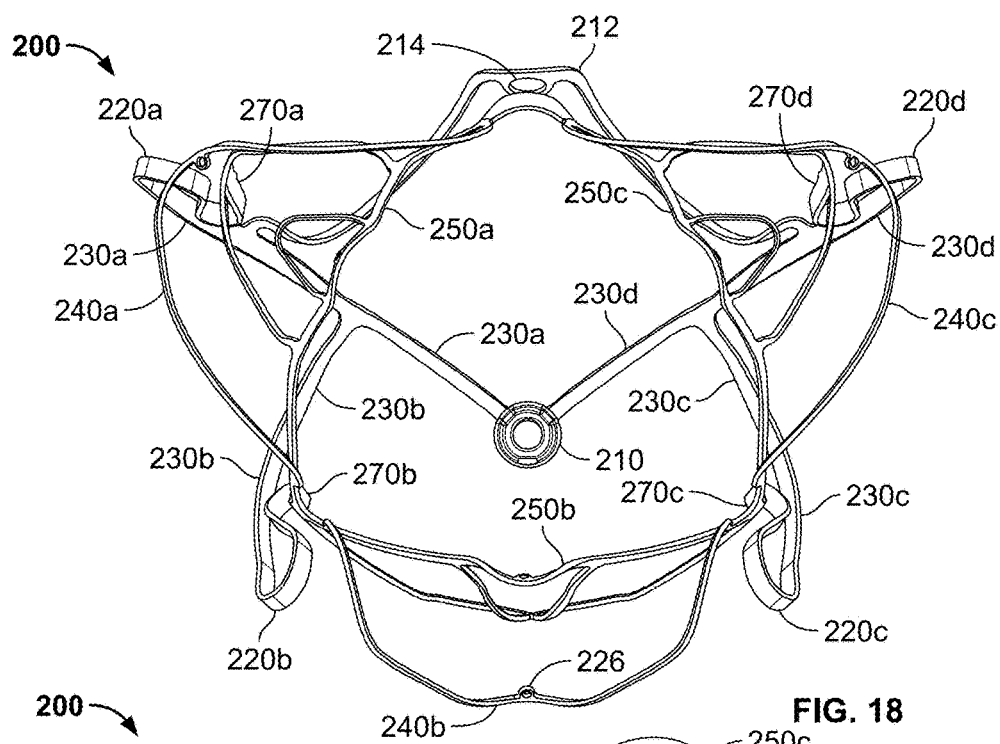
FIG. 18 shows a perspective top view of an example frame of the anchor assembly of FIG. 7, in accordance with some embodiments.
Figure 19:
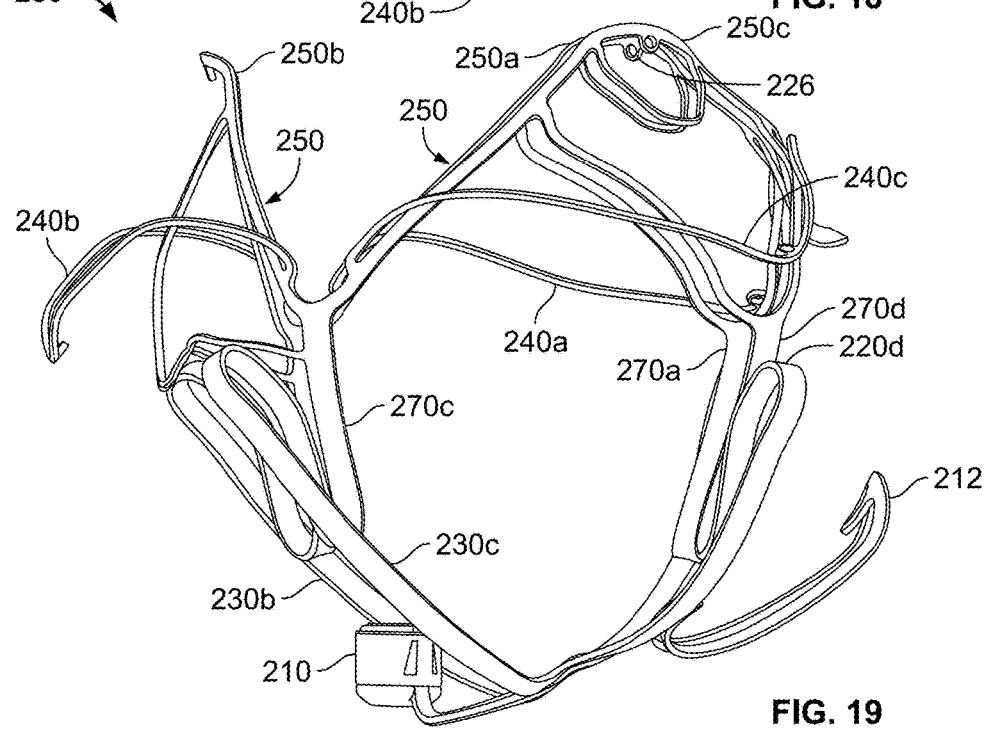
FIG. 19 shows a perspective side view of the example frame of the anchor assembly of FIG. 7, in accordance with some embodiments.
Figure 20:
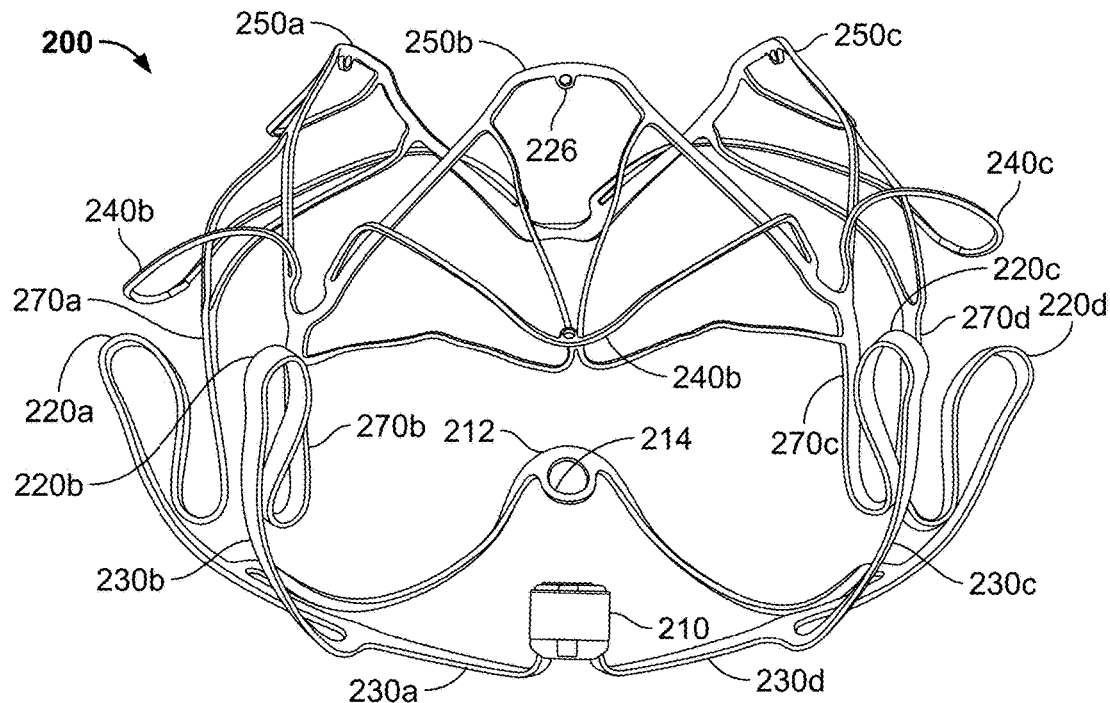
FIG. 20 shows a posterior side view of the example frame of the anchor assembly of FIG. 7, in accordance with some embodiments.
Figure 21:
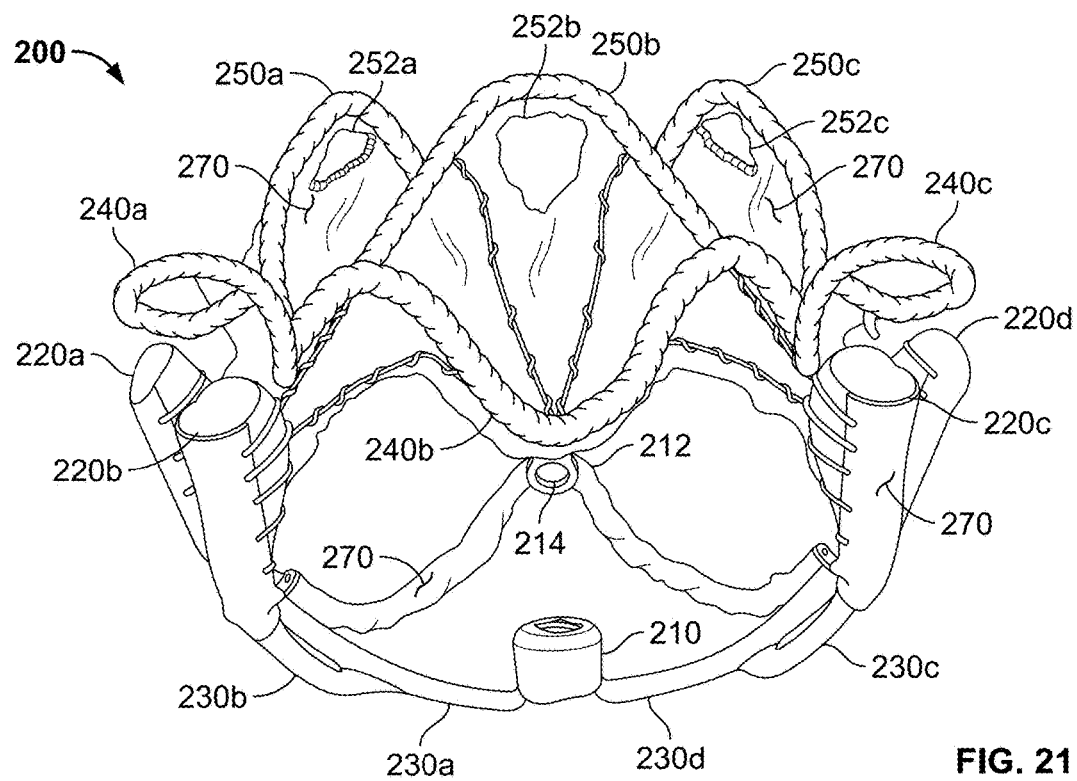
FIG. 21 shows a posterior side view (slightly from the top) of the anchor assembly of FIG. 7 including a covering material disposed on portions of the anchor frame.

The elongate members of the anchor assembly 200 can be comprised of various materials and combinations of materials. In some embodiments, nitinol (NiTi) is used as the material of the elongate members of the anchor assembly 200, but other materials such as stainless steel, L605 steel, polymers, MP35N steel, stainless steels, titanium, cobalt/chromium alloy, polymeric materials, Pyhnox, Elgiloy, or any other appropriate biocompatible material, and combinations thereof can be used. The super-elastic properties of NiTi make it a particularly good candidate material for the elongate members of the anchor assembly 200 because, for example, NiTi can be heat-set into a desired shape. That is, NiTi can be heat-set so that the anchor assembly 200 tends to self-expand into a desired shape when the anchor assembly 200 is unconstrained, such as when the anchor assembly 200 is deployed out from the anchor delivery sheath 130. A anchor assembly 200 made of NiTi, for example, may have a spring nature that allows the anchor assembly 200 to be elastically collapsed or "crushed" to a low-profile delivery configuration and then to reconfigure to the expanded configuration as shown in FIGS. 18-20. The anchor assembly 200 may be generally conformable, fatigue resistant, and elastic such that the anchor assembly 200 can conform to the topography of the surrounding tissue when the anchor assembly 200 is deployed in a native mitral valve of a patient.

In some embodiments, the diameter or width/thickness of one or more of the elongate members forming the anchor assembly 200 may be within a range of about 0.008" to about 0.015" (about 0.20 mm to about 0.40 mm), or about 0.009" to about 0.030" (about 0.23 mm to about 0.76 mm), or about 0.01" to about 0.06" (about 0.25 mm to about 1.52 mm), or about 0.02" to about 0.10" (about 0.51 mm to about 2.54 mm), or about 0.06" to about 0.20" (about 1.52 mm to about 5.08 mm). In some embodiments, the elongate members forming the anchor assembly 200 may have smaller or larger diameters or widths/thicknesses. In some embodiments, each of the elongate members forming the anchor assembly 200 has essentially the same diameter or width/thickness. In some embodiments, one or more of the elongate members forming the anchor assembly 200 has a different diameter or width/thickness than one or more of the other elongate members of the anchor assembly 200. In some embodiments, one or more portions of one or more of the elongate members forming the anchor assembly 200 may be tapered, widened, narrowed, curved, radiused, wavy, spiraled, angled, and/or otherwise non-linear and/or not consistent along the entire length of the elongate members of the anchor assembly 200. Such features and techniques can also be incorporated with the valve assemblies of the prosthetic mitral valves provided herein.

In some embodiments, the elongate members forming the anchor assembly 200 may vary in diameter, thickness and/or width so as to facilitate variations in the forces that are exerted by the anchor assembly 200 in specific regions thereof, to increase or decrease the flexibility of the anchor assembly 200 in certain regions, to enhance migration resistance, and/or to control the process of compression (crushability) in preparation for deployment and the process of expansion during deployment of the anchor assembly 200.

In some embodiments, one or more of the elongate members of the elongate members forming the anchor assembly 200 may have a circular cross-section. In some embodiments, one or more of the elongate members forming the anchor assembly 200 may have a rectangular cross-sectional shape, or another cross-sectional shape that is not rectangular. Examples of cross-sectional shapes that the elongate members forming the anchor assembly 200 may have include circular, C-shaped, square, ovular, rectangular, elliptical, triangular, D-shaped, trapezoidal, including irregular cross-sectional shapes formed by a braided or stranded construct, and the like. In some embodiments, one or more of the elongate members forming the anchor assembly 200 may be essentially flat (i.e., such that the width to thickness ratio is about 2:1, about 3:1, about 4:1, about 5:1, or greater than about 5:1). In some examples, one or more of the elongate members forming the anchor assembly 200 may be formed using a center-less grind technique, such that the diameter of the elongate members varies along the length of the elongate members.

The anchor assembly 200 may include features that are directed to enhancing one or more desirable functional performance characteristics of the prosthetic mitral valve devices. For example, some features of the anchor assembly 200 may be directed to enhancing the conformability of the prosthetic mitral valve devices. Such features may facilitate improved performance of the prosthetic mitral valve devices by allowing the devices to conform to irregular tissue topographies and/or dynamically variable tissue topographies, for example. Such conformability characteristics can be advantageous for providing effective and durable performance of the prosthetic mitral valve devices. In some embodiments of the anchor assembly 200, some portions of the anchor assembly 200 are designed to be more conformable than other portions of the same anchor assembly 200.

That is, the conformability of a single anchor assembly 200 can be designed to be different at various areas of the anchor assembly 200.

In some embodiments, the anchor assembly 200 includes features for enhanced in vivo radiographic visibility. In some embodiments, portions of the anchor assembly 200, such as one or more of the anchor feet 220a, 220b, 220c, and 220d, and/or SAM containment member 212, may have one or more radiopaque markers attached thereto. In some embodiments, some or all portions of the anchor assembly 200 are coated (e.g., sputter coated) with a radiopaque coating.

The anchor assembly 200 can also include one or more eyelets 226 in frame portions adjacent the arches. The eyelets 226 can be used for various purposes such as, but not limited to, holding radiopaque marker material, attachment points for suture loops or other elements which are additional control points for delivery and retrieval of the assembly, locations to secure a positional delivery frame, and the like.

In some embodiments, such as the depicted embodiment, the supra-annular structures and sub-annular structures of the anchor assembly 200 are interconnected by a lateral anterior inter-annular connection 270a, a lateral posterior inter-annular connection 270b, a medial posterior inter-annular connection 270c, and a medial anterior inter-annular connection 270d. For example, the lateral anterior inter-annular connection 270a connects the lateral anterior anchor foot 220a with the lateral anterior anchor arch 250a. Similarly, the medial anterior inter-annular connection 270d connects the medial anterior anchor foot 220d with the medial anterior anchor arch 250c. In addition, the lateral posterior inter-annular connection 270b connects the lateral posterior anchor foot 220b with the lateral anterior anchor arch 250a and the posterior anchor arch 250b, and the medial posterior inter-annular connection 270c connects the medial posterior anchor foot 220c with the posterior anchor arch 250b and the medial anterior anchor arch 250c.

In the depicted embodiment, the SAM containment member 212 extends anteriorly from the sub-annular support arms of the anchor assembly 200. For example, the SAM containment member 212, as depicted, comprises an elongate member with a first end that extends from the lateral anterior sub-annular support arm 230a and a second end that extends from the medial anterior sub-annular support arm 230d. In some embodiments, portions of the SAM containment member 212 may extend from other areas on the anchor assembly 200. While one particular embodiment of the SAM containment member 212 is depicted, it should be understood that multiple SAM containment member embodiments are envisioned and within the scope of this disclosure.

In the depicted embodiment, the SAM containment member 212 is integrally formed as part of the anchor assembly 200. In specific embodiments, the SAM containment member 212, or portions thereof, may be formed separately from the anchor assembly 200 and thereafter attached to the anchor assembly 200.

The SAM containment member 212, as shown, is in a deployed configuration. In some embodiments, the SAM containment member 212 is biased to self-reconfigure to the deployed configuration when the SAM containment member 212 is unconstrained. When the anchor assembly 200 is implanted in a native mitral valve and the SAM containment member 212 is in the deployed configuration, the SAM containment member 212 is disposed behind the anterior leaflet of a native mitral valve to physically block the anterior leaflet from obstructing the LVOT. As used herein, "behind" an anterior leaflet refers to the aortic side of the native mitral valve leaflet when the leaflet is open. In some implementations, while the SAM containment member 212 is deployed, the elongate members of the SAM containment member 212 may engage with the anterior leaflet and/or chordae to reduce the likelihood of SAM. The engagement can be anywhere along the lengths of the elongate members of the SAM containment member 212. For example, in some implementations portions of the elongate members of the SAM containment member 212 can actually engage the lateral edge of the anterior leaflet and/or chordae to spread or widen the anterior leaflet at the lateral edges thereby restricting its movement and also reducing likelihood of SAM.

In some embodiments, a shape-setting process is used to instill a bias so that the SAM containment member 212 tends seek its deployed configuration. Alternatively or additionally, as described further below, in some embodiments the SAM containment member 212 may be deflected into the deployed configuration by the application of one or more forces during the deployment of the SAM containment member 212.

In some embodiments, the SAM containment member 212 includes an attachment element 214 (a threaded eyelet 214 in this embodiment). The eyelet 214 provides an attachment feature that can be used to control the configuration and deployment of the SAM containment member 212. In some embodiments, other types of attachment elements 214 (as alternatives to the eyelet 214) can be included on the SAM containment member 212. For example, in some embodiments one or more protrusions, ball ends, recesses, clips, breakable elements, deflectable elements, bends, and the like, and combinations thereof, can be included on the SAM containment member 212 as an attachment element 214.

Still referring to FIGS. 18-21, as described above the anchor feet 220a, 220b, 220c, and 220d are sized and shaped to engage the sub-annular gutter 19 of the mitral valve 17 (FIG. 12). In some embodiments, the anterior feet 220a and 220d are spaced apart from each other by a distance in a range of about 30 mm to about 45 mm, or about 20 mm to about 35 mm, or about 40 mm to about 55 mm. In some embodiments, the posterior feet 220b and 220c are spaced apart from each other by a distance in a range of about 20 mm to about 30 mm, or about 10 mm to about 25 mm, or about 25 mm to about 40 mm.

In some embodiments, the anchor feet 220a, 220b, 220c, and 220d have a height ranging from about 8 mm to about 12 mm, or more than about 12 mm. In some embodiments, the anchor feet 220a, 220b, 220c, and 220d have a gutter engaging surface area (when fabric covered) ranging from about 6 mm$^2$ to about 24 mm$^2$. In some embodiments, the anchor feet 220a, 220b, 220c, and 220d each have essentially the same gutter engaging surface area. In particular embodiments, one or more of the anchor feet 220a, 220b, 220c, and 220d has a different gutter engaging surface area than one or more of the other anchor feet 220a, 220b, 220c, and 220d. The anchor feet 220a, 220b, 220c, and 220d can have widths ranging within about 1.5 mm to about 4.0 mm or more, and lengths ranging within about 3 mm to about 6 mm or more. The anchor feet 220a, 220b, 220c, and 220d are sized and shaped so that the anchor assembly 200 does not significantly impair the natural function of mitral valve chordae tendineae, the native mitral valve leaflets, and papillary muscles even after the anchor assembly is anchored at the mitral valve site.

As described previously, the anchor assembly 200 is designed to avoid interference with the functioning of the native mitral valve 17 (FIG. 12). Therefore, the anchor assembly 200 can be implanted within the native mitral valve 17 some time prior to the deployment therein of a replacement valve assembly, without degradation of valve 17 function during the period of time between the anchor implantation and the valve implantation (whether that time is on the order of minutes, or even several days or months). To avoid such interference between the anchor assembly 200 and the native mitral valve 17, the inter-annular connections 270a, 270b, 270c, and 270d pass through the coaptation line 32 approximately. More particularly, the lateral anterior inter-annular connection 270a passes through the coaptation line 32 adjacent to the anterolateral commissure 30a. In like manner, the medial anterior inter-annular connection 270d passes through the coaptation line 32 adjacent to the posteromedial commissure 30b. In some implementations, the lateral posterior inter-annular connection 270b and medial posterior inter-annular connection 270c pass through the native mitral valve 17 in locations that are posteriorly biased from the natural coaptation line 32. In such a case, the posterior leaflet 22 will tend to compliantly wrap around the lateral posterior inter-annular connection 270b and medial posterior inter-annular connection 270c to facilitate sealing of the mitral valve 17 with the anchor assembly 200 coupled thereto.

Figure 22:
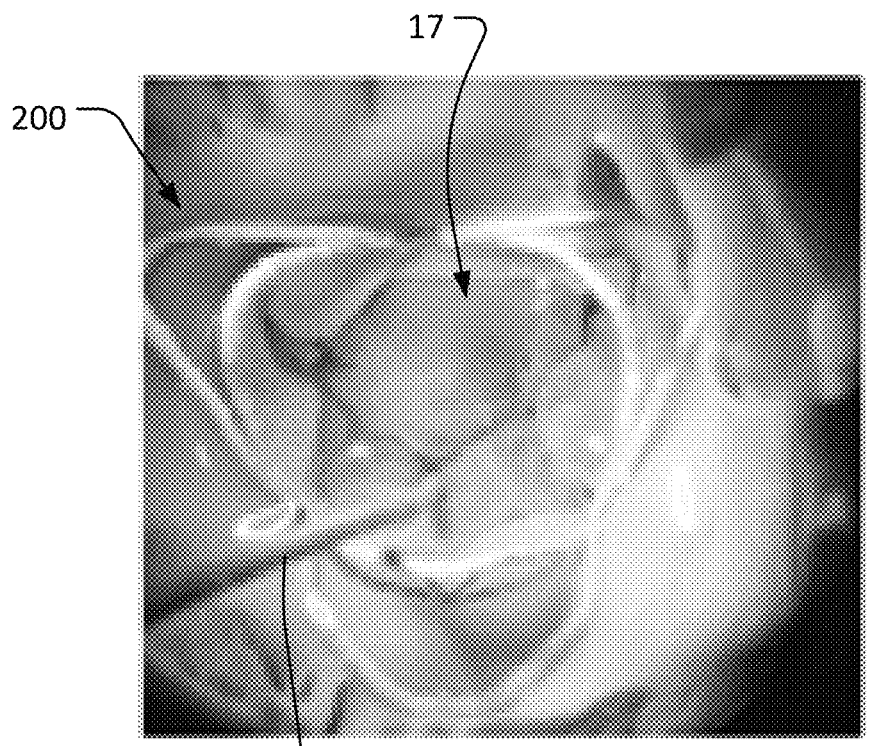
FIG. 22 is a photographic image showing a perspective top view of the anchor assembly of FIG. 7 implanted within a native mitral valve (with the native mitral valve leaflets in a closed state)
Figure 23:
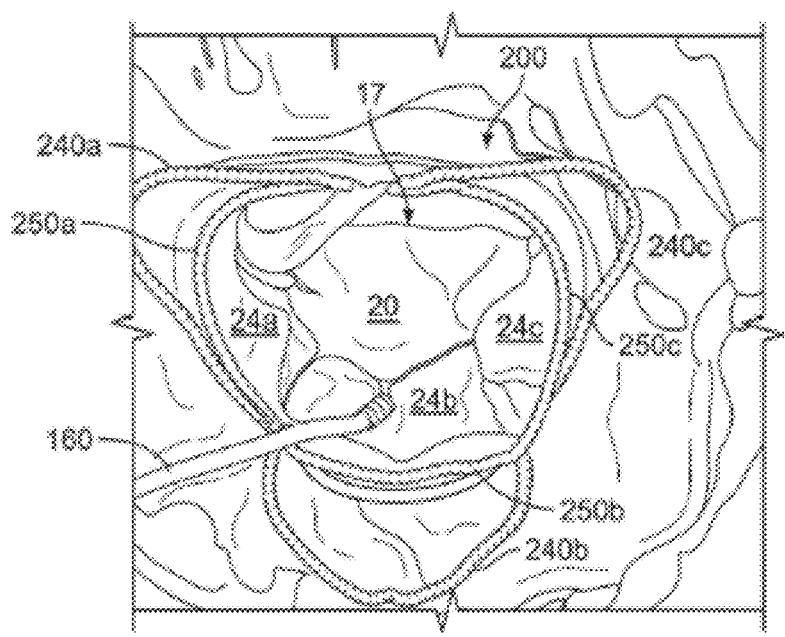
FIG. 23 shows a corresponding anatomical top view of the anchor assembly of FIG. 22.
Figure 24:
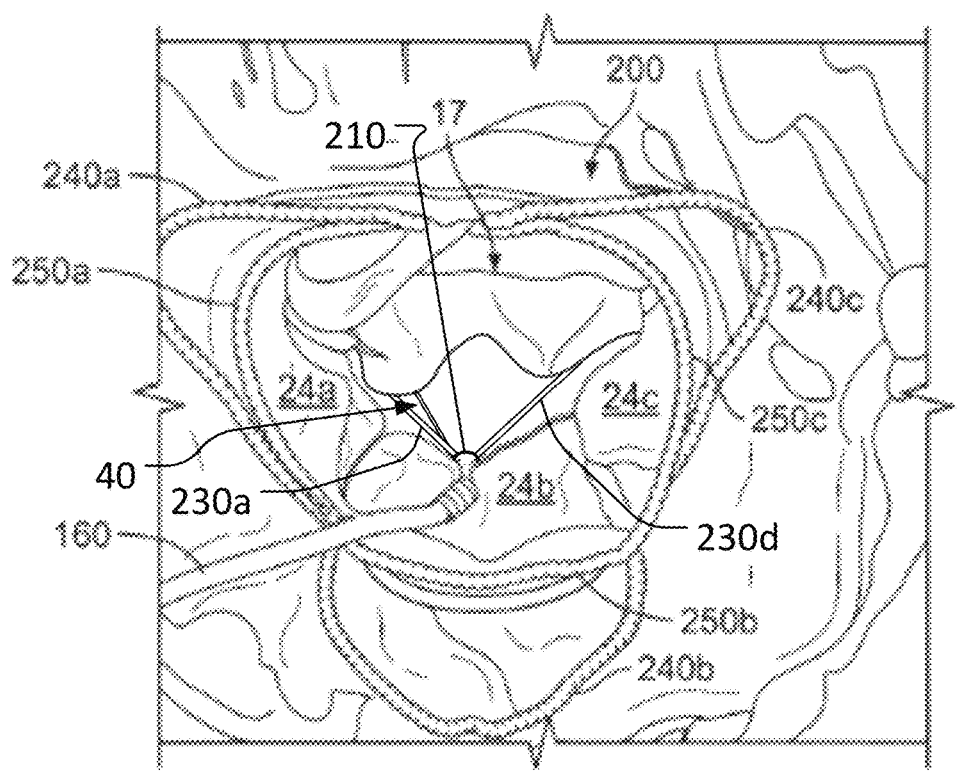
FIG. 24 is a photographic image showing a perspective top view of the anchor assembly of FIG. 7 implanted within a native mitral valve (with the native mitral valve leaflets in an open state).

Referring to FIGS. 22-24, the anchor assembly 200 is shown implanted within a native mitral valve 17. The inner catheter 160 is still coupled to the anchor assembly 200 in these figures. FIG. 22 is a photographic image that corresponds to FIG. 23 which shows the mitral valve 17 in a closed state. FIG. 24 is a photographic image showing the anchor assembly 200 coupled with the native mitral valve 17 while the mitral valve 17 is in an open state. These illustrations are from the perspective of the left atrium looking inferior (downwardly) towards the mitral valve 17. For instance, in FIG. 24 some chordae tendineae 40 are visible through the open leaflets of the mitral valve 17.

These figures illustrate the supra-annular structures and sub-annular structures of the anchor assembly 200 in their relationships with the native mitral valve 17. For example, the closed state of the native mitral valve 17 in FIGS. 22 and 23 allows visibility of the supra-annular structures such as the lateral anterior atrial holding feature 240a, the posterior atrial holding feature 240b, and the medial anterior atrial holding feature 240c. In addition, the lateral anterior anchor arch 250a, the posterior anchor arch 250b, and the medial anterior anchor arch 250c are visible. However, the sub-annular structures are not visible in FIG. 13A because such structures are obstructed from view by the anterior leaflet 20 and the three-part posterior leaflet 24a, 24b, and 24c.

In contrast, in FIG. 24 certain sub-annular structures of the anchor assembly 200 are visible because the native mitral valve 17 is open. For example, the medial anterior sub-annular support arm 230d and hub 210 are in view through the open mitral valve 17. Other sub-annular portions of the anchor assembly 200, such as the anchor feet 220a, 220b, 220c, and 220d, remain out of view because of visual obstructions of the native mitral valve 17. In addition, no SAM containment member (which is a sub-annular structure) is visible in this view as it is in its pre-deployed configuration.

Figure 25:
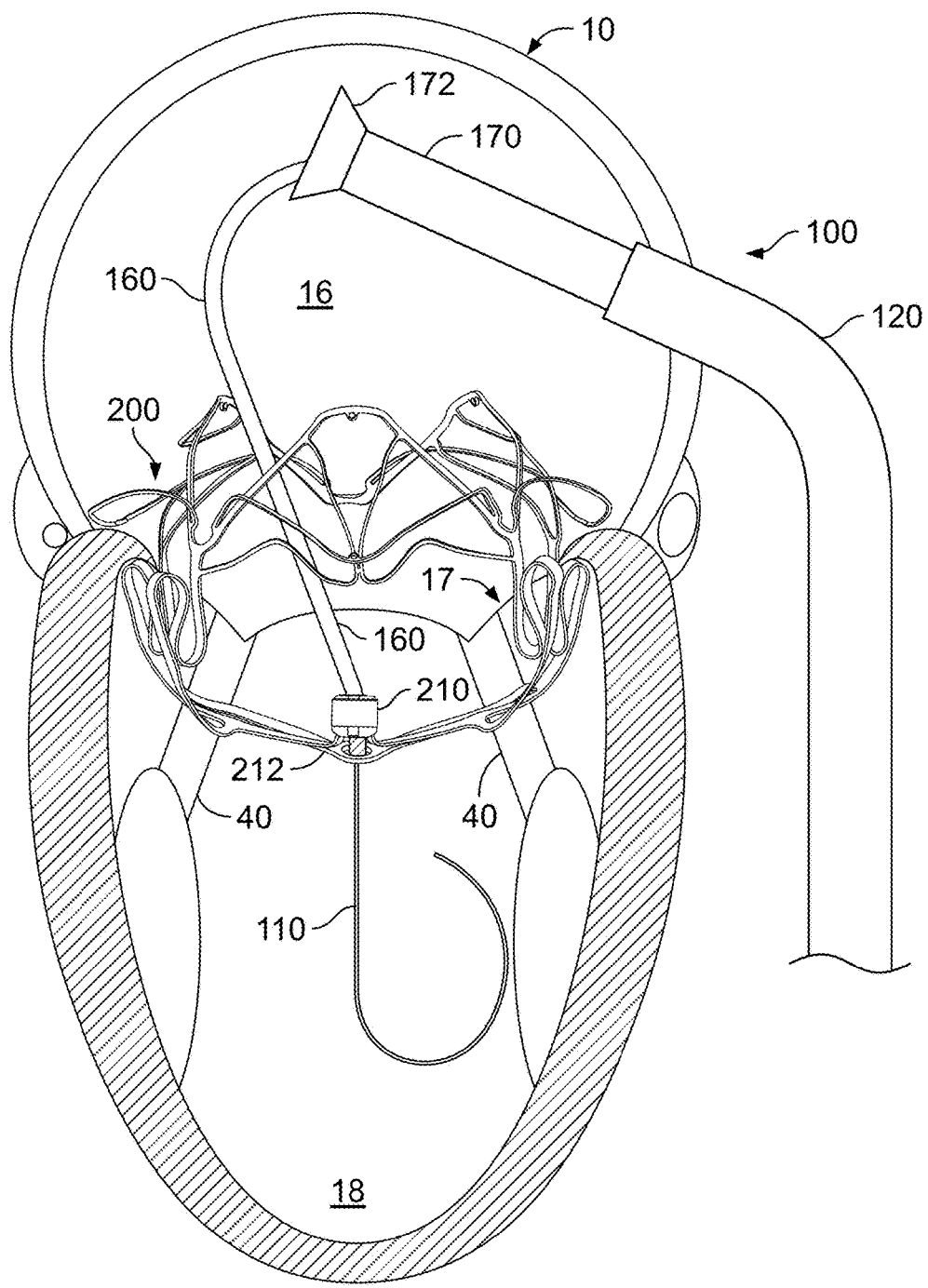
FIG. 25 shows a perspective view of the anchor assembly of FIG. 7 implanted within the native mitral valve and a valve assembly delivery sheath extending into the left atrium (in a commissural cross-sectional view of the heart).

Referring to FIG. 25, after implantation of the anchor assembly 200 within the native mitral valve 17 (as performed, for example, in accordance with FIGS. 1-5 and 7-11 described above), a valve delivery sheath 170 of the delivery system 100 can be used to deploy a valve assembly within the anchor assembly 200. As described above in reference to FIG. 11, with the inner catheter 160 coupled with the hub 210 of the anchor assembly 200, the inner catheter 160 can be used to guide the valve assembly into the interior of the anchor assembly 200.

In the depicted embodiment, the SAM containment member 212 is constrained in its pre-deployed configuration. However, in some other SAM containment member embodiments, the SAM containment member may be deployed prior to installation of a valve assembly within the anchor assembly 200. Generally speaking, depending on the SAM containment member embodiment's design, if the SAM containment member may potentially interfere with the function of the anterior leaflet, it may be preferable to wait until the valve is implanted to deploy the SAM containment member. But, if the SAM containment member does not or is unlikely to interfere with the leaflet function, the SAM containment member may be deployed prior to valve implant (which may be beneficial for situations where the anchor is implanted in a separate procedure from the valve implantation).

In some implementations, with the guide catheter 120 positioned with its distal end in the left atrium 16, the valve delivery sheath 170 is installed into a lumen of the guide catheter 120 (over the inner catheter 160) and advanced through the guide catheter 120. As described further below, in some embodiments the valve delivery sheath 170 is loaded at that time with a prosthetic valve assembly and other components of the delivery system 100. The guide catheter 120 may be the same catheter that was used to deliver the anchor assembly 200, or it may be a different catheter (but still referred to here as the guide catheter 120 for simplicity sake). Depending on the time interval between implantation of the anchor assembly 200 and the valve assembly 300, it may also be desirable to leave the same guide catheter 120 in situ during the time between the deliveries of each assembly.

In some embodiments, the valve delivery sheath 170 can be made from the materials described above in reference to the guide catheter 120. In some embodiments, the valve delivery sheath 170 has an outer diameter in the range of about 20 Fr to about 28 Fr (about 6.7 mm to about 9.3 mm). In some embodiments, the valve delivery sheath 170 has an outer diameter in the range of about 14 Fr to about 24 Fr (about 4.7 mm to about 8.0 mm).

In the depicted embodiment, the valve delivery sheath 170 includes a flared distal end portion 172. In some embodiments, no such flared distal end portion 172 is included. The flared distal end portion 172 can collapse to a lower profile when constrained within the guide catheter 120. When the flared distal end portion 172 is expressed from the guide catheter 120, the flared distal end portion 172 can self-expand to the flared shape. In some embodiments, the material of the flared distal end portion 172 includes pleats or folds, may be a continuous flared end or may be separated into sections such as flower pedals, and may include one or more resilient elements that bias the flared distal end portion 172 to assume the flared configuration in the absence of restraining forces (such as from containment within the guide catheter 120). The flared distal end portion 172 can be advantageous, for example, for recapturing the valve assembly (if desired) within the lumen of the valve delivery sheath 170 after the valve assembly has been expressed from the flared distal end portion 172.

In some embodiments, the maximum outer diameter of the flared distal end portion 172 is in a range of about 30 Fr to about 34 Fr (about 10.0 mm to about 11.3 mm). In some embodiments, the maximum outer diameter of the flared distal end portion 172 is in a range of about 32 Fr to about 44 Fr (about 10.7 mm to about 14.7 mm). In some embodiments, the maximum outer diameter of the flared distal end portion 172 is in a range of about 24 Fr to about 30 Fr (about 8.0 mm to about 10.0 mm). In some embodiments, the maximum outer diameter of the flared distal end portion 172 is less than about 24 Fr (about 8.0 mm) or greater than about 44 Fr (about 14.7 mm).

Figure 26:
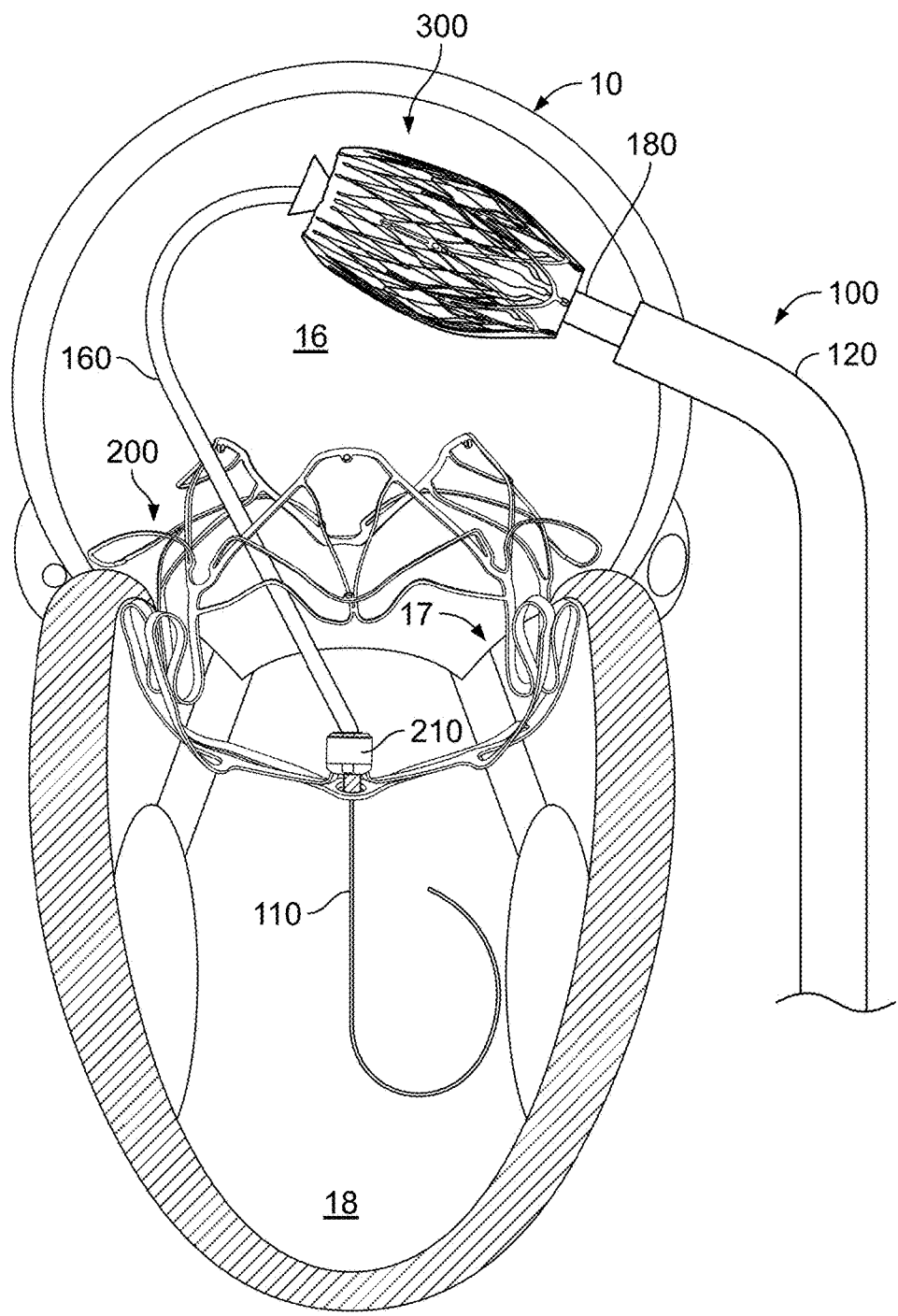
FIG. 26 shows a perspective view of a valve assembly in the left atrium after partial emergence from the valve assembly delivery sheath of FIG. 25. The valve assembly is configured in a first (partially expanded) arrangement.

Referring also to FIG. 26, in some implementations the valve delivery sheath 170 can be withdrawn into the guide catheter 120 while a valve delivery catheter 180 is held substantially stationary to thereby express a valve assembly 300 from a lumen of the valve delivery sheath 170. The valve delivery sheath 170 and the valve delivery catheter 180 are additional components in some embodiments of the example delivery system 100. It should be understood that movements of the components (e.g., the valve delivery sheath 170 and the valve delivery catheter 180) of the delivery system 100, whether the movements be those of individual components or two or more components in combination with each other, can in some embodiments be initiated and controlled using a deployment frame system (such as the example deployment frame system of FIG. 43 described below).

Figure 6:
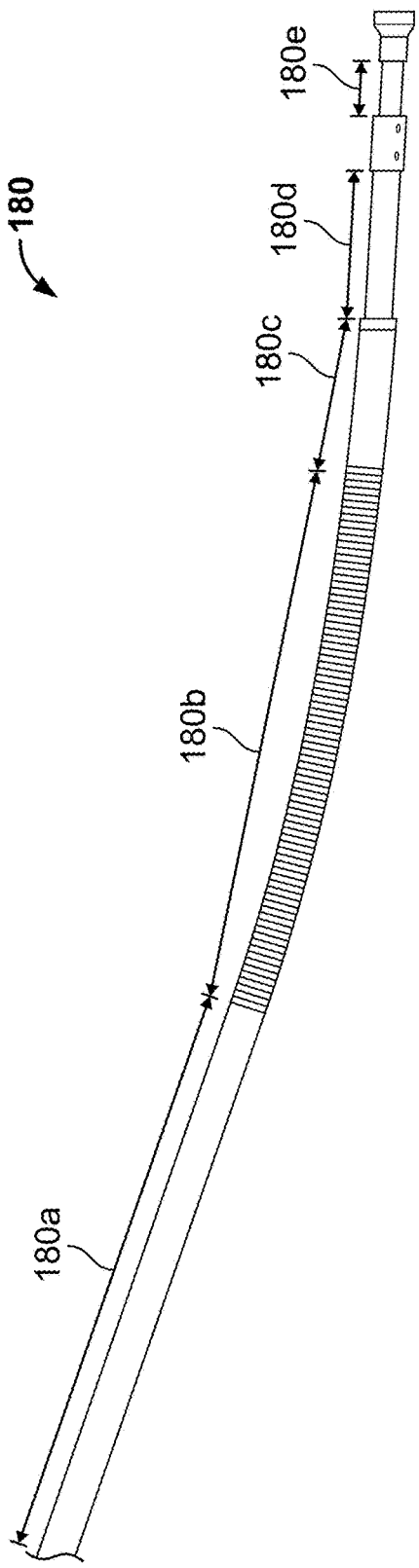
FIG. 6 shows a side view of a delivery catheter of prosthetic mitral valve deployment system.

Referring also to FIG. 6, in some embodiments the valve delivery catheter 180 can be advantageously configured with multiple zones that have differing mechanical properties such as flexibility, durometer, column strength, crush strength, elasticity, torqueability, trackability, and the like. For example, in the depicted embodiment the valve delivery catheter 180 includes a first zone 180a, a second zone 180b, a third zone 180c, a fourth zone 180d, and a fifth zone 180e. In one example, the first zone 180a has a durometer of about 72 D, the second zone 180b has a durometer of about 35 D, the third zone 180c has a durometer of about 25 D, the fourth zone 180d has a durometer of about 55 D, and the fifth zone 180e has a durometer of about 35 D. The different zones may be constructed differently in relation to each other (e.g., using different polymers, coatings, coil reinforcements, braided reinforcements, hypotubes, etc.). Such variations in the mechanical properties (e.g., flexibility, etc.) of the valve delivery catheter 180 can be advantageous for the navigation of the valve delivery catheter 180 through the curvatures of a patient's vasculature. For example, in the depicted embodiment, the first zone 180a being 72 D (for example) provides column strength for the section of the valve delivery catheter 180 that is expected to be in the inferior vena cava and/or right atrium. The zones 180b, 180c, 180d and 180e having example durometers of 35 D, 25 D, 55 D and 35 D respectively provide the flexibility for the valve delivery catheter 180 to navigate the curvature from right atrium to mitral annulus plane through fossa ovalis and left atrium. The zone 180d of 55 D (for example) also provides the stiffness profile to align the axis of the valve delivery catheter 180 along the normal to the native mitral annulus plane. It should be understood that this is merely one example and other arrangements are also envisioned within the scope of this disclosure. Moreover, one or more other catheter devices of delivery system 100 can be configured with such multiple zones that have differing mechanical properties (as exemplified here in regard to valve delivery catheter 180).

Still referring to FIG. 26, the valve assembly 300 can be releasably coupled to the valve delivery catheter 180 and retained in a low-profile configuration. In some embodiments, both the distal and proximal ends of the valve assembly 300 are releasably coupled to the valve delivery catheter 180. In some embodiments, just one of the distal end or the proximal end of the valve assembly 300 is releasably coupled to the valve delivery catheter 180. In particular embodiments, one or more control wires may be included to releasably couple one or more portions of the valve assembly 300 to the valve delivery catheter 180. In some such embodiments, the one or more control wires may act as lassos to radially constrain the bias of the valve assembly 300 from radially self-expanding. Hence, a release of tension on the one or more control wires may allow at least a portion of the valve assembly 300 to radially self-expand.

Figure 27:
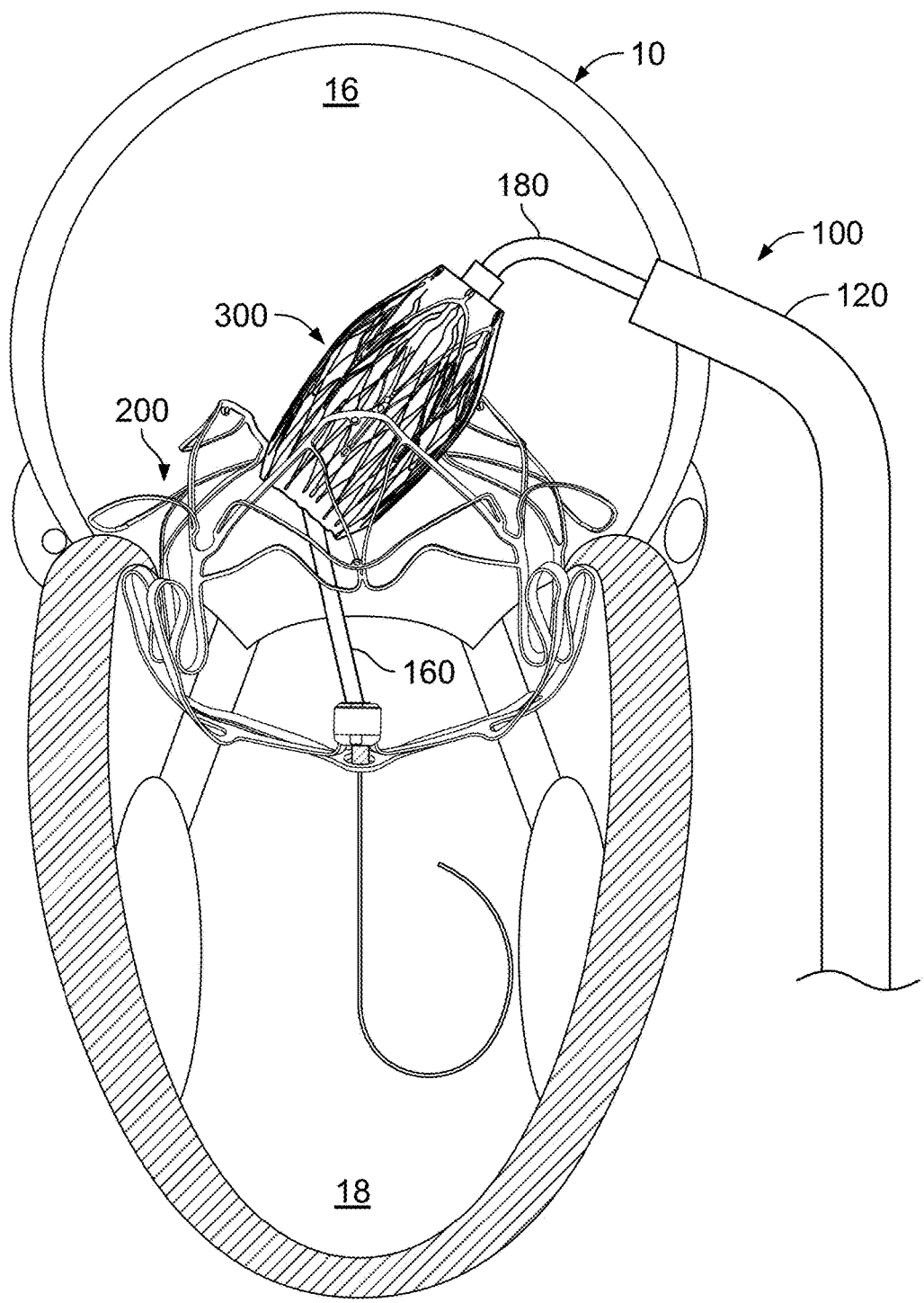
FIG. 27 shows a perspective view of the valve assembly of FIG. 26 with the valve deployment system being manipulated in preparation for the installation of the valve assembly into the anchor assembly.
Figure 28:
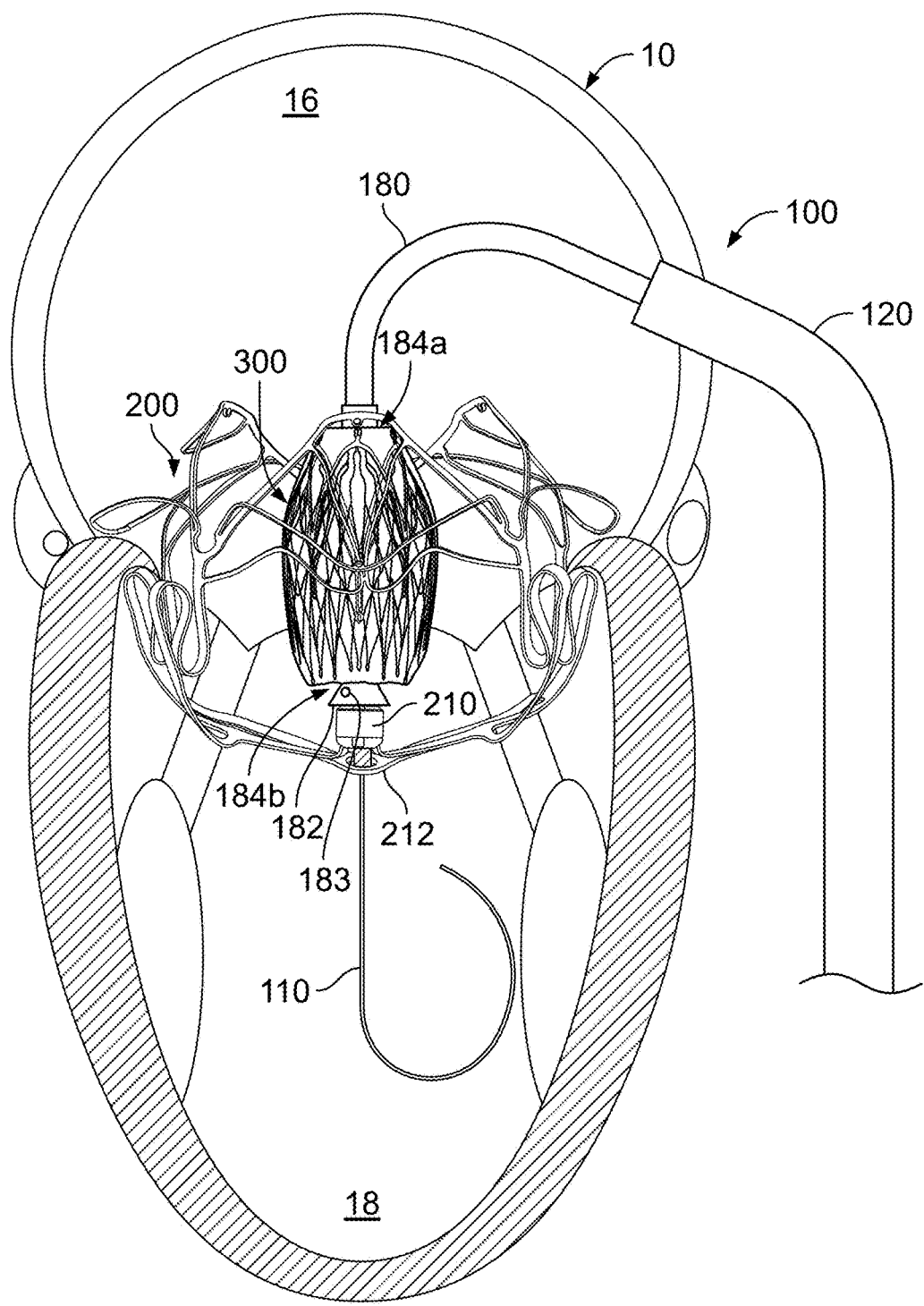
FIG. 28 shows a perspective view of the valve assembly of FIG. 26 (while still in the first, partially expanded arrangement) being positioned within the anchor assembly.

Referring to FIGS. 27 and 28, the delivery system 100 can be manipulated by a clinician operator to perform a lateral pivot (panning, rotation, etc.) of the valve assembly 300 within the left atrium 16. The rotation of the valve assembly 300 changes the alignment of the valve assembly 300 from being generally axial with the distal end portion of the guide catheter 120 to being generally axial with the anchor assembly 200 (in preparation for installation of the valve assembly 300 into the interior of the anchor assembly 200).

In some implementations, the aforementioned rotation of the valve assembly 300 can be performed as follows. As shown in FIG. 26, because of the influence from the guide catheter 120 on the valve delivery catheter 180, the axis of the valve assembly 300 is initially in general alignment with the axis of the distal end portion of the guide catheter 120. From this arrangement, a generally simultaneous counter-movement of/between the inner catheter 160 and the valve delivery catheter 180 can be performed by the clinician to rotate the valve assembly 300. That is, as the inner catheter 160 is pulled proximally, the valve delivery catheter 180 is pushed distally. As a result of that counter movement, the valve assembly 300 rotates/pans in a relatively tight radius within the left atrium 16, as required by the confines of the left atrium 16. Thereafter, the valve delivery catheter 180 can be advanced further so that the valve assembly 300 is coaxially positioned within the interior of the anchor assembly 200 as shown in FIG. 28. As with other movements of the components of the delivery system 100 described herein (and other movements of the components of the delivery system 100 that are like those described herein), the generally simultaneous counter-movements of/between the inner catheter 160 and the valve delivery catheter 180 can be initiated and controlled using a deployment frame system (such as the example deployment frame system of FIG. 43 described below) in some implementations.

Figure 29:
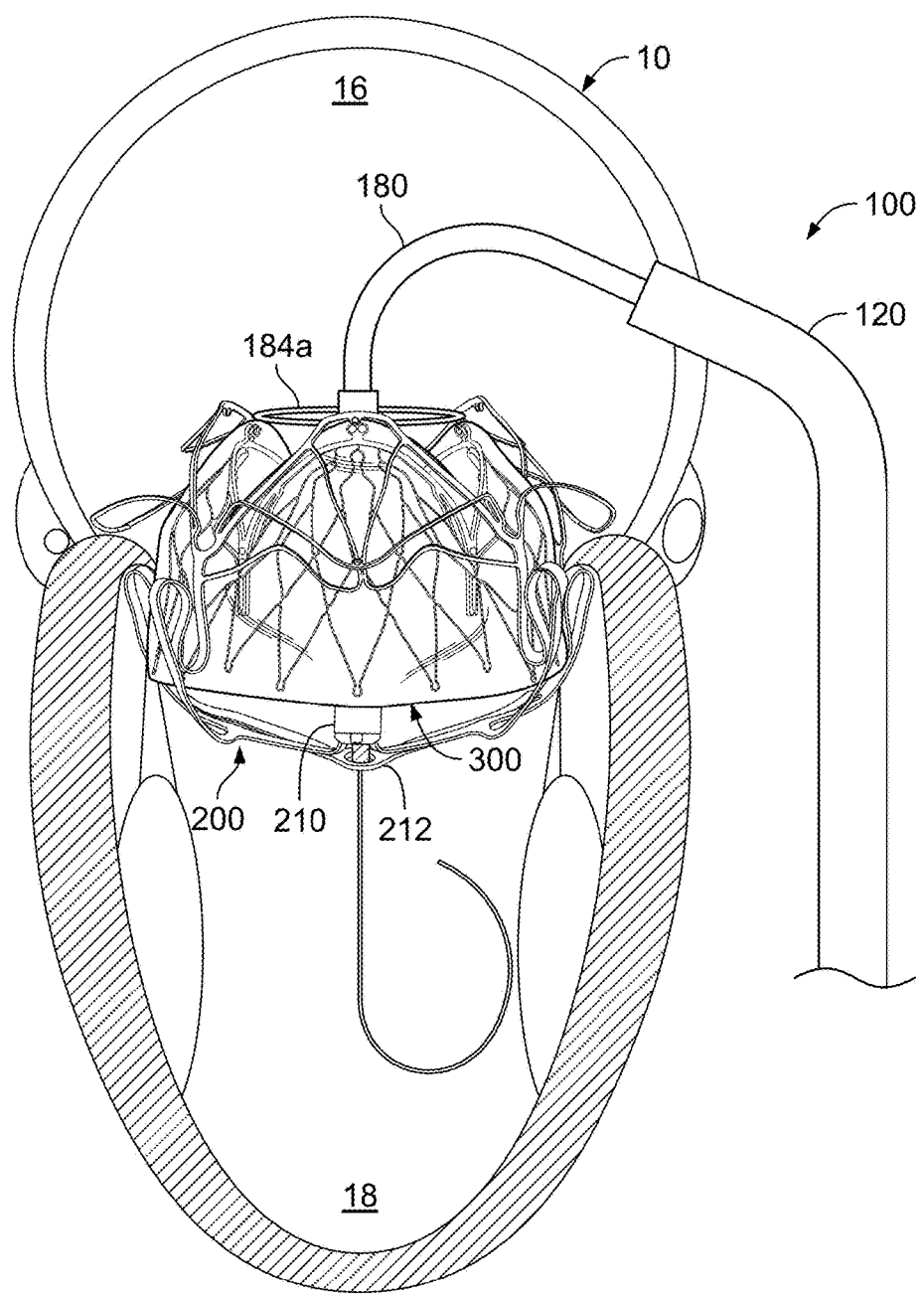
FIG. 29 shows a perspective view of the valve assembly of FIG. 26, with the valve assembly expanded within the anchor assembly, prior to deployment of the SAM containment member.
Figure 30:
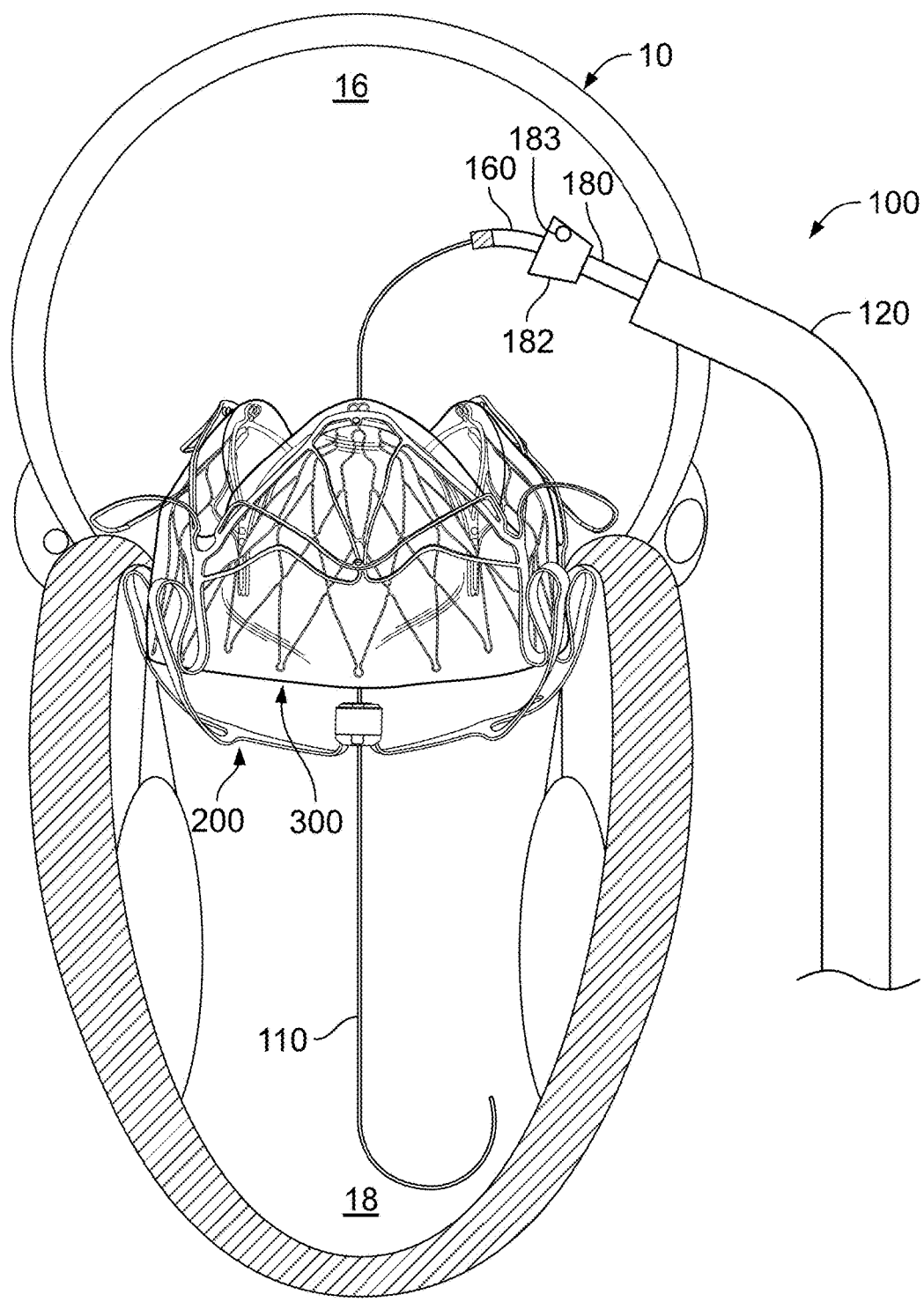
FIG. 30 shows a perspective view of the valve assembly of FIG. 26, with the valve assembly expanded within the anchor assembly after the release and retraction of the control wires of the deployment system, after deployment of the SAM containment member, and after the retraction of some of the catheters of the deployment system.

Referring now also to FIGS. 29 and 30, in some embodiments the valve assembly 300 and the anchor assembly 200 become aligned with each other coaxially, linearly (along their axes), and rotationally prior to or during the expansion of the valve assembly 300, resulting in engagement between the valve assembly 300 and the anchor assembly 200.

Coaxial alignment between the valve assembly 300 and the anchor assembly 200, as described above, is achieved by virtue of the valve delivery catheter 180 being slidably disposed over the inner catheter 160. Linear alignment between the valve assembly 300 and the anchor assembly 200 can be achieved by the interaction of a distal end feature 182 (FIG. 28) of the valve delivery catheter 180 and the hub 210 of the anchor assembly 200. For example, in some embodiments an abutting of the distal end feature 182 and the hub 210 can result in proper linear alignment between the valve assembly 300 and the anchor assembly 200. Such abutting of the distal end feature 182 and the hub 210 can be attained by translating the valve delivery catheter 180 distally until the distal end feature 182 abuts the hub 210.

Relative rotational alignment between the valve assembly 300 and the anchor assembly 200 (about their longitudinal axes) can be achieved in various manners. For example, in some embodiments the valve delivery catheter 180 is mechanically keyed to the inner catheter 160 to slidably fix a desired rotational alignment between the valve assembly 300 and the anchor assembly 200. In some embodiments, other types of mechanical features (e.g., pins/holes, protrusions/receptacles, etc.) can be included to facilitate a desired rotational/spin alignment between the valve assembly 300 and the anchor assembly 200. Alternatively, or additionally, one or more radiopaque markers can be included on the valve assembly 300 and/or on the anchor assembly 200 in locations and/or patterns that are indicative of the relative rotational orientation (about their axes) of the valve assembly 300 and the anchor assembly 200. Accordingly, fluoroscopy can be used to attain a desired relative orientation of the radiopaque markers and, consequently, of the valve assembly 300 and the anchor assembly 200. For example, in some embodiments one or more radiopaque markers 183 are disposed on the distal end feature 182. The one or more radiopaque markers 183 can be in locations and/or arranged in patterns to indicate the rotational orientation of the distal end feature 182 and, in turn, the rotational orientation of the valve assembly 300 that is releasably coupled in relation to the distal end feature 182. In some embodiments, the one or more radiopaque markers 183 can be arranged as one or more beads, one or more half-rings, and the like, and combinations thereof. One or more radiopaque markers can be included on the SAM containment member 212 in some embodiments.

In some embodiments (e.g., when the valve delivery catheter 180 is configured to be "torqueable"), the valve delivery catheter 180 can be rotated about its longitudinal axis until the radiopaque markers are in proper position relative to the anchor assembly 200, prior to final expansion of valve assembly 300. Such rotation of the valve delivery catheter 180 can, in some implementations, be initiated and controlled using a deployment frame. Fluoroscopy can be used to attain a desired relative orientation of the radiopaque markers, and of the valve assembly 300 and the anchor assembly 200 (including on the SAM containment member) correspondingly.

In the depicted implementation, the SAM containment member 212 is still in its pre-deployed configuration. Therefore, the depicted embodiment of the SAM containment member 212 is deployed after the valve assembly 300 is engaged within the anchor assembly 200. However, for some alternative embodiments of the SAM containment member (as described further below) the SAM containment member is deployed prior to the engagement of the valve assembly 300 within the anchor assembly 200.

After proper alignment between the valve assembly 300 and the anchor assembly 200 is achieved, the valve assembly 300 can be expanded within the interior of the anchor assembly 200 such that the valve assembly 300 and anchor assembly 200 become releasably coupled to each other. In some embodiments, force(s) are applied to the valve assembly 300 to cause it to expand. In some embodiments, the valve assembly 300 is biased to self-expand.

The expansion of a self-expanding valve assembly 300 can be initiated by releasing tension on the one or more control wires of the valve delivery catheter 180. For example, in some embodiments the valve delivery catheter 180 includes a proximal control wire 184a that restrains the proximal end portion of the valve assembly 300, and a distal control wire 184b that restrains the distal end portion of the valve assembly 300. As tension on the proximal control wire 184a is released, the proximal end portion of the valve assembly 300 is allowed to radially expand. Similarly, as tension on the distal control wire 184b is released, the distal end portion of the valve assembly 300 is allowed to radially expand. The expansions of the portions of the valve assembly 300 may be allowed to take place sequentially, concurrently, or partially concurrently. As described further below, such individual and/or simultaneous movements of components of the delivery system 100 (such as the one or more control wires of the valve delivery catheter 180) can be initiated and controlled using a deployment frame system in some implementations.

After the valve assembly 300 has been expanded into a coupled relationship with the anchor assembly 200, the clinician can verify that the anchor assembly 200 and the valve assembly 300 are in the desired positions. Additionally, the clinician may verify other aspects such as, but not limited to, the hemodynamic performance and sealing of the anchor assembly 200 and the valve assembly 300.

In some embodiments, the SAM containment member 212 is deployed after the valve assembly 300 has been expanded into a coupled relationship with the anchor assembly 200. To deploy the SAM containment member 212, in some embodiments the inner catheter 160 is rotated about its longitudinal axis so that the distal end of the inner catheter 160 is uncoupled from the hub 210 of the anchor assembly 200. For example, in some embodiments the distal end of the inner catheter 160 is uncoupled from the hub 210 by unthreading the distal end of the inner catheter 160 from the hub 210 by rotating the inner catheter 160 about its longitudinal axis. Then, in some embodiments the guidewire 110 is retracted to allow full deployment of the SAM containment member 212. The SAM containment member 212 may self-expand to its fully deployed configuration in some embodiments. The configuration of the fully deployed SAM containment member 212 is depicted in FIGS. 16-21 and 42, for example.

In its fully deployed configuration, the SAM containment member 212 is at least partially disposed behind the natural mitral valve anterior leaflet 20 (FIG. 12). The deployed SAM containment member 212 can reduce or prevent the potential for the natural mitral valve anterior leaflet 20 to "flop" outward and/or from being drawn by a Venturi effect into the left ventricular outflow tract (LVOT). Accordingly, the SAM containment member 212 can reduce the risk of full or partial blockages of the LVOT. In some patient scenarios, the potential for suffering future adverse health events, such as heart failure, is thereby reduced.

With the valve assembly 300 and the anchor assembly 200 fully deployed and functioning as desired, the remaining components of the delivery system 100 can be withdrawn. To do so, the valve delivery catheter 180 and the inner catheter 160 can be retracted into the guide catheter 120. Then the valve delivery catheter 180, the inner catheter 160, and the guide catheter 120 can be jointly or individually withdrawn from the patient.

Figure 31:
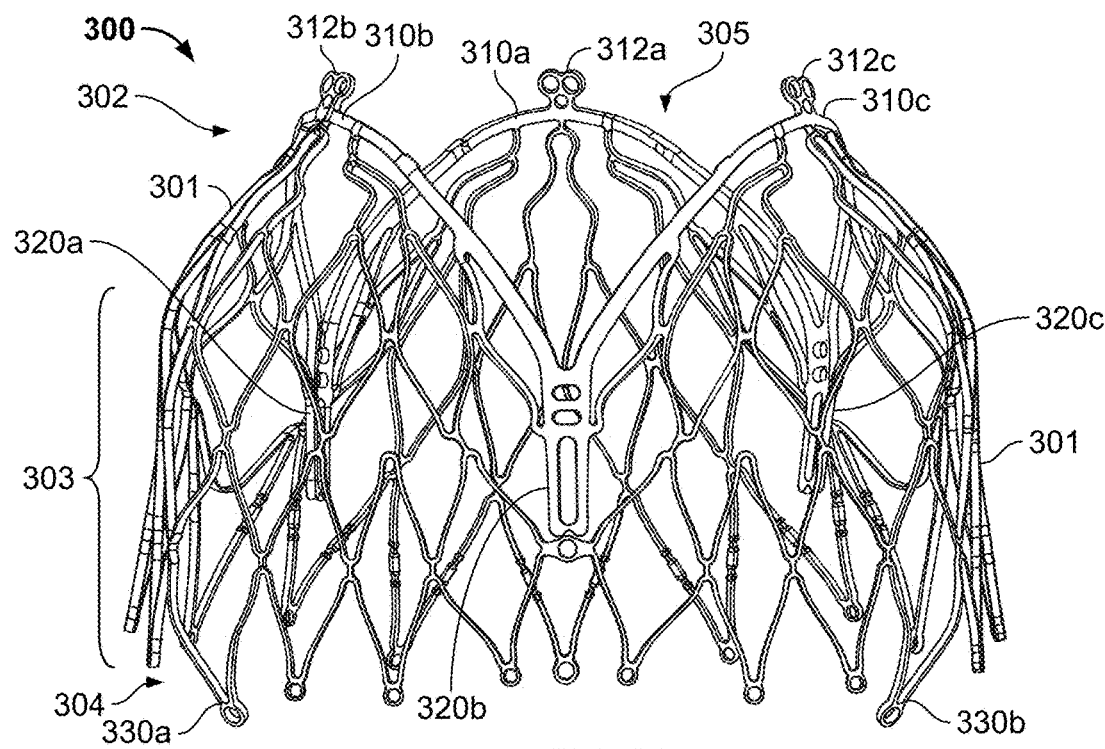
FIG. 31 shows an anterior side view of a valve frame of a valve assembly of FIGS. 26-30, in accordance with some embodiments.
Figure 32:
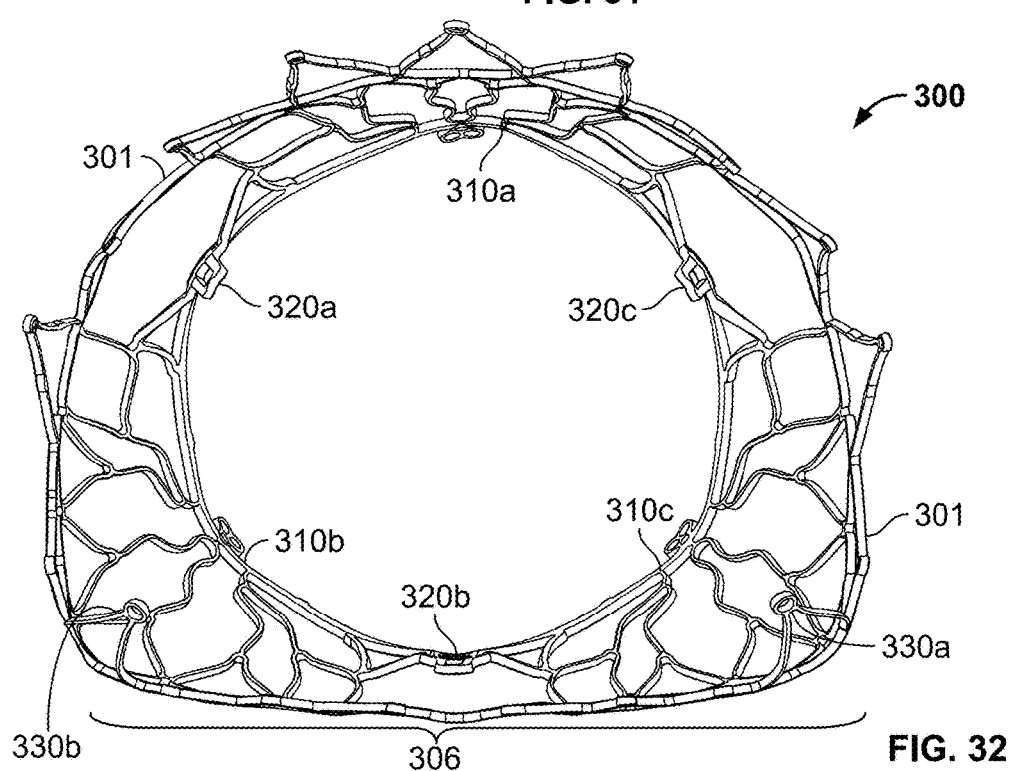
FIG. 32 shows a bottom view of the valve frame of FIG. 31.

Referring to FIGS. 31 and 32, an example valve assembly 300 is shown without any covering or valve/occluder leaflets. Hence, a valve assembly frame 301 of the valve assembly 300 is shown. FIG. 30 shows an anterior side view of the valve assembly frame 301, and FIG. 31 shows a bottom view of the valve assembly frame 301. The valve assembly 300 can be constructed using any of the various materials and manufacturing techniques described above in reference to the anchor frame 200 (e.g., refer to FIG. 9). It should be understood that the depicted valve assembly 300 is merely one non-limiting example of the valve assemblies provided within the scope of this disclosure.

The valve assembly 300 includes a proximal end portion 302 and a distal end portion 304. The valve assembly includes a flared external skirt portion 303 and defines an interior orifice portion 305. When the valve assembly 300 is implanted in a native mitral valve, the proximal end portion 302 is located supra-annular (in the left atrium) and the distal end portion 304 is located sub-annular (in the left ventricle). The proximal end portion 302 defines the generally circular entrance orifice of the valve assembly 300, as described further below.

In the depicted embodiment, the valve assembly 300 generally flares outward along a distal direction. Said differently, the distal end portion 304 is flared outward in comparison to the proximal end portion 302. Accordingly, the proximal end portion 302 defines a smaller outer profile in comparison to the distal end portion 304. However, some regions of the distal end portion 304 bow inwardly. In particular, for example, a posteromedial commissural corner 330a and anterolateral commissural corner 330b of the valve assembly 300 may bow inwardly. Such inward bowing of the commissural corners 330a and 330b can serve to mitigate LVOT obstructions and enhance sealing in some cases. It should be understood that the outward flare of the distal end portion 304 in comparison to the proximal end portion 302 is merely one example configuration for a profile of the valve assembly 300. In some embodiments, for example, a shoulder (a portion of the valve assembly 300 having the largest outer periphery) is located proximal of the middle of the valve assembly 300.

The valve assembly 300 also includes an anterior side 306 between the posteromedial commissural corner 330a and anterolateral commissural corner 330b. When the valve assembly 300 is implanted in a native mitral valve, the anterior side 306 faces the anterior leaflet of the native mitral valve. The anterior side 306 of the distal end portion 304 defines a generally flat surface, whereas the other sides of the distal end portion 304 are rounded. Hence, the periphery of the distal end portion 304 is generally D-shaped. The D-shaped periphery of the distal end portion 304 provides the valve assembly 300 with an advantageous outer profile for interfacing and sealing with the native mitral valve. As described further below, sealing is attained by coaptation between the D-shaped periphery of the distal end portion 304 and the leaflets of the native mitral valve, and, in some embodiments, between the D-shaped periphery in the region of the skirt 303 with the native valve annulus.

In the depicted embodiment, the proximal end portion 302 of the valve assembly 300 includes three atrial leaflet arches 310a, 310b, and 310c that together define an undulating ring at the proximal end portion 302. Each of the leaflet arches 310a, 310b, and 310c includes an apex having a one or more attachment holes 312a, 312b, and 312c respectively. In some embodiments, the attachment holes 312a, 312b, and 312c are used for coupling the proximal end of the valve assembly 300 to a delivery catheter (e.g., valve delivery catheter 180 of FIGS. 26-30 using proximal control wire 184a). In some embodiments, one or more of the attachment holes 312a, 312b, and 312c are used for containing radiopaque material.

The valve assembly 300 also includes three commissural posts 320a, 320b, and 320c that each extend distally from the intersections of the three leaflet arches 310a, 310b, and 310c. In some embodiments, the commissural posts 320a, 320b, and 320c are disposed at about 120° apart from each other. The commissural posts 320a, 320b, and 320c each have a series of holes that can be used for attachment of leaflets, such as by suturing. The three leaflet arches 310a, 310b, and 310c and the three commissural posts 320a, 320b, and 320c are areas on the valve assembly 300 to which three prosthetic valve leaflets become attached to comprise a tri-leaflet occluder (e.g., refer to FIG. 35).

As seen in FIG. 32, the three leaflet arches 310a, 310b, and 310c and the commissural posts 320a, 320b, and 320c define a generally cylindrical frame for the tri-leaflet occluder construct. As such, the valve assembly 300 provides a proven and advantageous frame configuration for the tri-leaflet occluder. The tri-leaflet occluder provides open flow during diastole and occlusion of flow during systole.

Referring to FIGS. 33, 34A, 34B and 35, in some embodiments the valve assembly 300 is configured to make the process of coupling one or more control wires (e.g., control wires 142a and 142b as described above in reference to FIGS. 3 and 4) to the valve assembly 300 more convenient. For example, in the depicted embodiment the valve assembly 300 is releasably coupled with a proximal end threading tube 185a and a distal end threading tube 185b. The threading tubes 185a and 185b can be used by a clinician as tools for threading the control wires 142a and 142b into engagement with the valve assembly 300. After using the threading tubes 185a and 185b to thread the control wires 142a and 142b into engagement with the valve assembly 300, the clinician can uncouple the threading tubes 185a and 185b from the valve assembly 300 and discard the threading tube 185a and 185b.

It should be understood that, in some embodiments, the valve assembly 300 is stored and transported to clinicians in sterile packaging containing a storage solution that keeps the valve assembly 300 moist. The storage solution is beneficial for preserving tissue of the valve assembly 300 during shipment and storage. The valve assembly 300 is not coupled to a delivery system during shipment and storage of the valve assembly 300. Therefore, an individual at the end-use site (e.g., a clinician in preparation for a procedure) will perform the task of coupling the valve assembly 300 to the delivery system (e.g., delivery system 100 as described above). In some embodiments, the task of coupling the valve assembly 300 to the delivery system includes coupling control wires (e.g., proximal control wire 184a and distal control wire 184b) to the valve assembly 300. Because the task of coupling control wires to the valve assembly 300 can be time-consuming, in some embodiments the valve assembly 300 is provided with one or more threading tubes, such as the proximal end threading tube 185a and the distal end threading tube 185b in the depicted embodiment.

The threading tubes 185a and 185b can be made of various materials such as, but not limited to, polyether ether ketone (PEEK), polyaryl ether ketone (PAEK), PTFE, FEP, HYTREL®, nylon, PICOFLEX®, PEBAX®, TECO-FLEX®, nitinol, and the like, and combinations thereof.

In some embodiments, the proximal end threading tube 185a is releasably engaged with the valve assembly 300. For example, in the depicted embodiment the proximal end threading tube 185a passes through one or more attachment features (suture loops in this example) at the attachment holes 312a, 312b, and 312c that are located at the apices of the leaflet arches 310a, 310b, and 310c respectively. In the depicted example of FIG. 34B, a suture loop 344a is attached at the apex of leaflet arch 310a using the attachment holes 312a. The same or a similar type of arrangement can be used at the attachment holes 312b and 312c located at the apices of leaflet arches 310b and 310c respectively. While in the depicted embodiment a single suture loop 344*a* is used, in some embodiments two or more suture loops are included at a single site. Such an arrangement can be used for redundancy, for example. The suture loops can be constructed of materials such as, but not limited to, ultra-high molecular weight polyethylene, nylon, polypropylene, polybutester, and the like. In some embodiments, other types of attachment elements (other than suture loops) such as, but not limited to, eyelets, grommets, rings, clips, pins, fabric portions, and/or the like, are used as to couple a threading tube (and control wire) to the valve assembly 300.

In some embodiments, the distal end threading tube 185*b* is releasably engaged with the valve assembly 300. For example, in the depicted embodiment the distal end threading tube 185*b* passes through one or more attachment features (suture loops in this example) that are located on or near the distal end of the framework of the valve assembly 300. In some embodiments, the distal end threading tube 185*b* can be used to couple the distal control wire 142*b* to the distal portion of the valve assembly 300.

In some implementations, a clinician can perform the following technique for using the threading tubes 185*a* and 185*b* to thread the control wires 142*a* and 142*b* into engagement with the valve assembly 300. For example, a clinician can insert a free end of the proximal control wire 142*a* into a lumen of the proximal end threading tube 185*a* at a first end of the proximal end threading tube 185*a*. The clinician can push the proximal control wire 142*a* in relation to the proximal end threading tube 185*a*, through the lumen of the proximal end threading tube 185*a*, until the free end emerges from a second end (opposite of the first end) of the proximal end threading tube 185*a*. Then, while holding the proximal control wire 142*a* essentially stationary in relation to the valve assembly 300, the clinician can slide the proximal end threading tube 185*a* out of engagement with the valve assembly 300, and off of the proximal control wire 142*a*. The proximal end threading tube 185*a* can then be discarded. The technique for using the distal end threading tube 185*b* to couple the distal control wire 142*b* to the distal portion of the valve assembly 300 can be the same technique as described in regard to the proximal end threading tube 185*a*. Thereafter, each of the free ends of the control wires 142*a* and 142*b*, having been passed through the suture loops, can be fed back into the distal portion of the valve delivery catheter 180 (FIGS. 26-30) and to a proximal securement and control system (not shown). The control wires 142*a* and 142*b* can then be tensioned which will reduce the diameter of the valve assembly 300, and allow for insertion into the distal end of the valve delivery sheath 170.

Still referring to FIGS. 33, 34A, 34B and 35, the valve assembly 300 can include an occluder portion, such as a tri-leaflet occluder or another type of occluder. For example, in the depicted embodiment the valve assembly 300 includes three leaflets 350*a*, 350*b*, and 350*c* that perform the occluding function of the prosthetic mitral valve 400. The cusps of the three leaflets 350*a*, 350*b*, and 350*c* are fixed to the three atrial leaflet arches 310*a*, 310*b*, and 310*c*, and to the three commissural posts 320*a*, 320*b*, and 320*c* (refer to FIGS. 20 and 21). The free edges of the three leaflets 350*a*, 350*b*, and 350*c* can seal by coaptation with each other during systole and open during diastole.

The three leaflets 350*a*, 350*b*, and 350*c* can be comprised of natural or synthetic materials. For example, the three leaflets 350*a*, 350*b*, and 350*c* can be comprised of any of the materials described above in reference to the covering 340, including the natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents. In some embodiments, the leaflets 350*a*, 350*b*, and 350*c* have a thickness in a range of about 0.005" to about 0.020" (about 0.13 mm to about 0.51 mm), or about 0.008" to about 0.012" (about 0.20 mm to about 0.31 mm). In some embodiments, the leaflets 350*a*, 350*b*, and 350*c* have a thickness that is less than about 0.005" (about 0.13 mm) or greater than about 0.020" (about 0.51 mm).

Referring also to FIGS. 36A and 36B, in some embodiments, prior to attaching the three leaflets 350*a*, 350*b*, and 350*c* to the framework of the valve assembly 300, the lateral edges of the three leaflets 350*a*, 350*b*, and 350*c* (or portions thereof) are folded and/or overlapped into engagement with each other. Such a technique can be used in preparation for securely attaching the three leaflets 350*a*, 350*b*, and 350*c* to the three commissural posts 320*a*, 320*b*, and 320*c*.

The depicted example folded configuration of the three leaflets 350*a*, 350*b*, and 350*c* effectively reduces the leaflet stresses in the commissural region when the valve is subjective to physiological pressures. Therefore, such engagement between the three leaflets 350*a*, 350*b*, and 350*c* can serve to improve the durability of the three leaflets 350*a*, 350*b*, and 350*c*.

In the depicted embodiment, each of the junctures of the lateral edges of the three leaflets 350*a*, 350*b*, and 350*c* includes a folded portion and an overlapping portion. For example, the juncture of leaflets 350*b* and 350*c* includes a folded portion 352*c* and an overlapping portion 352*bc*. The folded portion 352*c* is a lateral extension of the leaflet 350*c* that is folded onto the leaflet 350*b*. Alternatively, in some embodiments, a lateral extension of leaflet 350*b* can be folded onto leaflet 350*c*. The overlapping portion 352*bc* is made up of a lateral extension of each of the leaflets 350*b* and 350*c*. Hence, the overlapping portion 352*bc* includes two layers (a layer of leaflet 350*b* and a layer of leaflet 350*c*). Further, the overlapping portion 352*bc* of the leaflet assembly is wrapped around the commissural post 320*c* of the valve frame assembly 300. The same type of arrangement can be implemented at the commissural posts 320*a* and 320*b*. Such an arrangement can enhance the durability of the valve frame assembly 300 by reducing the likelihood of suture elongation/wear because of direct load transfer from the leaflets 350*a*, 350*b*, and 350*c* to the valve frame 301 (FIGS. 31 and 32) when subjected to physiological loading.

Referring also to FIG. 37, in some embodiments the commissural posts 320*a*, 320*b*, and 320*c* each have one or more openings that can be used for attachment of the three leaflets 350*a*, 350*b*, and 350*c*, such as by suturing. For example, commissural post 320*c*, as shown, defines a first opening 322*c*, a second opening 324*c*, and a third opening 326*c*. Each of the other commissural posts 320*a* and 320*b* can also define such openings.

The openings 322*c*, 324*c*, and 326*c* provide structural features that can be advantageously used for suturing the lateral edges of the leaflets 350*b* and 350*c* to the commissural post 320*c*. In some embodiments, the overlapping portion 352*bc* of leaflets 350*b* and 350*c* can be passed through the third opening 326*c*, and the overlapping portion 352*c* can be abutted against the portion of commissural post 320*c* that defines the first opening 322*c* and the second opening 324*c*. With the leaflets 350*b* and 350*c* in such an arrangement relative to the commissural post 320*c*, the lateral edges of the leaflets 350*b* and 350*c* can be sutured to the commissural post 320*c*. Such an arrangement can enhance the durability of the leaflets 350*b* and 350*c* by reducing the likelihood of suture elongation/wear because of direct load transfer from the leaflets 350b and 350c to the valve frame 301 (FIGS. 31 and 32) when subjected to physiological loading. Similar arrangements can be created at commissural posts 320a and 320b.

In some embodiments, a particular suture stitching pattern can be used to attach the lateral edges of the three leaflets 350a, 350b, and 350c to the commissural posts 320a, 320b, and 320c. Such a stitching pattern can advantageously result in a secure and durable attachment of the leaflets 350a, 350b, and 350c to the commissural posts 320a, 320b, and 320c. For example, FIG. 37 depicts an example suture stitching pattern 328 that can be used to attach the lateral edges of the leaflets 350b and 350c to the commissural post 320c. The depicted view of commissural post 320c is from the outside of the valve assembly 300.

In some embodiments, the example stitching pattern 328 is used to attach the lateral edges of the leaflets 350b and 350c to the commissural post 320c. The solid lines of the stitching pattern 328 represent sutures that are visible in this view. The dashed lines of the stitching pattern 328 represent sutures that are not visible in this view. The stitching pattern 328 can include suture knots at various locations. For example, two suture knots can be tied in or near the first opening 322c. One or more knots can also be tied at a distal end 329 of the commissural post 320c.

Figure 38:
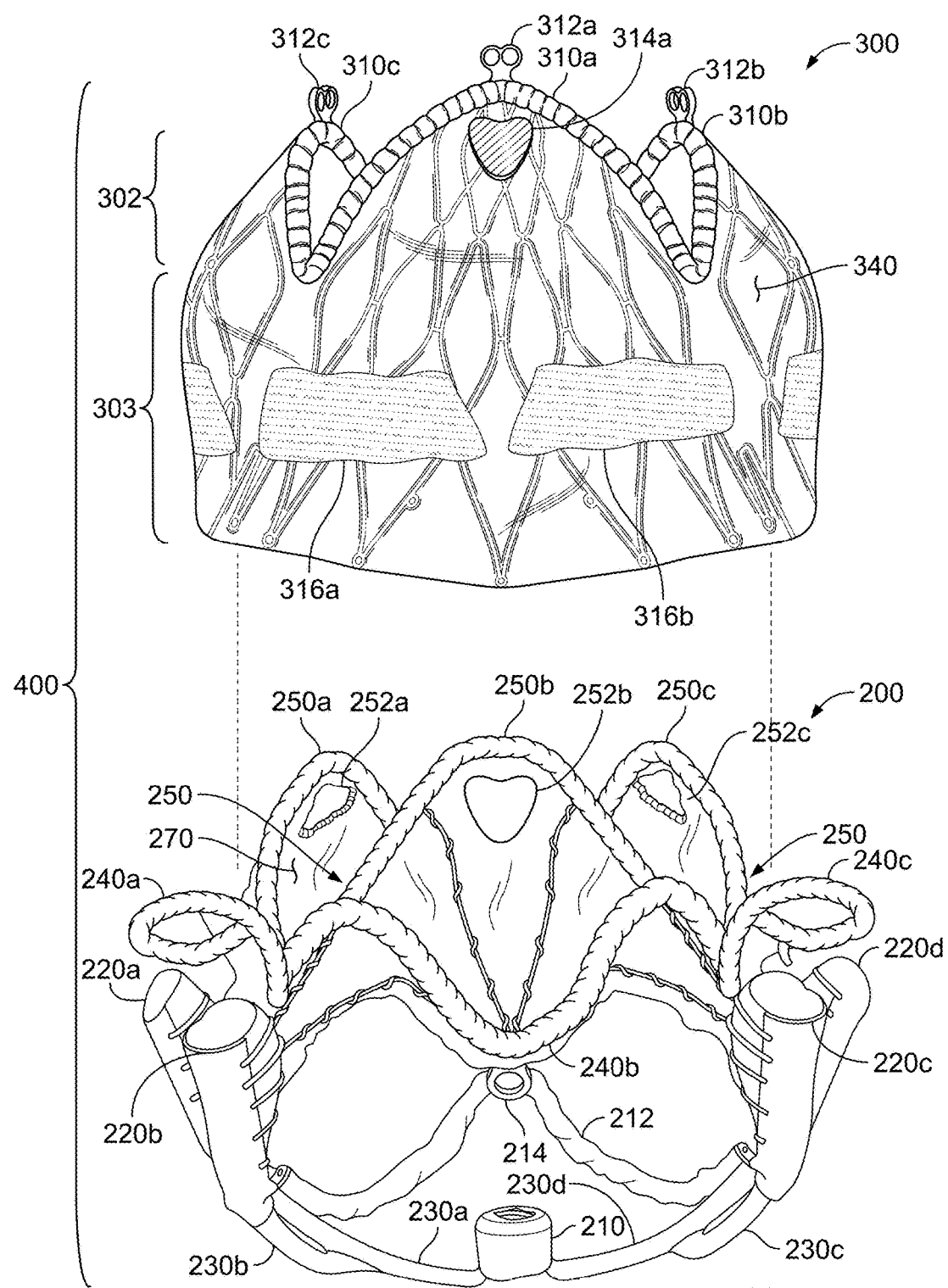
FIG. 38 is an exploded posterior side view of the anchor assembly and valve assembly of FIGS. 26-30, in accordance with some embodiments.
Figure 39:
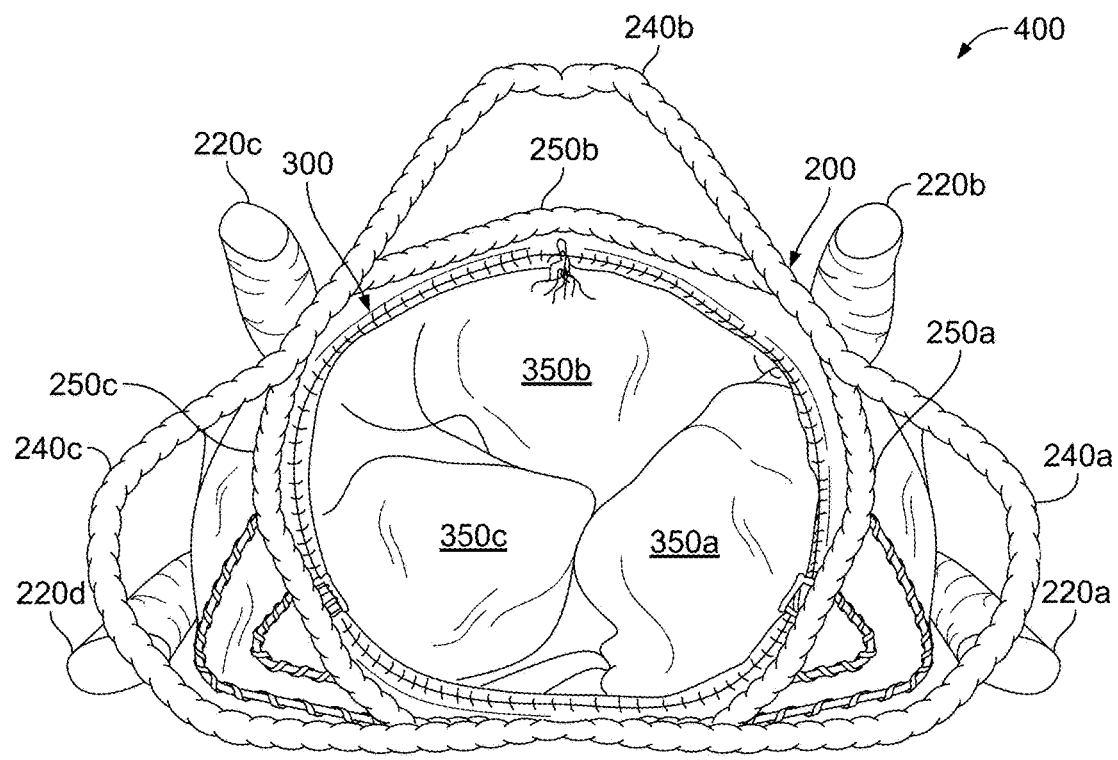
FIG. 39 is a top view of an example prosthetic mitral valve system that includes a valve assembly engaged with an anchor assembly, in accordance with some embodiments.

Referring to FIG. 38, an exploded depiction of an example prosthetic mitral valve 400 includes an anchor assembly 200 and a valve assembly 300. This figure provides a posterior side view of the anchor assembly 200 and the valve assembly 300.

The valve assembly 300 includes a covering 340. The covering 340 can be made of any of the materials and constructed using any of the techniques described above in reference to covering 270. Additionally, in some embodiments the covering 340 can comprise natural tissues such as, but not limited to, bovine, porcine, ovine, or equine pericardium. In some such embodiments, the tissues are chemically cross-linked using glutaraldehyde, formaldehyde, or triglycidyl amine solution, or other suitable crosslinking agents.

When the valve assembly 300 and the anchor assembly 200 are coupled together, the valve assembly 300 is geometrically interlocked within the interior defined by the anchor assembly 200 (e.g., in some embodiments by virtue of the tapered shape of the proximal end 302 valve assembly 300 within the supra-annular ring 250 and interior space defined by the anchor assembly 200). In particular, in some embodiments the valve assembly 300 is contained within the interior space between the supra-annular ring 250 and the sub-annular support arms 230a, 230b, 230c, and 230d. As described above, the interlocked arrangement between the valve assembly 300 and the anchor assembly 200 is accomplished by positioning a valve assembly 300 in a low-profile configuration within the interior of the anchor assembly 200 and then allowing expansion of the valve assembly 300 within the interior of the anchor assembly 200 (e.g., refer to FIGS. 28-30).

In some embodiments, such as the depicted embodiment, a fabric portion 314a is attached (e.g., sewn) to the outer surface of coving 340 near the apex of the leaflet arch 310a. The other leaflet arches 310b and 310c can also have such a fabric portion. The fabric portion 314a aligns up with the covering-material cut out 252b of the anchor assembly 200 when the valve assembly 300 is coupled with the anchor assembly 200. By positioning the fabric portion 314a within the covering-material cut out 252b, the valve assembly 300 becomes coupled with the anchor assembly 200 with an additional resiliency. This additional securement resiliency may be advantageous, for example, to resist migration of the valve assembly 300 into the ventricle during diastole.

While in the depicted embodiment a triangular shape is used for the fabric portion 314a and the covering-material cut out 252b, in some embodiments other shapes such as, but not limited to, polygons, circles, ovals, and the like can be used. In some embodiments, the fabric portion 314a (and the other fabric portions on leaflet arches 310b and 310c) is made of a material such as, but not limited to, felt, polyester, a silicone, a urethane, ELAST-EON™ (a silicone and urethane polymer), another biocompatible polymer, DACRON®, polyethylene terephthalate (PET), copolymers, or combinations and subcombinations thereof.

In some embodiments, one or more supplementary covering portions are attached (e.g., sewn) to the outer surface of the covering 340 of the valve assembly 300. In some cases, such supplementary covering portions can provide an enhanced sealing capability between the skirt 303 and surrounding native tissues when the prosthetic mitral valve 400 is deployed in a native mitral valve. Moreover, such supplementary covering portions can facilitate tissue healing and/or ingrowth, which can in turn provide enhanced sealing. For example, in the depicted embodiment, the valve assembly 300 includes a first supplementary covering portion 316a and a second supplementary covering portion 316b. In some embodiments, the first supplementary covering portion 316a and the second supplementary covering portion 316b are made of a material such as, but not limited to, DACRON®, felt, polyester, a silicone, a urethane, ELAST-EON™ (a silicone and urethane polymer), another biocompatible polymer, polyethylene terephthalate (PET), copolymers, or combinations and subcombinations thereof.

Referring to FIGS. 39-42, the prosthetic mitral valve 400 (comprised of the valve assembly 300 coupled within the anchor assembly 200) is shown in top (atrial), anterior, posterior, and bottom (ventricle) views, respectively. In some embodiments, the occluding function of the prosthetic mitral valve 400 can be performed using configurations other than the depicted tri-leaflet occluder. For example, bi-leaflet, quad-leaflet, or mechanical valve constructs can be used in some embodiments.

Figure 40:
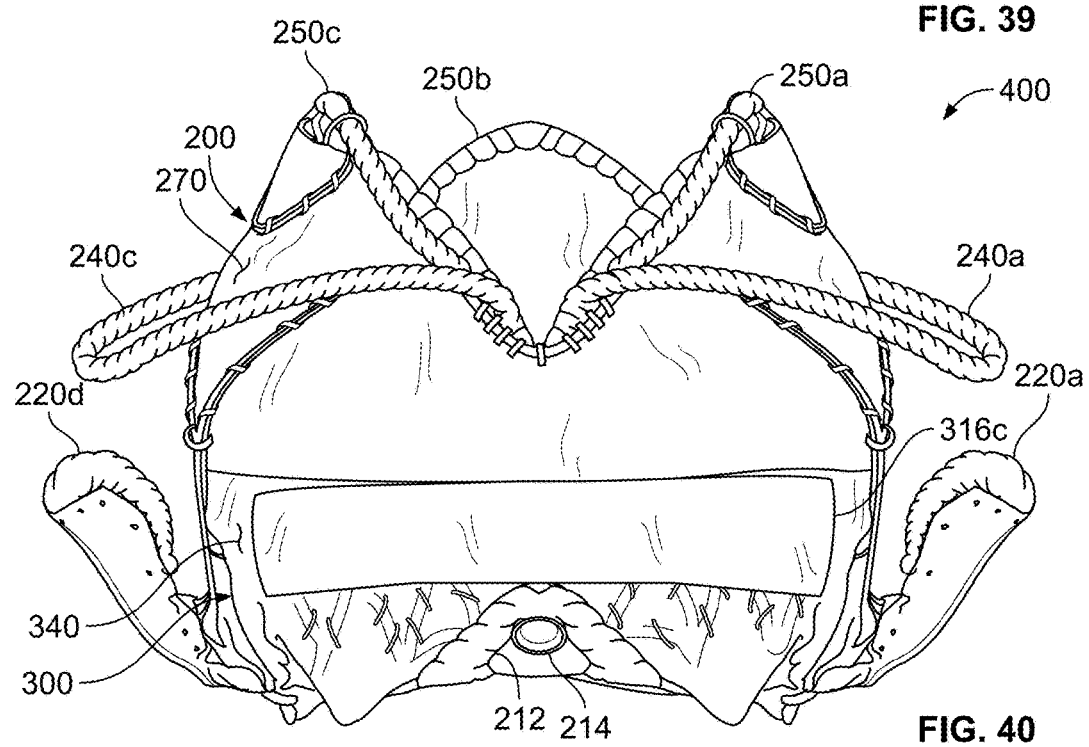
FIG. 40 is an anterior view of the prosthetic mitral valve system of FIG. 38.
Figure 41:
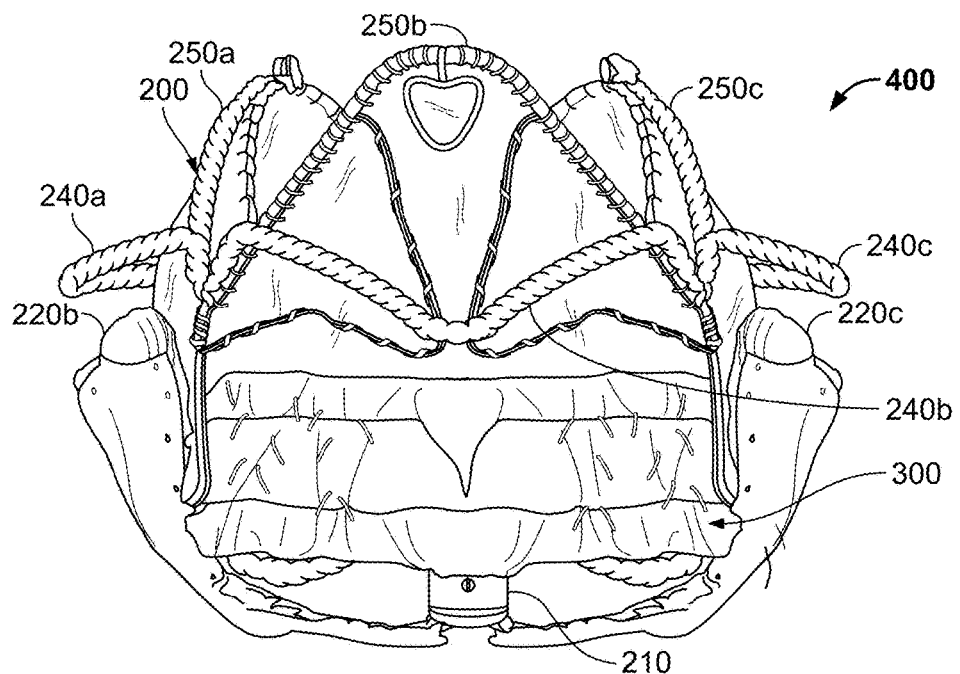
FIG. 41 is a posterior view of the prosthetic mitral valve system of FIG. 38.
Figure 42:
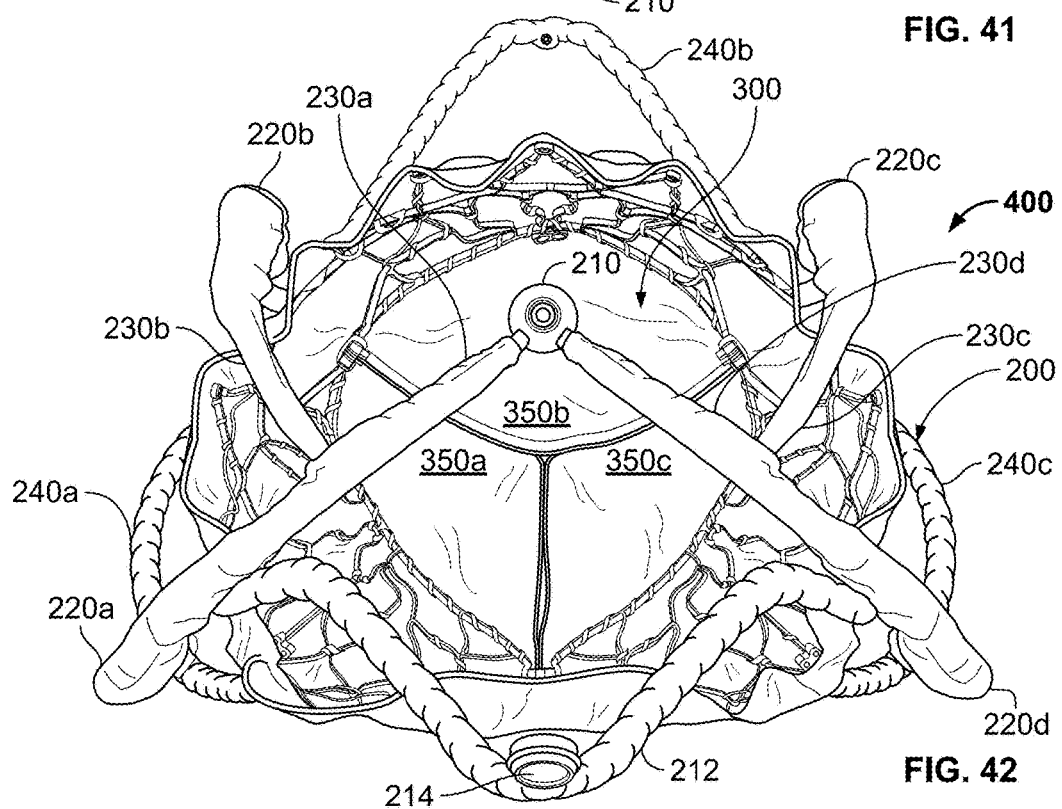
FIG. 42 is a bottom view of the prosthetic mitral valve system of FIG. 38.

As shown in FIG. 40, a supplemental covering portion 316c can positioned on an anterior surface of the valve assembly 300. The supplemental covering portion 316c can provide an enhanced sealing capability between the skirt 303 and surrounding native tissues (e.g., an anterior leaflet) when the prosthetic mitral valve 400 is deployed in a native mitral valve. The supplemental covering portion 316c can be made of a material such as, but not limited to, DACRON®, felt, polyester, a silicone, a urethane, ELAST-EON™ (a silicone and urethane polymer), another biocompatible polymer, polyethylene terephthalate (PET), copolymers, or combinations and subcombinations thereof.

Figure 43:
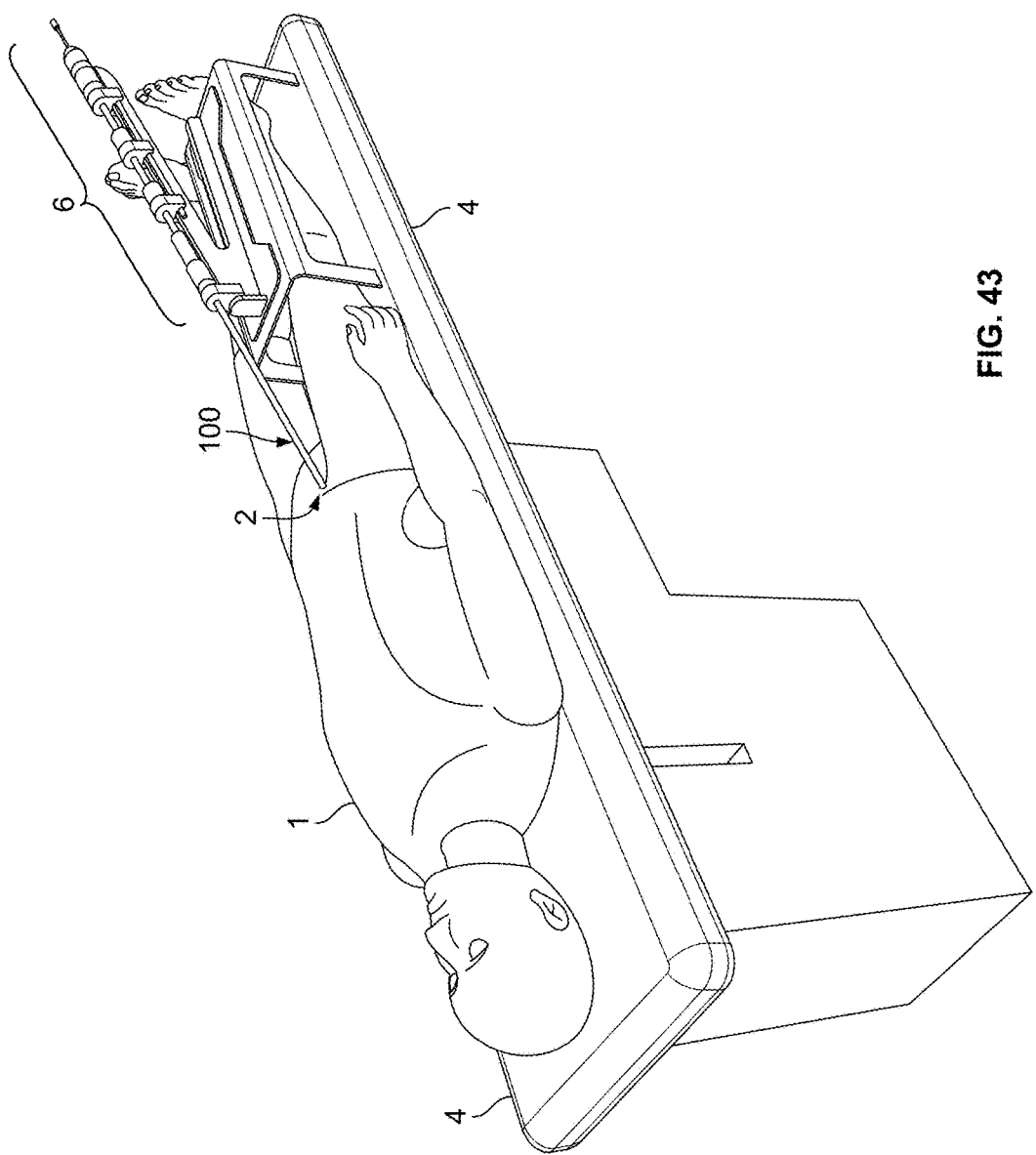
FIG. 43 shows a perspective view of an example prosthetic mitral valve system deployment frame system configuration in accordance with some embodiments.

Referring to FIG. 43, in some implementations the prosthetic mitral valve 400 of FIGS. 39-42 is deployed in a patient 1 using the transcatheter delivery system 100 as described above. In some implementations, the prosthetic mitral valve 400 is percutaneously deployed via a femoral or iliac vein through a groin opening/incision 2 in the patient 1. In particular implementations, a deployment frame system 6 is used to initiate and/or control the movements of various components of the transcatheter delivery system 100.

While the deployment frame system 6 is described in the context of the deployment of the prosthetic mitral valve 400 using the transcatheter delivery system 100, it should be understood that the practical applications of the inventive concepts associated with the deployment frame system 6 is not limited to such a context. That is, the inventive concepts associated with the deployment frame system 6 can be applied to contexts such as, but not limited to, other types of delivery systems for prosthetic heart valves of any type, deployment systems for other types of medical devices/implants, and so on.

In the depicted embodiment, the deployment frame system 6 is attached or releasably attached to an operating table 4 on which the patient 1 is laying. In some embodiments, the deployment frame system 6 is separated or substantially separated from the operating table 4.

As described above in reference to FIGS. 1-11 and 25-30, the deployment of the prosthetic mitral valve 400 is, in summary, a two-step process. The first step is the deployment of the anchor assembly 200, and the second step is the deployment of the valve assembly 300. Some components of the deployment frame system 6 may be used for both steps, while other components of the deployment frame system 6 may be used for one or the other of the two steps.

In general, the configuration of the deployment frame system 6 is different for the two deployment steps (i.e., the first step being the deployment of the anchor assembly 200, and the second step being the deployment of the valve assembly 300). That is, the configuration of the deployment frame system 6 for delivering the anchor assembly 200 is different than the configuration of the deployment frame system 6 for delivering the valve assembly 300.

The transcatheter delivery system 100 can be releasably coupled with deployment frame system 6, as described further below. The deployment frame system 6 can be used by one or more clinicians to initiate and control movements of the components of the delivery system 100. Some such movements of the components of the delivery system 100 are described above in reference to FIGS. 1-11 and 25-30.

As described above, the example transcatheter delivery system 100 includes the guidewire 110, the guide catheter 120, the anchor delivery sheath 130, the anchor delivery catheter 140, the secondary steerable catheter 150, and the inner catheter 160. In general, in the depicted embodiment those components of delivery system 100 are disposed in a telescopic fashion in relation to each other. That is, the guidewire 110 is slidably disposed within the inner catheter 160; the inner catheter 160 is slidably disposed within the secondary steerable catheter 150; the secondary steerable catheter 150 is slidably disposed within the anchor delivery catheter 140; the anchor delivery catheter 140 is slidably disposed within the anchor delivery sheath 130; and the anchor delivery sheath 130 is slidably disposed within the guide catheter 120.

A proximal end portion of those components (e.g., the guide catheter 120, the anchor delivery sheath 130, the anchor delivery catheter 140, the secondary steerable catheter 150, and the inner catheter 160) can be terminated at a respective location along the deployment frame system 6. As described further below, by manipulating the respective components' proximal end portions (individually or in unison) using the deployment frame system 6, clinicians can initiate and control movements of the delivery system 100. In some embodiments, the example deployment frame system 6 includes a main frame and a secondary frame.

As described above in reference to FIGS. 1-11 and 25-30, various movements of the components of the delivery system 100 may be desired during the process of deploying (or retrieving) a medical device, such as the anchor assembly 200 and valve assembly 300 of prosthetic mitral valve 400 (refer to FIG. 38). For example, the types of desired movements of the components of the delivery system 100 may include, but are not limited to: (i) a distal longitudinal translation, (ii) a proximal longitudinal translation, (iii) rotations about the longitudinal axis in either direction, (iv) a deflection of one or more portions of a component (e.g., steering or bending), and (v) a tensioning or untensioning of a control wire.

In some implementations, it may be desirable to initiate some of such movements (e.g., example movements (i)-(v) above) in synchronization (e.g., generally simultaneously) with one or more other such movements. One example, of desirable simultaneous movement of two or more components of the delivery system 100 was described above in reference to FIG. 7. In that example, the inner catheter 160 and the anchor delivery catheter 140 were translated distally in conjunction with each other, while maintaining the positions of the other components of the delivery system 100 (e.g., the secondary steerable catheter 150) generally stationary. The secondary frame of the deployment frame system 6 can be advantageously utilized to facilitate such synchronization of movements of two or more components of the delivery system 100.

A number of embodiments of the invention have been described. Nevertheless, it will be understood that various modifications may be made without departing from the scope of the invention. Accordingly, other embodiments are within the scope of the following claims.

What is claimed is:

1. A prosthetic mitral valve system comprising:
    a valve assembly comprising an expandable valve frame and an occluder attached to the expandable valve frame;
    an anchor assembly comprising an expandable anchor frame that defines a longitudinal axis, the anchor assembly configured to selectively couple with the valve assembly; and
    a control wire slidably engaged with the expandable anchor frame at a plurality of engagement locations at a mid-body region along the longitudinal axis of the expandable anchor frame, the control wire being manipulable to increase and decrease a diameter of the expandable anchor frame during implantation of the anchor assembly.

2. The prosthetic mitral valve system of claim 1, wherein the expandable anchor frame comprises:
    a centrally located hub;
    a first elongate element extending from the hub, the first elongate element including a first foot;
    a second elongate element extending from the hub, the second elongate element including a second foot;
    a third elongate element extending from the first elongate element, the third elongate element including a third foot; and
    a fourth elongate element extending from the second elongate element, the fourth elongate element including a fourth foot.

3. The prosthetic mitral valve system of claim 2, wherein tensioning the control wire draws each of the first foot, second foot, third foot, and fourth foot radially inwards towards the longitudinal axis, and wherein slackening the control wire allows each of the first foot, second foot, third foot, and fourth foot to expand radially outwards away from the longitudinal axis.

4. The prosthetic mitral valve system of claim 1, wherein the control wire is a first control wire, and further comprising a second control wire slidably engaged with the expandable anchor frame at a proximal end region of the expandable anchor frame.

5. The prosthetic mitral valve system of claim 4, wherein the proximal end region of the expandable anchor frame comprises a plurality of arched atrial holding features, and wherein the second control wire is manipulable such that tensioning the second control wire draws the plurality of arched atrial holding features radially inwards towards the longitudinal axis and slackening the second control wire allows the plurality of arched atrial holding features to extend transversely outward in relation to the longitudinal axis.

6. The prosthetic mitral valve system of claim 1, wherein: the expandable valve frame comprises three valve frame lobes disposed on a proximal end portion of the expandable valve frame; the expandable anchor frame comprises three anchor frame lobes disposed on a proximal end portion of the expandable anchor frame; and wherein, while the valve assembly and the anchor assembly are coupled, each valve frame lobe of the three valve frame lobes is aligned with a respective anchor frame lobe of the three anchor frame lobes.

7. The prosthetic mitral valve system of claim 5, wherein: the expandable valve frame comprises three valve frame lobes disposed on a proximal end portion of the expandable valve frame; the expandable anchor frame comprises three anchor frame lobes disposed on a proximal end portion of the expandable anchor frame; and wherein, while the valve assembly and the anchor assembly are coupled, each valve frame lobe of the three valve frame lobes is aligned with a respective anchor frame lobe of the three anchor frame lobes.

8. The prosthetic mitral valve system of claim 7, wherein the plurality of arched atrial holding features comprises three arched atrial holding features.

9. The prosthetic mitral valve system of claim 5, wherein the plurality of arched atrial holding features comprises three arched atrial holding features.

10. The prosthetic mitral valve system of claim 2, wherein the expandable anchor frame further comprises a systolic anterior motion containment member that is configured to be at least partially disposed behind an anterior leaflet of the native mitral valve while the anchor assembly is coupled to the native mitral valve.

11. The prosthetic mitral valve system of claim 10, wherein the systolic anterior motion containment member extends from the first elongate element and the second elongate element.

12. The prosthetic mitral valve system of claim 2, wherein the hub is located at a distal end of the expandable anchor frame.

13. The prosthetic mitral valve system of claim 12, wherein the hub is threaded for releasable attachment with a delivery device.

14. The prosthetic mitral valve system of claim 1, wherein the valve assembly comprises: the expandable valve frame comprising an expandable metallic structure, an outer covering material along an exterior of the expandable metallic structure, and the occluder attached to the expandable metallic structure.

15. The prosthetic mitral valve system of claim 1, wherein the anchor assembly is configured to selectively couple with the valve assembly by expansion of the valve assembly within the anchor assembly subsequent to implantation of the anchor assembly.

16. The prosthetic mitral valve system of claim 15, wherein the valve assembly is deliverable to the anchor assembly after the anchor assembly is expanded and secured at an implantation site.

17. The prosthetic mitral valve system of claim 1, wherein the control wire is manipulable to increase and decrease the diameter of the expandable anchor frame during implantation of the anchor assembly prior to selectively coupling with the valve assembly with the anchor assembly.

18. The prosthetic mitral valve system of claim 17, wherein the control wire is removable from all of said plurality of engagement locations at the mid-body region of the expandable anchor frame to expand the anchor frame while the valve assembly is decoupled from the anchor assembly.

19. The prosthetic mitral valve system of claim 18, wherein the control wire is removable from all of said plurality of engagement locations at the mid-body region of the expandable anchor frame to expand the anchor frame while the valve assembly remains in a collapsed configuration.

20. The prosthetic mitral valve system of claim 1, wherein said control wire is removably and slidably engaged with at least two engagement locations at the mid-body region of the expandable anchor frame.

21. The prosthetic mitral valve system of claim 20, wherein said control wire is looped through at least four of engagement locations at the mid-body region of the expandable anchor frame.

22. The prosthetic mitral valve system of claim 1, wherein said control wire is movable to individually and exclusively control said decrease of the diameter of the expandable anchor frame during implantation of the anchor assembly.

23. The prosthetic mitral valve system of claim 4, wherein said second control wire is removably and slidably engaged with at least two engagement locations at the proximal end region of the expandable anchor frame, the second end wire being removable from the expandable anchor frame independently and separately from the first control wire.

24. The prosthetic mitral valve system of claim 4, further comprising a valve expansion control wire to slidably and removably connect with the expandable valve frame to control a diameter of the valve assembly independently from expansion of the anchor assembly.

25. The prosthetic mitral valve system of claim 24, wherein the valve expansion control wire is removable from the expandable valve frame independently and separately from removal of the first and second control wires from the expandable anchor frame.

26. A prosthetic mitral valve system comprising:
a valve assembly comprising an expandable valve frame and an occluder attached to the expandable valve frame;
an anchor assembly comprising an expandable anchor frame that defines a longitudinal axis, the anchor assembly configured to selectively couple with the valve assembly; and
a control wire slidably engaged with the expandable anchor frame at a plurality of engagement locations at a mid-body region along the longitudinal axis of the expandable anchor frame, the control wire being manipulable to increase and decrease a diameter of the expandable anchor frame during implantation of the anchor assembly;
wherein the control wire is a first control wire, and further comprising a second control wire slidably engaged with the expandable anchor frame at a proximal end region of the expandable anchor frame;

wherein the proximal end region of the expandable anchor frame comprises a plurality of arched atrial holding features, and wherein the second control wire is manipulable such that tensioning the second control wire draws the plurality of arched atrial holding features radially inwards towards the longitudinal axis and slackening the second control wire allows the plurality of arched atrial holding features to extend transversely outward in relation to the longitudinal axis:

wherein: the expandable valve frame comprises three valve frame lobes disposed on a proximal end portion of the expandable valve frame; the expandable anchor frame comprises three anchor frame lobes disposed on a proximal end portion of the expandable anchor frame; and wherein, while the valve assembly and the anchor assembly are coupled, each valve frame lobe of the three valve frame lobes is aligned with a respective anchor frame lobe of the three anchor frame lobes;

wherein the plurality of arched atrial holding features comprises three arched atrial holding features; and wherein each arched atrial holding feature of the three arched atrial holding features is aligned with a corresponding valve frame lobe of the three valve frame lobes and with a corresponding anchor frame lobe of the three anchor frame lobes.

27. The prosthetic mitral valve system of claim 26, wherein the valve assembly comprises: the expandable valve frame comprising an expandable metallic structure, an outer covering material along an exterior of the expandable metallic structure, and the occluder attached to the expandable metallic structure.

28. The prosthetic mitral valve system of claim 26, wherein the anchor assembly is configured to selectively couple with the valve assembly by expansion of the valve assembly within the anchor assembly subsequent to implantation of the anchor assembly.

29. The prosthetic mitral valve system of claim 26, wherein said control wire is manipulable to increase and decrease the diameter of the expandable anchor frame during implantation of the anchor assembly prior to selectively coupling with the valve assembly with the anchor assembly.

30. The prosthetic mitral valve system of claim 26, wherein the expandable anchor frame further comprises a systolic anterior motion containment member that is configured to be at least partially disposed behind an anterior leaflet of the native mitral valve while the anchor assembly is coupled to the native mitral valve.

\* \* \* \* \*